United States Patent
Eder et al.

(10) Patent No.: US 11,931,430 B2
(45) Date of Patent: Mar. 19, 2024

(54) LABELED INHIBITORS OF PROSTATE SPECIFIC MEMBRANE ANTIGEN (PSMA) AS AGENTS FOR THE TREATMENT OF PROSTATE CANCER

(71) Applicants: DEUTSCHES KREBSFORSCHUNGSZENTRUM, Heidelberg (DE); RUPRECHT-KARLS-UNIVERSITÄT HEIDELBERG, Heidelberg (DE)

(72) Inventors: Matthias Eder, Mannheim (DE); Klaus Kopka, Dossenheim (DE); Martin Schäfer, Neckarsteinach (DE); Ulrike Bauder-Wüst, Schriesheim (DE); Michael Eisenhut, Heidelberg (DE); Walter Mier, Bensheim (DE); Martina Benesova, Heidelberg (DE)

(73) Assignee: NOVARTIS AG, Basel (CH)

( * ) Notice: Subject to any disclaimer, the term of this patent is extended or adjusted under 35 U.S.C. 154(b) by 379 days.

(21) Appl. No.: 17/110,558

(22) Filed: Dec. 3, 2020

(65) Prior Publication Data
US 2021/0177996 A1 Jun. 17, 2021

Related U.S. Application Data

(60) Division of application No. 16/551,198, filed on Aug. 26, 2019, now Pat. No. 11,045,564, which is a division of application No. 16/114,988, filed on Aug. 28, 2018, now Pat. No. 10,398,791, which is a continuation of application No. 15/131,118, filed on Apr. 18, 2016, now abandoned, which is a continuation-in-part of application No. PCT/EP2014/002808, filed on Oct. 17, 2014.

(30) Foreign Application Priority Data

Oct. 18, 2013 (EP) ................................. 13004991
Jul. 3, 2014 (EP) ................................. 14175612

(51) Int. Cl.
| | | |
|---|---|---|
| A61K 51/04 | (2006.01) | |
| C07B 59/00 | (2006.01) | |
| C07D 257/02 | (2006.01) | |
| C07D 295/145 | (2006.01) | |

(52) U.S. Cl.
CPC ...... *A61K 51/0482* (2013.01); *A61K 51/0402* (2013.01); *A61K 51/0497* (2013.01); *C07B 59/002* (2013.01); *C07D 257/02* (2013.01); *C07D 295/145* (2013.01)

(58) Field of Classification Search
CPC ....... A61K 51/04; A61K 49/00; C07D 257/02
See application file for complete search history.

(56) References Cited

U.S. PATENT DOCUMENTS

| | | | |
|---|---|---|---|
| 4,691,024 A | 9/1987 | Kunikatsu et al. | |
| 4,713,249 A | 12/1987 | Schröder | |
| 5,103,018 A | 4/1992 | Motomichi et al. | |
| 5,266,333 A | 11/1993 | Cady et al. | |
| 5,417,982 A | 5/1995 | Modi | |
| 5,418,982 A | 5/1995 | Kishi | |
| 5,627,165 A | 5/1997 | Glazier | |
| 5,795,877 A | 8/1998 | Jackson et al. | |
| 5,863,536 A | 1/1999 | Jackson et al. | |
| 5,866,679 A | 2/1999 | DeFeo-Jones et al. | |
| 5,902,817 A | 5/1999 | Jackson et al. | |
| 5,948,750 A | 9/1999 | Garsky et al. | |
| 5,962,237 A | 10/1999 | Ts'o et al. | |
| 5,962,521 A | 10/1999 | Jackson et al. | |
| 5,968,915 A | 10/1999 | Jackson et al. | |
| 5,998,362 A | 12/1999 | Feng et al. | |
| 6,054,444 A | 4/2000 | Jackson et al. | |
| 6,068,830 A | 5/2000 | Diamandis et al. | |
| 6,127,333 A | 10/2000 | Brady et al. | |
| 6,174,858 B1 | 1/2001 | Brady et al. | |
| 6,177,404 B1 | 1/2001 | DeFeo-Jones et al. | |
| 6,232,287 B1 | 5/2001 | Ruoslahti et al. | |
| 6,265,540 B1 | 7/2001 | Isaacs et al. | |
| 6,342,491 B1 | 1/2002 | Dey et al. | |
| 6,355,611 B1 | 3/2002 | Karki et al. | |
| 6,368,598 B1 | 4/2002 | D'Amico et al. | |
| 6,391,305 B1 | 5/2002 | Feng et al. | |

(Continued)

FOREIGN PATENT DOCUMENTS

| | | |
|---|---|---|
| AU | 2008289108 B2 | 2/2009 |
| CA | 2606138 A1 | 10/2005 |

(Continued)

OTHER PUBLICATIONS

Zhou J., "In vivo evaluation of medical device-associated inflammation using macrophage-specific position emission tomography (PET) imaging," Bioorganic and Medicinal Chemistry Letters, 2013 vol. 23, p. 2044-2047.

Kularatne SA., et al. "Comparative Analysis of Folate Derived PET Imaging Agents with [18F]-2-Fluoro-2-deoxy-D- glucose Using Rodent Inflammatory Paw Model," Molecular Pharmaceutics, 2013 vol. 10, p. 3103-3111.

Office Action for co-pending Canadian Application No. 2924360, dated Sep. 11, 2018.

Examination Report for co-pending Australian Patent Application No. 2018200419, Oct. 24, 2018.

Office Action for co-pending Japanese Patent Application No. 2017-210775, mailed Nov. 6, 2018.

(Continued)

*Primary Examiner* — Michael G. Hartley
*Assistant Examiner* — Jagadishwar R Samala
(74) *Attorney, Agent, or Firm* — THE MARBURY LAW GROUP, PLLC

(57) ABSTRACT

The present invention generally relates to the field of radiopharmaceuticals and their use in nuclear medicine as tracers, imaging agents and for the treatment of various disease states of prostate cancer. Thus, the present invention concerns compounds that are represented by the general Formulae (Ia) or (Ib).

15 Claims, 20 Drawing Sheets

(56) References Cited

U.S. PATENT DOCUMENTS

| | | | |
|---|---|---|---|
| 6,428,785 | B1 | 8/2002 | Gocken |
| 6,479,470 | B1 | 11/2002 | Kozikowski et al. |
| 6,504,014 | B1 | 1/2003 | Saacs et al. |
| 6,511,676 | B1 | 1/2003 | Boulikas |
| 6,518,033 | B1 | 2/2003 | Gromeier et al. |
| 6,528,499 | B1 | 3/2003 | Kozikowski et al. |
| 6,548,260 | B1 | 4/2003 | Tewari |
| 6,596,755 | B2 | 7/2003 | Burman et al. |
| 6,602,274 | B1 | 8/2003 | Chen |
| 6,613,793 | B2 | 9/2003 | Burman et al. |
| 6,692,724 | B1 | 2/2004 | Yang et al. |
| 6,875,886 | B2 | 4/2005 | Frangioni |
| 6,946,133 | B1 | 9/2005 | Schlom et al. |
| 7,005,429 | B2 | 2/2006 | Dey et al. |
| 7,008,765 | B1 | 3/2006 | Bussemakers et al. |
| 7,041,786 | B2 | 5/2006 | Shailubhai et al. |
| 7,045,605 | B2 | 5/2006 | Bander et al. |
| 7,052,703 | B1 | 5/2006 | Pastan et al. |
| 7,060,284 | B1 | 6/2006 | Kaumaya |
| 7,128,893 | B2 | 10/2006 | Leamon et al. |
| 7,129,254 | B2 | 10/2006 | Berger et al. |
| 7,147,837 | B2 | 12/2006 | Lauffer et al. |
| 7,153,841 | B2 | 12/2006 | Roncucci et al. |
| 7,160,885 | B2 | 1/2007 | Currie et al. |
| 7,166,691 | B2 | 1/2007 | Koochekpour et al. |
| 7,192,586 | B2 | 3/2007 | Bander |
| 7,226,577 | B2 | 6/2007 | Cappelletti et al. |
| 7,232,805 | B2 | 6/2007 | Weinshenker et al. |
| 7,238,785 | B2 | 7/2007 | Govindan et al. |
| 7,282,567 | B2 | 10/2007 | Goldenberg et al. |
| 7,361,338 | B2 | 4/2008 | Jakobovits et al. |
| 7,381,745 | B2 | 6/2008 | Kozikowski et al. |
| 7,399,460 | B2 | 7/2008 | Wedeking et al. |
| 7,408,079 | B2 | 8/2008 | Pomper et al. |
| 7,468,354 | B2 | 12/2008 | Isaacs |
| 7,485,299 | B2 | 2/2009 | Afar et al. |
| 7,514,078 | B2 | 4/2009 | Bander et al. |
| 7,517,903 | B2 | 4/2009 | Chen et al. |
| 7,534,580 | B2 | 5/2009 | Reeves et al. |
| 7,547,773 | B2 | 6/2009 | Schlom et al. |
| 7,585,491 | B2 | 9/2009 | Govindan |
| 7,601,332 | B2 | 10/2009 | Mahov et al. |
| 7,635,682 | B2 | 12/2009 | Denmeade et al. |
| 7,638,122 | B2 | 12/2009 | Yu et al. |
| 7,638,525 | B2 | 12/2009 | Jiang et al. |
| 7,659,395 | B2 | 2/2010 | Pajouhesh et al. |
| 7,662,795 | B2 | 2/2010 | Rodriguez et al. |
| 7,691,962 | B2 | 4/2010 | Boyd et al. |
| 7,696,185 | B2 | 4/2010 | Berkman |
| 7,713,944 | B2 | 5/2010 | Kinberger et al. |
| 7,740,847 | B2 | 6/2010 | Allan et al. |
| 7,767,202 | B2 | 8/2010 | Pardoll et al. |
| 7,767,803 | B2 | 8/2010 | Diener et al. |
| 7,794,929 | B2 | 9/2010 | Baylin et al. |
| 7,862,798 | B2 | 1/2011 | Leamon et al. |
| 7,872,235 | B2 | 1/2011 | Rousso et al. |
| 7,875,586 | B2 | 1/2011 | Kovbasnjuk et al. |
| 7,879,981 | B2 | 2/2011 | Obata |
| 7,910,594 | B2 | 3/2011 | Mahov et al. |
| 7,990,533 | B2 | 8/2011 | Maier et al. |
| 8,000,773 | B2 | 8/2011 | Rousso et al. |
| 8,013,991 | B2 | 9/2011 | Maier et al. |
| 8,088,387 | B2 | 1/2012 | Steeves et al. |
| 8,101,369 | B2 | 1/2012 | Nam et al. |
| 8,101,713 | B2 | 1/2012 | Cuello et al. |
| 8,105,568 | B2 | 1/2012 | Vlahov et al. |
| 8,211,402 | B2 | 3/2012 | Babich et al. |
| 8,153,595 | B2 | 4/2012 | Chen |
| 8,194,660 | B2 | 6/2012 | Birze et al. |
| 8,211,401 | B2 | 7/2012 | Babich et al. |
| 8,211,473 | B2 | 7/2012 | Troiano et al. |
| 8,211,635 | B2 | 7/2012 | Barton |
| 8,227,634 | B2 | 7/2012 | Pomper et al. |
| 8,236,330 | B2 | 8/2012 | Zale et al. |
| 8,246,968 | B2 | 8/2012 | Zale et al. |
| 8,258,111 | B2 | 9/2012 | Shen et al. |
| 8,273,363 | B2 | 9/2012 | Zale et al. |
| 8,313,728 | B2 | 11/2012 | Leamon et al. |
| 8,388,977 | B2 | 3/2013 | Low et al. |
| 8,394,922 | B2 | 3/2013 | Cheng et al. |
| 8,404,817 | B2 | 3/2013 | Sherman et al. |
| 8,414,864 | B2 | 4/2013 | Cappelletti et al. |
| 8,414,898 | B2 | 4/2013 | Afar et al. |
| 8,445,851 | B2 | 5/2013 | Rousso et al. |
| 8,450,290 | B2 | 5/2013 | Worm et al. |
| 8,465,725 | B2 | 6/2013 | Babich et al. |
| 8,487,128 | B2 | 7/2013 | Babich et al. |
| 8,487,129 | B2 | 7/2013 | Babich et al. |
| 8,491,896 | B2 | 7/2013 | Goldenberg et al. |
| 8,507,434 | B2 | 8/2013 | Popel et al. |
| 8,557,772 | B2 | 10/2013 | Popel et al. |
| 8,565,945 | B2 | 10/2013 | Babich et al. |
| 8,603,499 | B2 | 12/2013 | Zale et al. |
| 8,603,500 | B2 | 12/2013 | Zale et al. |
| 8,603,501 | B2 | 12/2013 | Zale et al. |
| 8,606,349 | B2 | 12/2013 | Rousso et al. |
| 8,644,910 | B2 | 2/2014 | Rousso et al. |
| 8,685,416 | B2 | 4/2014 | Klinman et al. |
| 8,685,891 | B2 | 4/2014 | Muraca |
| 8,703,918 | B2 | 4/2014 | Colombatti et al. |
| 8,709,483 | B2 | 4/2014 | Farokhzad et al. |
| 8,772,226 | B2 | 6/2014 | Denmeade et al. |
| 8,772,459 | B2 | 6/2014 | Ho et al. |
| 8,778,305 | B2 | 7/2014 | Pomper et al. |
| 8,802,153 | B2 | 8/2014 | Cheng et al. |
| 8,816,095 | B2 | 8/2014 | Brown et al. |
| 8,834,842 | B2 | 9/2014 | Leamon et al. |
| 8,840,865 | B2 | 9/2014 | Babich et al. |
| 8,852,630 | B2 | 10/2014 | Spiegel et al. |
| 8,858,509 | B2 | 10/2014 | Spiegel et al. |
| 8,865,126 | B2 | 10/2014 | Leamon et al. |
| 8,865,875 | B2 | 10/2014 | Liu et al. |
| 8,877,970 | B2 | 11/2014 | Zimmerman et al. |
| 8,901,294 | B2 | 12/2014 | Kim et al. |
| 8,907,058 | B2 | 12/2014 | Low et al. |
| 8,916,161 | B2 | 12/2014 | Buckley |
| 8,916,167 | B2 | 12/2014 | Low et al. |
| 8,921,378 | B2 | 12/2014 | Toermakaengas et al. |
| 8,926,944 | B2 | 1/2015 | Babich et al. |
| 8,926,945 | B2 | 1/2015 | Port et al. |
| 8,940,871 | B2 | 1/2015 | Wu et al. |
| 8,946,388 | B2 | 2/2015 | Sahin et al. |
| 8,962,799 | B2 | 2/2015 | Babich et al. |
| 8,986,655 | B2 | 3/2015 | Weiss et al. |
| 8,987,319 | B2 | 3/2015 | Miller |
| 9,006,415 | B2 | 4/2015 | Ren et al. |
| 9,029,340 | B2 | 5/2015 | Lupold et al. |
| 9,044,468 | B2 | 6/2015 | Pomper et al. |
| 9,056,841 | B2 | 6/2015 | Pomper et al. |
| 9,074,000 | B2 | 7/2015 | Scheinberg et al. |
| 9,120,837 | B2 | 9/2015 | Babich et al. |
| 9,123,725 | B2 | 9/2015 | Cho et al. |
| 9,180,203 | B2 | 11/2015 | Cui et al. |
| 9,180,214 | B1 | 11/2015 | Miao |
| 9,193,763 | B2 | 11/2015 | Low et al. |
| 9,216,218 | B2 | 12/2015 | Sahin et al. |
| 9,226,981 | B2 | 1/2016 | Pomper et al. |
| 9,242,012 | B2 | 1/2016 | Ma et al. |
| 9,255,262 | B2 | 2/2016 | Wong et al. |
| 9,278,067 | B2 | 3/2016 | Boulikas |
| 9,295,727 | B2 | 3/2016 | Zale et al. |
| 9,309,193 | B2 | 4/2016 | Babich et al. |
| 9,346,846 | B1 | 5/2016 | Herzon et al. |
| 9,371,360 | B2 | 6/2016 | Pomper et al. |
| 9,387,344 | B2 | 7/2016 | Sgouros et al. |
| 9,422,234 | B2 | 8/2016 | Chandran et al. |
| 9,429,575 | B2 | 8/2016 | Ban et al. |
| 9,433,594 | B2 | 9/2016 | Babich et al. |
| 9,447,121 | B2 | 9/2016 | Babich et al. |
| 9,498,546 | B2 | 11/2016 | Pomper et al. |
| 9,556,167 | B2 | 1/2017 | Spiegel et al. |
| 9,567,402 | B2 | 2/2017 | Liu |
| 9,580,467 | B2 | 2/2017 | Cheng et al. |
| 9,580,474 | B2 | 2/2017 | Viscidi et al. |

(56) References Cited

U.S. PATENT DOCUMENTS

| | | |
|---|---|---|
| 9,585,957 B2 | 3/2017 | Powell et al. |
| 9,617,602 B2 | 4/2017 | Joseph et al. |
| 9,636,413 B2 | 5/2017 | Vlahov et al. |
| 9,687,572 B2 | 6/2017 | Babich et al. |
| 9,717,484 B2 | 8/2017 | Kalloo et al. |
| 9,745,380 B2 | 8/2017 | Govindan et al. |
| 9,757,084 B2 | 9/2017 | Sgouros et al. |
| 9,764,039 B2 | 9/2017 | Thanos et al. |
| 9,770,467 B2 | 9/2017 | Dubensky, Jr. et al. |
| 9,770,517 B2 | 9/2017 | Govindan et al. |
| 9,801,956 B2 | 10/2017 | Kularatne et al. |
| 9,808,516 B2 | 11/2017 | Brockstedt et al. |
| 9,808,538 B2 | 11/2017 | Kularatne et al. |
| 9,814,759 B2 | 11/2017 | Wong et al. |
| 9,861,444 B2 | 1/2018 | Kalloo et al. |
| 9,889,199 B2 | 2/2018 | Basilion |
| 9,932,411 B2 | 4/2018 | Terrett et al. |
| 9,951,049 B2 | 4/2018 | Kamal et al. |
| 9,951,324 B2 | 4/2018 | Low et al. |
| 9,956,305 B2 | 5/2018 | Babich et al. |
| 9,968,691 B2 | 5/2018 | Kularatne et al. |
| 9,988,407 B2 | 6/2018 | Slusher et al. |
| 10,010,624 B2 | 7/2018 | Howard et al. |
| 10,011,632 B2 | 7/2018 | Wang et al. |
| 10,016,519 B2 | 7/2018 | Kopka et al. |
| 10,029,023 B2 | 7/2018 | Pomper et al. |
| 10,046,054 B2 | 8/2018 | Low et al. |
| 10,064,957 B2 | 9/2018 | Govindan et al. |
| 10,308,606 B2 | 6/2019 | Kularatne et al. |
| 10,363,388 B2 | 7/2019 | Fonseca et al. |
| 10,398,791 B2 * | 9/2019 | Eder .................. A61K 51/0497 |
| 10,406,240 B2 | 9/2019 | Low et al. |
| 10,456,482 B2 | 10/2019 | Kularatne et al. |
| 10,471,160 B2 * | 11/2019 | Eder .................. C07B 59/002 |
| 10,485,878 B2 | 11/2019 | Low et al. |
| 10,517,956 B2 | 12/2019 | Low et al. |
| 10,517,957 B2 | 12/2019 | Low et al. |
| 10,624,959 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,688,200 B2 | 6/2020 | Kung et al. |
| 10,828,282 B2 | 11/2020 | Low et al. |
| 11,045,564 B2 * | 6/2021 | Eder .................. A61K 51/0482 |
| 2003/0049203 A1 | 3/2003 | Elmaleh et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0002587 A1 | 1/2004 | Watkins et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0092890 A1 | 5/2004 | Ash |
| 2004/0110723 A1 | 6/2004 | Frangioni |
| 2004/0146516 A1 | 7/2004 | Roben et al. |
| 2004/0213791 A1 | 10/2004 | Bander et al. |
| 2004/0242582 A1 | 12/2004 | Green et al. |
| 2005/0002942 A1 | 1/2005 | Mahov et al. |
| 2005/0069889 A1 | 3/2005 | Nihei et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic |
| 2005/0245486 A1 | 11/2005 | Frangioni |
| 2005/0255042 A1 | 11/2005 | Lam et al. |
| 2006/0024317 A1 | 2/2006 | Boyd et al. |
| 2006/0045883 A1 | 3/2006 | Molldrem et al. |
| 2006/0051380 A1 | 3/2006 | Schulick et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0148741 A1 | 7/2006 | Barrett et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020177 A1 | 1/2007 | McGill et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0141052 A1 | 6/2007 | Watkins et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0190029 A1 | 8/2007 | Pardoll et al. |
| 2007/0212337 A1 | 9/2007 | Bedi et al. |
| 2007/0219165 A1 | 9/2007 | Berkman et al. |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008649 A1 | 1/2008 | Cappelletti et al. |
| 2008/0008719 A1 | 1/2008 | Bowdish et al. |
| 2008/0089842 A1 | 4/2008 | Pagel et al. |
| 2008/0089869 A1 | 4/2008 | Denmeade et al. |
| 2008/0089892 A1 | 4/2008 | Allan et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214154 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmeran et al. |
| 2009/0214636 A1 | 8/2009 | Low et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0047170 A1 | 2/2010 | Denmeade et al. |
| 2010/0048490 A1 | 2/2010 | Vlahov et al. |
| 2010/0055735 A1 | 3/2010 | Low et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0234450 A1 | 9/2010 | Schultz et al. |
| 2010/0240701 A1 | 9/2010 | Mahov et al. |
| 2010/0260677 A1 | 10/2010 | Bhatia et al. |
| 2010/0324008 A1 | 12/2010 | Low et al. |
| 2011/0008253 A1 | 1/2011 | Babich et al. |
| 2011/0027180 A1 | 2/2011 | Magnani |
| 2011/0027274 A1 | 2/2011 | Cheng et al. |
| 2011/0064657 A1 | 3/2011 | Pomper et al. |
| 2011/0124948 A1 | 5/2011 | Yokell |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0256157 A1 | 10/2011 | Howard et al. |
| 2011/0288152 A1 | 11/2011 | Low et al. |
| 2011/0305768 A1 | 12/2011 | Mao et al. |
| 2012/0009121 A1 | 1/2012 | Pomper et al. |
| 2012/0276162 A1 | 11/2012 | Zale et al. |
| 2012/0322741 A1 | 12/2012 | Low et al. |
| 2013/0034494 A1 | 2/2013 | Babich et al. |
| 2013/0302409 A1 | 11/2013 | Fuchs et al. |
| 2013/0336888 A1 | 12/2013 | Babich et al. |

(56) References Cited

U.S. PATENT DOCUMENTS

| | | |
|---|---|---|
| 2014/0073763 A1 | 3/2014 | Low et al. |
| 2014/0107316 A1 | 4/2014 | Mahov et al. |
| 2014/0113322 A1 | 4/2014 | Cui et al. |
| 2014/0140925 A1 | 5/2014 | Eamon et al. |
| 2014/0154702 A1 | 6/2014 | Parker et al. |
| 2014/0187501 A1 | 7/2014 | Bilodeau et al. |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0110716 A1 | 4/2015 | Armor |
| 2015/0246144 A1 | 9/2015 | Pomper et al. |
| 2015/0297735 A1 | 10/2015 | Mahov et al. |
| 2015/0315196 A1 | 11/2015 | Howard |
| 2015/0366968 A1 | 12/2015 | Basilion et al. |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0235865 A1 | 8/2016 | Pomper et al. |
| 2016/0361376 A1 | 12/2016 | Mahov et al. |
| 2016/0361432 A1 | 12/2016 | Mahov et al. |
| 2016/0361433 A1 | 12/2016 | Mahov et al. |
| 2017/0081298 A1 | 3/2017 | Ray et al. |
| 2017/0151356 A1 | 6/2017 | Govindan et al. |
| 2017/0218464 A1 | 8/2017 | Pomper et al. |
| 2017/0224709 A1 | 8/2017 | Slusher et al. |
| 2017/0226141 A1 | 8/2017 | Slusher et al. |
| 2017/0258923 A1 | 9/2017 | Low et al. |
| 2017/0266316 A1 | 9/2017 | Govindan et al. |
| 2017/0275673 A1 | 9/2017 | Luo et al. |
| 2017/0281789 A1 | 10/2017 | Basilion et al. |
| 2017/0281791 A1 | 10/2017 | Govindan et al. |
| 2017/0333576 A1 | 11/2017 | Pomper et al. |
| 2018/0008668 A1 | 1/2018 | Isaacs et al. |
| 2018/0051039 A1 | 2/2018 | Pomper et al. |
| 2018/0064831 A1 | 3/2018 | Basilion et al. |
| 2018/0111895 A1 | 4/2018 | Babich et al. |
| 2018/0118847 A1 | 5/2018 | Bander |
| 2018/0133296 A1 | 5/2018 | Barrett et al. |
| 2018/0148480 A1 | 5/2018 | Issaacs et al. |
| 2018/0185511 A1 | 7/2018 | Woodworth et al. |
| 2018/0207299 A1 | 7/2018 | Babich et al. |
| 2018/0243431 A1 | 8/2018 | Low et al. |
| 2018/0256737 A1 | 9/2018 | Mahov et al. |
| 2018/0258134 A1 | 9/2018 | Wang et al. |
| 2018/0271988 A1 | 9/2018 | Low et al. |
| 2018/0271989 A1 | 9/2018 | Low et al. |
| 2018/0271990 A1 | 9/2018 | Low et al. |
| 2018/0289827 A1 | 10/2018 | Low et al. |
| 2018/0289828 A1 | 10/2018 | Low et al. |
| 2018/0289829 A1 | 10/2018 | Low et al. |
| 2018/0303950 A1 | 10/2018 | Low et al. |
| 2018/0339071 A1 | 11/2018 | Jeong et al. |
| 2018/0346008 A1 | 12/2018 | Nahum et al. |
| 2019/0177345 A1 | 6/2019 | Larsen |
| 2019/0389951 A1 | 12/2019 | Murphy et al. |
| 2020/0155695 A1 | 5/2020 | Low et al. |
| 2020/0155696 A1 | 5/2020 | Low et al. |
| 2020/0188523 A1 | 6/2020 | Low et al. |
| 2020/0261592 A1 | 8/2020 | Low et al. |
| 2020/0297701 A1 | 9/2020 | Low et al. |
| 2021/0077468 A1 | 3/2021 | Low et al. |

FOREIGN PATENT DOCUMENTS

| | | |
|---|---|---|
| CA | 2696627 A1 | 2/2009 |
| CA | 2924360 A1 | 4/2015 |
| CN | 1662263 A | 8/2005 |
| CN | 101863924 A | 10/2010 |
| CN | 102014956 A | 4/2011 |
| CN | 104873982 A | 9/2015 |
| DE | 202014008232 U1 | 3/2015 |
| EP | 0116208 A1 | 8/1984 |
| EP | 1177200 A1 | 6/2005 |
| EP | 1472541 B1 | 9/2009 |
| EP | 2187965 A1 | 5/2010 |
| EP | 2318366 A2 | 5/2011 |
| EP | 2136788 B1 | 10/2011 |
| EP | 2373621 A1 | 10/2011 |
| EP | 2373621 A2 | 10/2011 |
| EP | 2373622 A2 | 10/2011 |
| EP | 2389361 A2 | 11/2011 |
| EP | 2408755 A2 | 1/2012 |
| EP | 1999136 B1 | 10/2012 |
| EP | 2644192 A1 | 10/2013 |
| EP | 2644594 A1 | 10/2013 |
| EP | 2648766 A1 | 10/2013 |
| EP | 2436376 B1 | 7/2014 |
| EP | 2759535 A1 | 7/2014 |
| EP | 2240171 B1 | 8/2014 |
| EP | 2170075 A1 | 12/2014 |
| EP | 2823826 A2 | 1/2015 |
| EP | 2097111 B1 | 7/2015 |
| EP | 2921482 A2 | 9/2015 |
| EP | 2938364 A1 | 11/2015 |
| EP | 2942065 A1 | 11/2015 |
| EP | 2958596 A1 | 12/2015 |
| EP | 2706057 B1 | 4/2016 |
| EP | 3038996 A1 | 7/2016 |
| EP | 3388086 A1 | 10/2018 |
| IL | 203998 A | 8/2015 |
| JP | 2002506204 A | 2/2002 |
| JP | 2004536034 A | 12/2004 |
| JP | 2005274569 A | 10/2005 |
| JP | 2006501149 A | 1/2006 |
| JP | 2006518712 A | 8/2006 |
| JP | 2007521803 A | 8/2007 |
| JP | 2010532754 A | 10/2010 |
| JP | 2010-536790 A | 12/2010 |
| JP | 2012511023 A | 5/2012 |
| JP | 2014-221779 A | 11/2014 |
| JP | 2016-153410 A | 8/2016 |
| JP | 2016-535013 A | 11/2016 |
| JP | 2018-058847 A | 4/2018 |
| JP | 2018-058864 A | 4/2018 |
| JP | 2018-150350 A | 9/2018 |
| JP | 6556805 B2 | 8/2019 |
| JP | 2020-073472 A | 5/2020 |
| NO | 2018/191376 A2 | 10/2018 |
| WO | 8801622 A1 | 3/1988 |
| WO | 9107418 A1 | 4/1991 |
| WO | 9533766 A1 | 12/1995 |
| WO | 9945374 A2 | 9/1999 |
| WO | 2000064911 A1 | 11/2000 |
| WO | 2000066091 A1 | 11/2000 |
| WO | 2002043773 A2 | 2/2002 |
| WO | 2002062398 A2 | 8/2002 |
| WO | 2002098885 A1 | 12/2002 |
| WO | 2003060523 A1 | 7/2003 |
| WO | 03092742 A1 | 11/2003 |
| WO | 2003092742 A1 | 11/2003 |
| WO | 2003097647 A1 | 11/2003 |
| WO | 2004010957 A2 | 2/2004 |
| WO | 2004069159 A2 | 8/2004 |
| WO | 2004069285 A1 | 8/2004 |
| WO | 2005082023 A2 | 9/2005 |
| WO | 2005/112919 A2 | 12/2005 |
| WO | 2006012527 A1 | 2/2006 |
| WO | 2006093991 A1 | 9/2006 |
| WO | 2006096754 A2 | 9/2006 |
| WO | 2006136564 A1 | 12/2006 |
| WO | 2007/022493 A2 | 2/2007 |
| WO | 2007022494 A2 | 2/2007 |
| WO | 2007/042504 A2 | 4/2007 |
| WO | 2007106869 A1 | 9/2007 |
| WO | 2008057437 A2 | 5/2008 |
| WO | 2008058192 A2 | 5/2008 |
| WO | 2008101231 A2 | 8/2008 |
| WO | 2008121949 A1 | 10/2008 |
| WO | 2009002529 A2 | 12/2008 |
| WO | 2009026177 A1 | 2/2009 |
| WO | 2009082606 A2 | 2/2009 |

(56) References Cited

FOREIGN PATENT DOCUMENTS

| | | |
|---|---|---|
| WO | 2009070302 A1 | 6/2009 |
| WO | 2009002529 A2 | 12/2009 |
| WO | 2009002993 A1 | 12/2009 |
| WO | 2010014933 A2 | 2/2010 |
| WO | 2010065899 A2 | 6/2010 |
| WO | 2010065902 A2 | 6/2010 |
| WO | 2010065906 A2 | 6/2010 |
| WO | 2010108125 A2 | 9/2010 |
| WO | 2011014821 A1 | 2/2011 |
| WO | 2010108125 A3 | 3/2011 |
| WO | 2011106639 A1 | 9/2011 |
| WO | 2011108125 A2 | 9/2011 |
| WO | 2012078534 A1 | 6/2012 |
| WO | 2012/174136 A1 | 12/2012 |
| WO | 2012166923 A2 | 12/2012 |
| WO | 2013/022797 A1 | 2/2013 |
| WO | 2013022797 A1 | 2/2013 |
| WO | 2013028664 A1 | 2/2013 |
| WO | 2013130776 A1 | 9/2013 |
| WO | 2014078484 A1 | 5/2014 |
| WO | 2014106208 A1 | 7/2014 |
| WO | 2014127365 A1 | 8/2014 |
| WO | 2014134543 A1 | 9/2014 |
| WO | 2015/055318 A1 | 4/2015 |
| WO | 2015053318 A1 | 4/2015 |
| WO | 2015055318 A1 | 4/2015 |
| WO | 2015057250 A1 | 4/2015 |
| WO | 2015/075515 A1 | 5/2015 |
| WO | 2015171792 A1 | 11/2015 |
| WO | 2016030329 A1 | 3/2016 |
| WO | 2016040179 A1 | 3/2016 |
| WO | 2017/116994 A1 | 7/2017 |
| WO | 2018/191376 A2 | 10/2018 |
| WO | 2019/165200 A1 | 8/2019 |

OTHER PUBLICATIONS

Supplementary Partial European Search Report for counterpart European Application No. 14861854.9, mailed May 19, 2017.
International Preliminary Examination Report received in related application BR112016008319-9 dated Jan. 12, 2021.
First Examination Report for counterpart Saudi Arabian Application No. 516370842, with English translation.
Extended European Search Report for European U.S. Appl. No. 18/175,078, dated Sep. 14, 2018.
Office Action for counterpart Indonesia Patent Application No. P00201603202, dated Jan. 28, 2019 (with English Translation).
Office Action for counterpart Mexican Patent Application No. MX/a/2016/005013, dated Apr. 24, 2019 (waiting on English Translation).
Search Report for Counterpart European U.S. Appl. No. 18/184,296, dated Jan. 23, 2019.
Search Report for Counterpart European Application No. 18203547.7, dated Apr. 4, 2019.
Office Action for counterpart Japanese Patent Application No. 2018-193272, dated Jul. 16, 2019 (with English Translation).
Search Report for Counterpart European Application No. 18184296.4, dated Feb. 12, 2019.
McBride, William J., et al., "Radiofluorination Using Aluminum-Floride (Al18F)," Ejnmmi Research, 2013, 3:36, http://www.ejnmmires.com/content/3/1/36, 11 pages.
Jeong, Jae Min et al., "Preparation of a Promising Angiogenesis PET Imaging Agent: 68Ga-Labeled c(RGDyK)-Isothiocyanatobenzyl-1,4,7-Triazacyclononane-1,4,7-Triacetic Acid and Feasibility Studies in Mice," XP-002538417, The Journal of Nuclear Medicine, vol. 49, No. 5, May 2008, pp. 830-836.
Office Action for counterpart Japanese Patent Application No. 2018-208786, dated Oct. 1, 2019 (with English Translation).
Search Report for Counterpart European Application No. 19167560.2, dated Jul. 26, 2019.
Non-Final Office Action for counterpart Korean Application No. 10-2019-7003504, dated Oct. 29, 2019 (with English Translation).
Korean Examination Report for counterpart Application No. UAE/P/0390/2016, dated Dec. 15, 2019.
Korean Search Report for counterpart Application No. UAE/P/0390/2016, dated Dec. 15, 2019.
Philippines Office Action for counterpart PH Application No. 1-2016-500656, dated Jan. 10, 2020.
Second Substantive Examination for counterpart MX Application No. MX/a/2016/005013, dated Jan. 30, 2020.
Malaysian Office Action for counterpart MY Application No. PI 2016000645, dated Jan. 29, 2020.
Indonesian Office Action for counterpart Application No. P00201603202, dated Feb. 20, 2020.
Translation of Qatar Notice of Issuance of Examination Report for Application No. QA/201604/00130, dated Apr. 28, 2020.
Office Action received in related Japanese Patent Application No. 2019-128294 received from the Japanese Patent Office dated Jun. 9, 2020.
Eurasian Office Action for counterpart Patent Application No. 201690495/28 dated Jun. 29, 2020.
Georgia Office Action and Search Report for counterpart Patent Application No. AP 2014014132 dated Jul. 9, 2020.
Non Final Office Action for copending U.S. Appl. No. 16/510,495 dated Jul. 8, 2020.
Non Final Office Action for copending Application No. 16/551,198 dated Sep. 3, 2020.
Third Substantive Examination for counterpart MX Application No. MX/a/2016/005013, dated Aug. 26, 2020.
Supplementary Office Action in Philippines Application No. 1-2019-502571 dated Sep. 24, 2020.
First Office Action for counterpart Saudi Arabian Application No. 516370842 520411464with English Language Translation dated Nov. 24, 2020.
Vees, H., et al., "18F-choline and/or 11 C-acetate positron emission tomography: detection of residual or progressive subclinical disease at very low prostate-specific antigen values (<1 ng/mL) after radical prostatectomy," BJU Int, 2007, 99, 1415-1420.
Larson, S. M., et al., "Tumor Localization of 16β-18F-Fluoro-5a-Dihydrotestosterone Versus 18F-FDG in Patients with Progressive, Metastatic Prostate Cancer," J Nucl Med, 2004, 45, 366-373.
Schuster, D.M., et al., "Initial Experience with the Radiotracer Anti-1-Amino-3-18F-Fluorocyclobutane-1-Carboxylic Acid with PET/CT in Prostate Carcinoma," J. Nucl. Med., 2007, 48, 56-63.
Tehrani, O.S., et al., "Tumor Imaging Using 1-(2'-deoxy-2'-18F-Fluoro-β-D-Arabinofuranosyl) Thymine and PET," J. Nucl. Med., 2007, 48, 1436-1441.
Mease RC., et al., "N-[N-[(S)-1,3-Dicarboxypropyl]Carbamoyl]-4-[18F]Fluorobenzyl-LCysteine, [18F]DCFBC: A New Imaging Probe for Prostate Cancer," Clin. Cancer Res., 2008, 14, 3036-3043.
Zhou, J., et al., "NAAG Peptidase Inhibitors and Their Potential for Diagnosis and Therapy," Nat Rev Drug Discovery, 2005, 4, 1015-1026.
Schulke, N., et al., "The homodimer of prostate-specific membrane antigen is a functional target for cancer therapy," Proc. Natl. Acad. Sci., USA, 2003, 100, 12590-12595.
Nan, F., et al., "Dual Function Glutamate-Related Ligands: Discovery of a Novel, Potent Inhibitor of Glutamate Carboxypeptidase II Possessing mGluR3 Agonist Activity," J. Med. Chem., 2000, 43, 772-774.
Lange, P.H., "ProstaScint scan for staging prostate cancer," Urology, 2001, 57, 402-406.
Haseman, M.K.; et al., "Capromab Pendetide Imaging of Prostate Cancer," Cancer Biother Radiopharm, 2000, 15, 131-140.
Mier W., et al., "Conjugation of DOTA Using Isolated Phenolic Active Esters: The Labeling and Biodistribution of Albumin as Blood Pool Marker," Bioconjugate Chem., 2005, 16: 237-240.
Schafer et al., "A dimerized urea-based inhibitor of the prostate-specific membrane antigen for 68Ga-PET imaging of prostate cancer," EJNMMI Research, 2012, 2, 23, 11 pages.
Humblet, V. et al., "An HPLC/mass spectrometry platform for the development of multimodality contrast agents and targeted thera-

(56) References Cited

OTHER PUBLICATIONS peutics: prostate-specific membrane antigen small molecule derivatives," Contrast Media Mol. Imaging, 2006, 1, pp. 196-211.
Pomper, M.G., et al., "11C-MCG: synthesis, uptake selectivity, and primate PET of a probe for glutamate carboxypeptidase II (NAALADase)," Mol Imaging, 2002, 1, 96-101.
Silverman, "The Organic Chemistry of Drug Design and Drug Action," Elsevier Academic Press (2nd Ed. 2003).
PCT International Search Report and Written Opinion for PCT/US2011/026238, dated Apr. 27, 2011.
PCT International Search Report and Written Opinion for PCT/US2013/070007, dated Mar. 5, 2014.
C. Foss et al., Synthesis and Validation of a Novel Small-Molecule Fluorescent Probe for PSMA Expression in Human Tumor Neovasculature, Abstract ID: 362, Molecular Imaging, vol. 4, No. 3, p. 321, Jul. 2005.
PCT International Search Report for PCT/US2016/012653 dated Mar. 11, 2016.
PCT International Search Report/Written Opinion for PCT/US2009/061067, completed May 28, 2010.
PCT International Search Report/Written Opinion for PCT/US2009/061049, completed Mar. 15, 2010.
PCT Search Report & Written Opinion issued in App. No. PCT/US2014/065467, dated Apr. 15, 2015.
Office Action for counterpart Eurasian Patent Application No. 201690495, dated Dec. 20, 2018.
Office Action for counterpart Israel Patent Application No. 245113, dated Jan. 10, 2019.
Office Action for counterpart Georgian Patent Application No. AP 2014 014132, dated Jan. 11, 2019.
Office Action for counterpart Chilean Patent Application No. 00883-2016, dated Jan. 16, 2019 (with English Translation).
M. De Santis et al., "Role of Chemotherapy in Castration-Resistant Prostate Cancer." Der Urologe 1:39-43, 2012. (Eng. Translation).
A. Heidenreich, "Immunotherapy for Metastic Prostate Cancer—Do we really need this." Der Urologe 1(1):32-38, 2012. (Eng. Translation).
T.H. Kuru et al., "MRI Navigated Stereotactic Prostate Biopsy." Der Urologe 1(1):50-56, 2012. (Eng. Translation).
F. Moltzahn et al., " Bone Metastasis in Prostate Cancer." Der Urologe 1(1):20-26, 2012. (Eng. Translation).
A. Omlin et al., "Inhibitors of Androgen and Estrogen Biosynthesis in Castration-Resistant Prostate Cancer." Der Urologe 1(1):8-14, 2012. (Eng. Translation).
S.N. Reske et al., "Advancement of PET and PET/CT in Prostate Carcinoma." Der Urologe 45(6):707-714, 2006. (Eng. Translation).
S.N. Reske et al., "Nuclear Imaging of Prostate Cancer." Urologe 46(11):1485-1499, 2007. (Eng. Translation).
S.N. Reske et al., "PET and PET/CT in Relapsing Prostate Carcinoma," Der Urologe 45(10): 1240, 1242-4, 1246-8, 1250, 2006. (Eng. Translation).
M. Spahn et al., "How Should Hormone Therapy for Castration-Resistant Cancer be Continued?" Der Urologe 51 (1):15-19, 2012. (Eng. Translation).
G. Thalmann, "Advanced Prostate Cancer." Der Urologe 51(1):7, 2012. (Eng. Translation).
L. Weissbach, "Which Components Should "Living Guidelines" Contain?" Der Urologe 51(1):57-59, 2012. (Eng. Translation).
S. Preusser et al., "Castration-Resistant Prostate Cancer." Der Urologe 51(1):27-31, 2012. (Eng. Translation).
Y-q. Wu et al., "A Mild Deprotection Procedure for Tert-butyl Esters and Tert-butyl Ethers Using ZnBr2 in Methylene Chloride." Tetrahedron Letters 41, 2847-2849, 2000.
J. Meienhofer et al., "Solid-Phase Systhesis with Attachment of Peptide to Resin Through an Amino Acid Side Chain: [8-Lysine]-Vasopressin," Proc. Nat. Acad. Sci., USA, vol. 68, No. 5, pp. 1006-1009, May 1971.
C. Dusich et al., General Approach for the Preparation of Fluorescent PSMA/GCPII Inhibitors, Abstract ID: 470 Poster board space: 29, Molecular Imaging, vol. 5, No. 3, pp. 322-323, Jul. 2006.

Oyama, N., Akino, H., Kanamaru, H., Suzuki, Y., Muramoto, S., Yonekura, Y., Sadato, N., Yamamoto, K., and Okada, K. (2002) 11C-acetate PET imaging of prostate cancer. J Nucl Med 43, 181-6.
Oyama, N., Kaneda, T., Nakai, M., Shioyama, R., Matsuta, Y., Tanase, K., Aoki, Y., Miwa, Y., Akino, H., Yokoyama, O., Okazawa, H., Fujibayashi, Y., and Yonekura, Y. (2006) [Pet imaging in prostate cancer]. Hinyokika Kiyo 52, 503-5.
Oyama, N., Miller, T. R., Dehdashti, F., Siegel, B. A., Fischer, K. C., Michalski, J. M., Kibel, A. S., Andriole, G. L., Picus, J., and Welch, M. J. (2003) 11C-acetate PET imaging of prostate cancer: detection of recurrent disease at PSA relapse. J Nucl Med 44, 549-55.
Parker, S. A., Diaz, I. L., Anderson, K. A., and Batt, C. A. (2013) Design, production, and characterization of a single-chain variable fragment (ScFv) derived from the prostate specific membrane antigen (PSMA) monoclonal antibody J591. Protein Expr Purif 89, 136-145.
Pavlicek, J., Ptacek, J., and Barinka, C. (2012) Glutamate carboxypeptidase II: an overview of structural studies and their importance for structure-based drug design and deciphering the reaction mechanism of the enzyme. Curr Med Chem 19, 1300-9.
Pavlicek, J., Ptacek, J., Cerny, J., Byun, Y., Skultetyova, L., Pomper, M. G., Lubkowski, J., and Barinka, C. (2014) Structural characterization of P1'-diversified urea-based inhibitors of glutamate carboxypeptidase II. Bioorg Med Chem Lett 24, 2340-5.
Perner, S., Hofer, M. D., Kim, R., Shah, R. B., Li, H., Moller, P., Hautmann, R. E., Gschwend, J. E., Kuefer, R., and Rubin, M. A. (2007) Prostate-specific membrane antigen expression as a predictor of prostate cancer progression. Hum Pathol 38, 696-701.
Pillarsetty, N., Punzalan, B., and Larson, S. M. (2009) 2-18F-Fluoropropionic acid as a PET imaging agent for prostate cancer. J Nucl Med 50, 1709-14.
Pinto, F., Totaro, A., Palermo, G., Calarco, A., Sacco, E., D'Addessi, A., Racioppi, M., Valentini, A., Gui, B., and Bassi, P. (2012) Imaging in prostate cancer staging: present role and future perspectives. Urol Int 88, 125-36.
Pomper, M. G., Musachio, J. L., Zhang, J., Scheffel, U., Zhou, Y., Hilton, J., Maini, A., Dannals, R. F., Wong, D. F., and Kozikowski, A. P. (2002) 11C-MCG: synthesis, uptake selectivity, and primate PET of a probe for glutamate carboxypeptidase II (NAALADase). Mol Imaging 1, 96-101.
Ponde, D. E., Dence, C. S., Oyama, N., Kim, J., Tai, Y. C., Laforest, R., Siegel, B. A., and Welch, M. J. (2007) 18F-fluoroacetate: a potential acetate analog for prostate tumor imaging-in vivo evaluation of 18F-fluoroacetate versus 11C-acetate. J Nucl Med 48, 420-8.
Poulsen, M. H., Bouchelouche, K., Gerke, O., Petersen, H., Svolgaard, B., Marcussen, N., Svolgaard, N., Ogren, M., Vach, W., Hoilund-Carlsen, P. F., Geertsen, U., and Walter, S. (2010) [18F]-fluorocholine positron-emission/computed tomography for lymph node staging of patients with prostate cancer: preliminary results of a prospective study. BJU Int 106, 639-43; discussion 644.
Poulsen, M. H., Bouchelouche, K., Hoilund-Carlsen, P. F., Petersen, H., Gerke, O., Steffansen, S. I., Marcussen, N., Svolgaard, N., Vach, W., Geertsen, U., and Walter, S. (2012) [18F]fluoromethylcholine (FCH) positron emission tomography/computed tomography (PET/CT) for lymph node staging of prostate cancer: a prospective study of 210 patients. BJU Int 110, 1666-71.
Preusser, S., Putora, P. M., Plasswilm, L., and Schmid, H. P. (2012) [Castration-resistant prostate cancer: surgical and radio-oncological therapeutic options]. Der Urologe. Ausg. A 51, 27-31.
Rais, R., Rojas, C., Wozniak, K., Wu, Y., Zhao, M., Tsukamoto, T., Rudek, M. A., and Slusher, B. S. (2014) Bioanalytical method for evaluating the pharmacokinetics of the GCP-II inhibitor 2-phosphonomethyl pentanedioic acid (2-PMPA). Journal of Pharmaceutical and Biomedical Analysis 88, 162-9.
Rajasekaran, S. A., Anilkumar, G., Oshima, E., Bowie, J. U., Liu, H., Heston, W., Bander, N. H., and Rajasekaran, A. K. (2003) A novel cytoplasmic tail MXXXL motif mediates the internalization of prostate-specific membrane antigen. Mol Biol Cell 14, 4835-45.
Ray Banerjee, S., Pullambhatla, M., Foss, C. A., Falk, A., Byun, Y., Nimmagadda, S., Mease, R. C., and Pomper, M. G. (2013) Effect of

(56) References Cited

OTHER PUBLICATIONS

Chelators on the Pharmacokinetics of Tc-Labeled Imaging Agents for the Prostate-Specific Membrane Antigen (PSMA). J Med Chem 56, 6108-21.

Ray Banerjee, S., Pullambhatla, M., Foss, C. A., Nimmagadda, S., Ferdani, R., Anderson, C. J., Mease, R. C., and Pomper, M. G. (2014) 64Cu-Labeled Inhibitors of Prostate-Specific Membrane Antigen for PET Imaging of Prostate Cancer. J Med Chem 57, 2657-69.

Reske, S. N. (2007) [Nuclear imaging of prostate cancer: current status]. Der Urologe. Aug. A 46, 1485-99.

Reske, S.N. (2008) [11C]Choline uptake with PET/CT for the initial diagnosis of prostate cancer: relation to PSA levels, tumour stage and anti-androgenic therapy. Eur J Nucl Med Mol Imaging 35(9):1740-1. doi: 10.1007/s00259-008-0839-5.

Reske, S. N., Blumstein, N. M., and Glatting, G. (2006) [Advancement of PET and PET/CT in prostate carcinoma]. Der Urologe. Ausg. A 45, 707-10, 712-4.

Reske, S. N., Blumstein, N. M., and Glatting, G. (2006) [PET and PET/CT in relapsing prostate carcinoma]. Der Urologe. Ausg. A 45, 1240, 1242-4, 1246-8, 1250.

Reske, S. N., Blumstein, N. M., and Glatting, G. (2008) [11C]choline PET/CT imaging in occult local relapse of prostate cancer after radical prostatectomy. Eur J Nucl Med Mol Imaging 35, 9-17.

Reske, S. N., Blumstein, N. M., Neumaier, B., Gottfried, H. W., Finsterbusch, F., Kocot, D., Moller, P., Glatting, G., and Perner, S. (2006) Imaging prostate cancer with 11C-choline PET/CT. J Nucl Med 47, 1249-54.

Rinnab, L., Mottaghy, F. M., Simon, J., Volkmer, B. G., de Petriconi, R., Hautmann, R. E., Wittbrodt, M., Egghart, G., Moeller, P., Blumstein, N., Reske, S., and Kuefer, R. (2008) [11C]Choline PET/CT for targeted salvage lymph node dissection in patients with biochemical recurrence after primary curative therapy for prostate cancer. Preliminary results of a prospective study. Urol Int 81, 191-7.

Rinnab, L., Simon, J., Hautmann, R. E., Cronauer, M. V., Hohl, K., Buck, A. K., Reske, S. N., and Mottaghy, F. M. (2009) [(11)C]choline PET/CT in prostate cancer patients with biochemical recurrence after radical prostatectomy. World J Urol 27, 619-25.

Rioja, J., Rodriguez-Fraile, M., Lima-Favaretto, R., Rincon-Mayans, A., Penuelas-Sanchez, I., Zudaire-Bergera, J. J., and Parra, R. O. (2010) Role of positron emission tomography in urological oncology. BJU Int 106, 1578-93.

Ristau, B. T., O'Keefe, D. S., and Bacich, D. J. (2014) The prostate-specific membrane antigen: Lessons and current clinical implications from 20 years of research. Urol Oncol 32, 272-279.

Roethke, M. C., Kuru, T. H., Afshar-Oromieh, A., Schlemmer, H. P., Hadaschik, B. A., and Fenchel, M. (2013) Hybrid positron emission tomography-magnetic resonance imaging with gallium 68 prostate-specific membrane antigen tracer: a next step for imaging of recurrent prostate cancer-preliminary results. Eur Urol 64, 862-4.

Taylor, R. M., Severns, V., Brown, D. C., Bisoffi, M., and Sillerud, L. O. (2012) Prostate cancer targeting motifs: expression of alphanu beta3, neurotensin receptor 1, prostate specific membrane antigen, and prostate stem cell antigen in human prostate cancer cell lines and xenografts. Prostate 72, 523-32.

Rong, S. B., Zhang, J., Neale, J. H., Wroblewski, J. T., Wang, S., and Kozikowski, A. P. (2002) Molecular modeling of the interactions of glutamate carboxypeptidase II with its potent NAAG-based inhibitors. J Med Chem 45, 4140-52.

Rothke, M. C., Afshar-Oromieh, A., and Schlemmer, H. P. (2013) [Potential of PET/MRI for diagnosis of prostate cancer]. Radiologe 53, 676-81.

Rybalov, M., Breeuwsma, A. J., Leliveld, A. M., Pruim, J., Dierckx, R. A., and de Jong, I. J. (2013) Impact of total PSA, PSA doubling time and PSA velocity on detection rates of (11)C-Choline positron emission tomography in recurrent prostate cancer. World J Urol 31, 319-23.

Sacha, P., Zamecnik, J., Barinka, C., Hlouchova, K., Vicha, A., Micochova, P., Hilgert, I., Eckschlager, T., and Konvalinka, J. (2007) Expression of glutamate carboxypeptidase II in human brain. Neuroscience 144, 1361-72.

Scattoni, V., Picchio, M., Suardi, N., Messa, C., Freschi, M., Roscigno, M., Da Pozzo, L., Bocciardi, A., Rigatti, P., and Fazio, F. (2007) Detection of lymph-node metastases with integrated [11C]choline PET/CT in patients with PSA failure after radical retropubic prostatectomy: results confirmed by open pelvic-retroperitoneal lymphadenectomy. Eur Urol 52, 423-9.

Schafer, M., Bauder-Wust, U., Leotta, K., Zoller, F., Mier, W., Haberkorn, U., Eisenhut, M., and Eder, M. (2012) A dimerized urea-based inhibitor of the prostate-specific membrane antigen for 68Ga-PET imaging of prostate cancer. EJNMMI Res 2, 23.

Scheffel, U., and Pomper, M. G. (2004) PET imaging of GRP receptor expression in prostate cancer. J Nucl Med 45, 1277-8.

Scher, B., and Seitz, M. (2008) PET/CT imaging of recurrent prostate cancer. Eur J Nucl Med Mol Imaging 35, 5-8.

Schulke, N., Varlamova, O. A., Donovan, G. P., Ma, D., Gardner, J. P., Morrissey, D. M., Arrigale, R. R., Zhan, C., Chodera, A. J., Surowitz, K. G., Maddon, P. J., Heston, W. D., and Olson, W. C. (2003) The homodimer of prostate- specific membrane antigen is a functional target for cancer therapy. Proc Natl Acad Sci U S A 100, 12590-5.

Shvarts, O., Han, K. R., Seltzer, M., Pantuck, A. J., and Belldegrun, A. S. (2002) Positron emission tomography in urologic oncology. Cancer Control 9, 335-42.

Silver, D. A., Pellicer, I., Fair, W. R., Heston, W. D., and Cordon-Cardo, C. (1997) Prostate-specific membrane antigen expression in normal and malignant human tissues. Clin Cancer Res 3, 81-5.

Simone, C. B., 2nd, and Hahn, S. M. (2013) What's in a Label? Radioimmunotherapy for metastatic prostate cancer. Clin Cancer Res 19, 4908-10.

Slusher, B. S., Tsai, G., Yoo, G., and Coyle, J. T. (1992) Immunocytochemical localization of the N-acetyl-aspartyl- glutamate (NAAG) hydrolyzing enzyme N-acetylated alpha-linked acidic dipeptidase (NAALADase). J Comp Neurol 315, 217-29.

Slusher, B. S., Vornov, J. J., Thomas, A. G., Hurn, P. D., Harukuni, I., Bhardwaj, A., Traystman, R. J., Robinson, M. B., Britton, P., Lu, X. C., Tortella, F. C., Wozniak, K. M., Yudkoff, M., Potter, B. M., and Jackson, P. F. (1999) Selective Inhibition of NAALADase, which converts NAAG to glutamate, reduces ischemic brain injury. Nat Med 5, 1396-402.

Soloviev, D., Fini, A., Chierichetti, F., Al-Nahhas, A., and Rubello, D. (2008) PET imaging with 11C-acetate in prostate cancer: a biochemical, radiochemical and clinical perspective. Eur J Nucl Med Mol Imaging 35, 942-9.

Spahn, M., and Krebs, M. (2012) [How should hormone therapy for castration-resistant prostate cancer be continued?]. Der Urologe. Ausg. A 51, 15-9.

Sweat, S. D., Pacelli, A., Murphy, G. P., and Bostwick, D. G. (1998) Prostate-specific membrane antigen expression is greatest in prostate adenocarcinoma and lymph node metastases. Urology 52, 637-40.

Tang, H., Brown, M., Ye, Y., Huang, G., Zhang, Y., Wang, Y., Zhai, H., Chen, X., Shen, T. Y., and Tenniswood, M. (2003) Prostate targeting ligands based on N-acetylated alpha-linked acidic dipeptidase. Biochem Biophys Res Commun 307, 8-14.

Tang, Q. L., and Yao, M. Y. (2008) [Updated application of prostate-specific membrane antigen to the diagnosis and treatment of prostate cancer]. Zhonghua Nan Ke Xue 14, 79-82.

International Preliminary Report received from the Brazilian Patent Office in related Brazilian Application No. BR112016008319-9 dated Jan. 12, 2021.

Office Action for counterpart Peru Application No. 000519-2016/DIN dated Jan. 15, 2021.

Humblet, V. et al., "An HPLC/mass spectrometry platform for the development of multimodality contrast agents and targeted therapeutics: prostate-specific membrane antigen small molecule derivatives," Contrast Med. Mol. Imaging, 2006, 1, 196-211.

Japanese Office Action dated Mar. 23, 2017, which issued during prosecution of Japanese Application No. P016-524427.

(56) References Cited

OTHER PUBLICATIONS

Humblet, et al., "An HPLC/mass spectrometry platform for the development of multimodality contrast agents and targeted therapeutics: prostate-specific membrane antigen small molecule derivatives" Contrast Media & Molecular Imaging, Jul. 2006 1:196-211.
Eurasian Office Action dated Feb. 10, 2017, which issued during prosecution of Eurasian Application No. 201690495/28.
International Search Report dated Jan. 21, 2015, which issued during prosecution of International Application No. PCT/EP2014/002808.
Office Action for copending Eurasian Patent Application No. 201690495/28, dated Jul. 14, 2017.
Scher, B. et al., "Value of 11C-choline PET and PET/CT in patients with suspected prostate cancer," Eur. J. Nucl. Med. Mol. Imaging., 2007, 34, 45-53.
Tasch, J. et al., "A Unique Folate Hydrolase, Prostage-Specific Membrane Antingen (PSMA): A Target for Immunotherapy?" Crit. Rev. Immunol., 2001, 21, 249-261.
Rosenthal, S.A. et al., "Utility of Capromab Pendetide (ProstaScint) Imaging in the Management of Prostate Cancer," Tech Urol, 2001, 7, 27-37.
Wiberg et al. "A comparison of some properties of C=O and C=S bonds," ARKIVOC, 2011, (v) 45-56.
Zechmann, C. M., Afshar-Oromieh, A., Armor, T., Stubbs, J. B., Mier, W., Hadaschik, B., Joyal, J., Kopka, K., Debus, J., Babich, J. W., and Haberkorn, U. (2014) Radiation dosimetry and first therapy results with a I/ I-labeled small molecule (MIP-1095) targeting PSMA for prostate cancer therapy. Eur J Nucl Med Mol Imaging 41, 1280-92.
(2013) Abstracts of the Annual Congress of the European Association of Nuclear Medicine. October Oct. 19, 2023, 2013. Lyon, France. Eur J Nucl Med Mol Imaging 40 Suppl 2, S89-564.
Afshar-Oromieh, A., Avtzi, E., Giesel, F. L., Holland-Letz, T., Linhart, H. G., Eder, M., Eisenhut, M., Boxler, S., Hadaschik, B. A., Kratochwil, C., Weichert, W., Kopka, K., Debus, J., and Haberkorn, U. (2014) The diagnostic value of PET/CT imaging with the Ga-labelled PSMA ligand HBED-CC in the diagnosis of recurrent prostate cancer. Eur J Nucl Med Mol Imaging 42, 197-209.
Afshar-Oromieh, A., Haberkorn, U., Eder, M., Eisenhut, M., and Zechmann, C. M. (2012) [68Ga]Gallium-labelled PSMA ligand as superior PET tracer for the diagnosis of prostate cancer: comparison with 18F-FECH. Eur J Nucl Med Mol Imaging 39, 1085-6.
Afshar-Oromieh, A., Haberkorn, U., Hadaschik, B., Habl, G., Eder, M., Eisenhut, M., Schlemmer, H. P., and Roethke, M. C. (2013) PET/MRI with a 68Ga-PSMA ligand for the detection of prostate cancer. Eur J Nucl Med Mol Imaging 40, 1629-30.
Afshar-Oromieh, A., Haberkorn, U., Schlemmer, H. P., Fenchel, M., Eder, M., Eisenhut, M., Hadaschik, B. A., Kopp-Schneider, A., and Rothke, M. (2014) Comparison of PET/CT and PET/MRI hybrid systems using a 68Ga-labelled PSMA ligand for the diagnosis of recurrent prostate cancer: initial experience. Eur J Nucl Med Mol Imaging 41, 887-97.
Afshar-Oromieh, A., Malcher, A., Eder, M., Eisenhut, M., Linhart, H. G., Hadaschik, B. A., Holland-Letz, T., Giesel, F. L., Kratochwil, C., Haufe, S., Haberkorn, U., and Zechmann, C. M. (2013) PET imaging with a [(68)Ga]gallium-labelled PSMA ligand for the diagnosis of prostate cancer: biodistribution in humans and first evaluation of tumour lesions. Eur J Nucl Med Mol Imaging 40, 486-95.
Afshar-Oromieh, A., Zechmann, C. M., Malcher, A., Eder, M., Eisenhut, M., Linhart, H. G., Holland-Letz, T., Hadaschik, B. A., Giesel, F. L., Debus, J., and Haberkorn, U. (2014) Comparison of PET imaging with a (68)Ga-labelled PSMA ligand and (18)F-choline-based PET/CT for the diagnosis of recurrent prostate cancer. Eur J Nucl Med Mol Imaging 41, 11-20.
Aggarwal, S., Singh, P., Topaloglu, O., Isaacs, J. T., and Denmeade, S. R. (2006) A dimeric peptide that binds selectively to prostate-specific membrane antigen and inhibits its enzymatic activity. Cancer Res 66, 9171-7.
Alt, K., Wiehr, S., Ehrlichmann, W., Reischl, G., Wolf, P., Pichler, B. J., Elsasser-Beile, U., and Buhler, P. (2010) High-resolution animal PET imaging of prostate cancer xenografts with three different 64Cu-labeled antibodies against native cell-adherent PSMA. Prostate 70(13), 1413-21.
Ananias, H. J., van den Heuvel, M. C., Helfrich, W., and de Jong, I. J. (2009) Expression of the gastrin-releasing peptide receptor, the prostate stem cell antigen and the prostate-specific membrane antigen in lymph node and bone metastases of prostate cancer. Prostate 69(10), 1101-8.
Anderson, M. O., Wu, L. Y., Santiago, N. M., Moser, J. M., Rowley, J. A., Bolstad, E. S., and Berkman, C. E. (2007) Substrate specificity of prostate-specific membrane antigen. Bioorg Med Chem 15, 6678-86.
Antunes, A. A., Reis, S. T., Leite, K. R., Real, D. M., Sousa-Canavez, J. M., Camara-Lopes, L. H., Dall'Oglio, M. F., and Srougi, M. (2013) PGC and PSMA in prostate cancer diagnosis: tissue analysis from biopsy samples. International Braz J Urol : official journal of the Brazilian Society of Urology 39, 649-56.
Bacich, D. J., Pinto, J. T., Tong, W. P., and Heston, W. D. W. (2001) Cloning, expression, genomic localization, and enzymatic activities of the mouse homolog of prostate-specific membrane antigen/ NAALADase/folate hydrolase. Mammalian Genome 12, 117-123.
Baiz, D., Pinder, T. A., Hassan, S., Karpova, Y., Salsbury, F., Welker, M. E., and Kulik, G. (2012) Synthesis and characterization of a novel prostate cancer-targeted phosphatidylinositol-3-kinase inhibitor prodrug. J Med Chem 55, 8038-46.
Banerjee, S. R., Foss, C. A., Castanares, M., Mease, R. C., Byun, Y., Fox, J. J., Hilton, J., Lupold, S. E., Kozikowski, A. P., and Pomper, M. G. (2008) Synthesis and evaluation of technetium-99m- and rhenium-labeled inhibitors of the prostate-specific membrane antigen (PSMA). J Med Chem 51, 4504-17.
Banerjee, S. R., Pullambhatla, M., Byun, Y., Nimmagadda, S., Green, G., Fox, J. J., Horti, A., Mease, R. C., and Pomper, M. G. (2010) 68Ga-labeled inhibitors of prostate-specific membrane antigen (PSMA) for imaging prostate cancer. J Med Chem 53, 5333-41.
Banerjee, S. R., Pullambhatla, M., Shallal, H., Lisok, A., Mease, R. C., and Pomper, M. G. (2011) A Modular Strategy to Prepare Multivalent Inhibitors of Prostate-Specific Membrane Antigen (PSMA). Oncotarget 2, 1244-53.
Benesova, M., Schäfer, M., Bauder-Wust, U., Mier, W., Haberkorn, U., Eisenhut, M., Kopka, K., and Eder, M. (2013) Linker Modifications of DOTA-conjugated Inhibitors of the Prostate-Specific Membrane Antigen (PSMA). Eur J Nucl Med Mol Imaging 40, S281.
Ben Jemaa, A., Sallami, S., Ceraline, J., and Oueslati, R. (2013) A novel regulation of PSMA and PSA expression by Q640X Ar in 22Rv1 and LNCaP prostate cancer cells. Cell Biology International 37, 464-70.
Barinka, C., Byun, Y., Dusich, C. L., Banerjee, S. R., Chen, Y., Castanares, M., Kozikowski, A. P., Mease, R. C., Pomper, M. G., and Lubkowski, J. (2008) Interactions between human glutamate carboxypeptidase II and urea-based Inhibitors: structural characterization. J Med Chem 51, 7737-43.
Barinka, C., Rovenska, M., Mlcochova, P., Hlouchova, K., Plechanovova, A., Majer, P., Tsukamoto, T., Slusher, B. S., Konvalinka, J., and Lubkowski, J. (2007) Structural insight into the pharmacophore pocket of human glutamate carboxypeptidase II. J Med Chem 50, 3267-73.
Barinka, C., Starkova, J., Konvalinka, J., and Lubkowski, J. (2007) A high-resolution structure of ligand-free human glutamate carboxypeptidase II. Acta Crystallogr Sect F Struct Biol Cryst Commun 63, 150-3.
Barrett, J. A., Coleman, R. E., Goldsmith, S. J., Vallabhajosula, S., Petry, N. A., Cho, S., Armor, T., Stubbs, J. B., Maresca, K. P., Stabin, M. G., Joyal, J. L., Eckelman, W. C., and Babich, J. W. (2013) First-in-Man Evaluation of 2 High-Affinity PSMA-Avid Small Molecules for Imaging Prostate Cancer. J Nucl Med 54, 380-7.
Beheshti, M., Langsteger, W., and Fogelman, I. (2009) Prostate cancer: role of SPECT and PET in imaging bone metastases. Semin Nucl Med 39, 396-407.
Belloli, S., Jachetti, E., Moresco, R. M., Picchio, M., Lecchi, M., Valtorta, S., Freschi, M., Michelini, R. H., Bellone, M., and Fazio,

(56) References Cited

OTHER PUBLICATIONS

F. (2009) Characterization of preclinical models of prostate cancer using PET-based molecular imaging. Eur J Nucl Med Mol Imaging 36, 1245-55.
Ben Jemaa, A., Bouraoui, Y., Salami, S., Nouira, Y., and Oueslati, R. (2013) A comparison of the biological features of prostate cancer with (PSA+, PSMA+) profile according to RKIP. BioMed Research International 2013, 409179.
Bennett, V.J.,"Analysis of fluorescently labeled substance P analogs: binding, imaging and receptor activation," BMC Chemical Biology, 2001, 1:1. doi: 10.1186/1472-6769-1-1.
Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.
Cole et al., "Cancer theranostics: the rise of targeted magnetic nanoparticles," Trends in Biotechnology, 2011, 29, 323-332.
Davis, Mindy I., et al., "Crystal Structure of Prostate-Specific Membrane Antigen, A Tumor Marker and Peptidase", Apr. 26, 2005, PNAS, vol. 102, No. 17, pp. 5981-5986.
Definition of ligand, Random House Kernerman Webster's College Dictionary, downloaded on Jan. 25, 2014 from http://www. thefreedictionary. com/1 ligand, 1 page.
Eder et al., "68Ga-complex lipophilicity and the targeting property of a urea-based PSMA inhibitor for PET imaging," Bioconjugate Chemistry, 2012; 23:688-697.
Farokhzad, et al., "Nanoparticle-Aptamer Bioconjugates: A New Approach for Targeting Prostate Cancer Cells," Cancer Research 64, pp. 7668-7672 (2004).
Foss, Catherine A, et al. "Radiolabeled small-molecule ligands for JB prostate-specific membrane antigen: in vivo maging in experimental models of prostate cancer." Clinical cancer research 11.11 (2005): 4022:4028.
Gomez-Hens et al., "Long wavelength fluorophores: new trends in their analytical use," Trends in Analytical Chemistry, 2004; 23:127-136.
Henne, et al., "Synthesis and activity of a folate peptide camptothecin prodrug," ScienceDirect, Bioorganic & Medical Chemistry Letters 16 (2006) 5350-5355.
Hillier, Shawn M., et al., "Preclinical Evaluation of Novel Glutamate-Urea-Lysine Analogues That Target Prostate-Specific Membrane Antigen as Molecular Imaging Pharmaceuticals for Prostate Cancer," Cancer Res. Sep. 1, 2009 ;69(17):6932-40.
Jackson, Paul F., et al., "Design of NAALADase Inhibitors: A Novel Neuroprotective Strategy", 2001, Current Medicinal Chemistry, vol. 8, No. 8, pp. 949-957.
Jayaprakash, Sarva, et al. "Design and synthesis of a PSMA inhibitor-doxorubicin conjugate for targeted prostate cancer therapy." ChemMedChem 1.3 (2006): 299-302.
Kaur, G. et al., "Biological evaluation of tubulysin A: a potential anticancer and antiangiogenic natural product," Biochem. J., 2006, 396, 235-242.
Kozikowski, Alan P., et al., "Design of Remarkably Simple, Yet Potent Urea-Based Inhibitors of Glutamate Carbozypeptidase II (NAALADase)"2001, Journal of Medicinal Chemistry, vol. 44, No. 3, pp. 298-301.
Kozikowski, Alan P., et al., "Synthesis of Urea-Based Inhibitors as Active Site Probes of Glutamate Carboxypeptidase II: Efficacy as Analgesic Agents", 2004, Journal of Medicinal Chemistry, vol. 47, No. 7,pp. 1729-1738.
Kularatne et al., "Prostate-specific membrane antigen targeted imaging and therapy of prostate cancer using a PSMA Inhibitor as a homing ligand," Molecular Pharmaceutics, 6(3): 780-789 (2009).
Kularatne, S., "Synthesis and Biological Analysis of Prostate-Specific Membrane Antigen-Targeted Anticancer Prodrugs," J. Med. Chem, 2010, 53(21 ) , 7767-7777.
Larock, "Comprehensive Organic Transformations, a guide to functional group preparations," VCH Publishers, Inc. New York (1989).
Lu, G. et al., "Synthesis and SAR of 99mTc/Re-labeled small molecule prostate specific membrane antigen inhibitors with novel polar chelates, "Bioorganic and Medicinal Chemistry Letters, 2013, 23, 1557-1563.
Lupoid, et al., "Identification and characterization of nuclease-stabilized RNA molecules that bind human prostate cancer cells via the prostate-specific membrane antigen." Cancer Res. 2002; 62:4029-4033.
Majer, Pavel., et al., "Synthesis and Biological Evaluation of Thiol-Based Inhibitors of Glutamate Carboxypeptidase II: Discovery of an Orally Active GCP II Inhibitor", 2003, Journal of Medicinal Chemistry, vol. 46, No. 10, pp. 1989-1996.
Maresca, K. P., "A Series of Halogenated Heterodimeric Inhibitors of Prostate Specific Membrane Antigen (PSMA) as Radiolabeled Probes for Targeting Prostate Cancer," J. Med. Chem., 2009, 52 (2), pp. 347-357.
Maresca, K., et al., "Molecular targeting of prostate cancer with small molecule inhibitors of prostate specific membrane antigen (PSMA)," J. Nucl. Med. 2007, 48 (Supplement 2):25P.
Martin, et al., Helv. Chim. Acta, 78, 486-504 (1995) and Abstract.
McNamara et al., Cell type specific delivery of siRNAs with aptamer-siRNA chimeras, Nature Biotechnolgy, 2006; 24: 1005-1015.
Melby, et al., Cancer Research 53(8), pp. 1755-1760 (1993).
Mesters, et al., "Structure of Glutamate Carboxypeptidase II, a Drug Target in Neuronal Damage and Prostate Cancer"2, 006, The EMBO Journal, vol. 25, No. 6, pp. 1375-1384.
Olsnes, S., et al., Immunology Today, 10, pp. 291-295 (1989).
Paranjpe, et al., "Tumor-targeted bioconjugate based delivery of camptothecin: design, synthesis and in vitro evaluation," ScienceDirect Journal of Controlled Release 100 (2004) 275-292.
Pathalk et al., Enzymic protecting group techniques in organic synthesis, Stereosel. Biocatal. 775-797 (2000).
Peltier et al., "The Total Synthesis of Tubulysin D," J. Am. Chem. Soc. 128:16018-19 (2006).
Pubchem, Compound summary for: CID 58099954, Aug. 19, 2012.
Radioisotopes in Medicine, from http://www. word-nuclear.org/ information-library/non-power-nuclear applications/radioisotopes-research/radioisotopes-in-medicine.aspx, Dec. 28, 2016, pp. 1-20.
Ranasinghe, M. G., et al., "Facile Synthesis of Unsymmetrical Thiolsulfonates via Sulfonylation of Mercaptans", 1988, Synthetic Communications, vol. 18, No. 3, pp. 227-232.
Reddy et al., "PSMA-specific anti-tumor activity of the targeted-tubulysin conjugate, EC 1169," American Association for Cancer Research Annual Meeting (Apr. 8, 2013) Poster.
Reddy et al., "PSMA-specific anti-tumor activity of the targeted-tubulysin conjugate, EC 1169," American Association for Cancer Research Annual Meeting (Apr. 8, 2013) Presentation Abstract.
Roy, et al., "DUPA Conjugation of a Cytotoxic Indenoisoquinoline Topoisomerase I Inhibitor for Selective Prostate Cancer Cell Targeting, "J. Med. Chem. 58 (2015) 3094-3103.
Theodora E. Greene & Peter G.M. Wuts, "Protective Groups in Organic Synthesis," 2d edition, John Wiley & Sons, Inc. New York (1991).
Truffert, et al., Tetrahedron, 52:3005 (1996).
Vlahov, et al., "Design and regioselective synthesis of a new generation of targeted chemotherapeutics. Part 1: EC145, a folic acid conjugate of desacetylvinblastine monohydrazide," ScienceDirect, Bioorganic & Medical Chemistry Letters 16 (2006) 5093-5096.
Wang et al., "Prostate-Specific Membrane Antigen Targeted Tubulysin Conjugates for Cancer Therapy," 246th ACS National Meeting and Exposition (Sep. 8, 2013) Poster.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Benesova, M. et al., "Linker Modifications of DOTA-conjugated Inhibitors of the Prostate-Specific Membrane Antigen (PSMA)," poster, presented at the European Association of Nuclear Medicine Conference on Oct. 21, 2013.
Benesova, M. et al., "Linker Modifications of DOTA-conjugated Inhibitors of the Prostate-Specific Membrane Antigen (PSMA)," abstract, Eur. J. Nucl. Med. Mol. Imaging, available Oct. 16, 2013, 40, Suppl. 2, S 193.

(56) References Cited

OTHER PUBLICATIONS

Rinnab, L.; et al., "Evaluation of [11C]-choline positron-emission/computed tomography in patients with increasing prostate-specific antigen levels after primary treatment for prostate cancer," BJU Int, 2007, 100, 786,793.

Reske, S.N.; et al., "Imaging Prostate Cancer with 11C-Choline PET/CT," J Nucl Med, 2006, 47, 1249-1254.

Zophel, K.; Kotzerke, J, "Is 11C-choline the most appropriate tracer for prostate cancer?" Eur J Nucl Med Mol Imaging, 2004, 31, 756-759.

Vees, H.; et al., "18F-choline and/or 11C-acetate positron emission tomography: detection of residual or progressive subclinical disease at very low prostate-specific antigen values ( <1 ng/ml) after radical prostatectomy," BJU tnt, 2007, 99, 1415-1420.

Arson, S. M. et al., "Tumor Localization of 16β-18F-Fluoro-5a-Dihydrotestosterone Versus 18F-FDG in Patients with Progressive, Metastatic Prostate Cancer," J Nucl Med, 2004, 45, 366-373.

Indian Office Action for counterpart Application No. 201617011691, dated Nov. 9, 2021.

Testa, C., Schiavina, R., Lodi, R., Salizzoni, E., Corti, B., Farsad, M., Kurhanewicz, J., Manferrari, F., Brunocilla, E., Tonon, C., Monetti, N., Castellucci, P., Fanti, S., Coe, M., Grigioni, W. F., Martorana, G., Canini, R., and Barbiroli, B. (2007) Prostate cancer: sextant localization with MR imaging, MR spectroscopy, and 11C-choline PET/CT. Radiology 244, 797-806.

Thalmann, G. (2012) [Advanced prostate cancer: where are we going?]. Der Urologe. Ausg. A 51, 7.

Tykvart, J., Schimer, J., Barinkova, J., Pachl, P., Postova-Slavetinska, L., Majer, P., Konvalinka, J., and Sacha, P. (2014) Rational design of urea-based glutamate carboxypeptidase II (GCPII) inhibitors as versatile tools for specific drug targeting and delivery. Bioorg Med Chem 22, 4099-108.

Uprimny, C., Kroiss, A., Nilica, B., Buxbaum, S., Decristoforo, C., Horninger, W., and Virgolini, I. J. (2014) Ga-PSMA ligand PET versus F-NaF PET: evaluation of response to Ra therapy in a prostate cancer patient. Eur J Nucl Med Mol Imaging 42, 362-63.

Vallabhajosula, S., Smith-Jones, P. M., Navarro, V., Goldsmith, S. J., and Bander, N. H. (2004) Radioimmunotherapy of prostate cancer in human xenografts using monoclonal antibodies specific to prostate specific membrane antigen (PSMA): studies in nude mice. Prostate 58, 145-55.

Vavere, A. L., Kridel, S. J., Wheeler, F. B., and Lewis, J. S. (2008) 1-11C-acetate as a PET radiopharmaceutical for Imaging fatty acid synthase expression in prostate cancer. J Nucl Med 49, 327-34.

Vees, H., Buchegger, F., Albrecht, S., Khan, H., Husarik, D., Zaidi, H., Soloviev, D., Hany, T. F., and Miralbell, R. (2007) 18F-choline and/or 11C-acetate positron emission tomography: detection of residual or progressive subclinical disease at very low prostate-specific antigen values (<1 ng/ml) after radical prostatectomy. BJU Int 99, 1415-20.

Wang, H., Byun, Y., Barinka, C., Pullambhatla, M., Bhang, H. E., Fox, J. J., Lubkowski, J., Mease, R. C., and Pomper, M. G. (2010) Bioisosterism of urea-based GCPII inhibitors: Synthesis and structure-activity relationship studies. Bioorg Med Chem Lett 20, 392-7.

Wang, X., Huang, S. S., Heston, W. D., Guo, H., Wang, B. C., and Basilion, J. P. (2014) Development of targeted near-infrared imaging agents for prostate cancer. Mol Cancer Ther 13, 2595-606.

Weineisen, M., Simecek, J., Schottelius, M., Schwaiger, M., and Wester, H. J. (2014) Synthesis and preclinical evaluation of DOTAGA-conjugated PSMA ligands for functional imaging and endoradiotherapy of prostate cancer. EJNMMI Res 4, 63.

Weissbach, L. (2012) [Which components should living guidelines contain?]. Der Urologe. Ausg. A 51, 57-9.

Whitaker, H. C., Shiong, L. L., Kay, J. D., Gronberg, H., Warren, A. Y., Seipel, A., Wiklund, F., Thomas, B., Wiklund, P., Miller, J. L., Menon, S., Ramos-Montoya, A., Vowler, S. L., Massie, C., Egevad, L., and Neal, D. E. (2013) N-acetyl-L-aspartyl-L-glutamate peptidase-like 2 is overexpressed in cancer and promotes a pro-migratory and pro-metastatic phenotype. Oncogene 33, 5274-87.

Wiehr, S., Buhler, P., Gierschner, D., Wolf, P., Rolle, A. M., Kesenheimer, C., Pichler, B. J., and Elsasser-Beile, U. (2014) Pharmacokinetics and PET imaging properties of two recombinant anti-PSMA antibody fragments in comparison to their parental antibody. Prostate 74, 743-55.

Wu, L. Y., Anderson, M. O., Toriyabe, Y., Maung, J., Campbell, T. Y., Tajon, C., Kazak, M., Moser, J., and Berkman, C. E. (2007) The molecular pruning of a phosphoramidate peptidomimetic inhibitor of prostate-specific membrane antigen. Bioorg Med Chem 15, 7434-43.

Yamaguchi, T., Lee, J., Uemura, H., Sasaki, T., Takahashi, N., Oka, T., Shizukuishi, K., Endou, H., Kubota, Y., and Inoue, T. (2005) Prostate cancer: a comparative study of 11C-choline PET and MR imaging combined with proton MR spectroscopy. Eur J Nucl Med Mol Imaging 32, 742-8.

Zaheer, A., Cho, S. Y., and Pomper, M. G. (2009) New agents and techniques for imaging prostate cancer. J Nucl Med 50, 1387-90.

Zhang, A. X., Murelli, R. P., Barinka, C., Michel, J., Cocleaza, A., Jorgensen, W. L., Lubkowski, J., and Spiegel, D. A. (2010) A remote arene-binding site on prostate specific membrane antigen revealed by antibody-recruiting small molecules. J Am Chem Soc 132, 12711-6.

Zhang, Y., Guo, Z., Du, T., Chen, J., Wang, W., Xu, K., Lin, T., and Huang, H. (2012) Prostate specific membrane antigen (PSMA): A novel modulator of p38 for proliferation, migration, and survival in prostate cancer cells. Prostate 73, 835-41.

Zhou, J., Neale, J. H., Pomper, M. G., and Kozikowski, A. P. (2005) NAAG peptidase inhibitors and their potential for diagnosis and therapy. Nat Rev Drug Discov 4, 1015-26.

Silvola J. M.U. et al., "Al18F-NOTA-Folate Accumulates in Atherosclerotic Plaques and Can be Detected by PET/CT", Poster presented Nov. 7, 2015 in Orlando, FL at the 2015 American Heart Association Resuscitation Science Symposium (http://newsroom.heart.org/events/scientific-sessions-2015-newsroom-2942760). (3 pages).

Silvola J. M.U. et al., "Al18F-NOTA-Folate Accumulates in Atherosclerotic Plaques and Can be Detected by PET/CT", Published reference of poster, Nov. 10, 2015, at http://circ.ahajournals.org/content/132/Suppl_3/A18873?cited-by=yes&legid=circulationaha; 132/Suppl_3/A18873; Circulation, 2015; 132:A18873. (2 pages).

Viola-Villegas N., et al. "Targeting the Folate Receptor (FR): Imaging and Cytotoxicity of Rel Conjugates in FR-Overexpressing Cancer Cells," ChemMedChem, 2008 vol. 3, p. 1387-1394.

Chinese Patent Application No. 201480071245, by Endocyte, Inc et al.: Office Action, Dated Apr. 20, 2017 (9 pages).

Eurasian Patent Application No. 201690862/28, by Endocyte, Inc et al.: Office Action, Dated May 22, 2017; English Translation (2 pages).

European Patent Application No. EP 14861854, by Endocyte, Inc et al.: Partial Supplementary Search Report with Opinion; dated May 19, 2017 (15 pages).

First Office Action for counterpart Canadian Application No. 2924360, dated Jan. 11, 2018.

Second Office Action for counterpart Chinese Application No. 201480056250.5, dated Aug. 15, 2017.

Second Action for counterpart Eurasian Application No. 201690495/28, dated Feb. 10, 2017.

Second Office Action for counterpart Korean Application No. 1020167012314, dated Oct. 14, 2017.

Second Office Action for counterpart Georgian Application No. 1413201, dated Mar. 2018.

First Office Action for counterpart Georgian Application No. 1413201, dated Feb. 10, 2017.

First Examination Report for counterpart Chilean Application No. 00883-2016, dated Apr. 17, 2018.

Third Office Action for counterpart Korean Application No. 10-2016-7012314, dated May 2, 2018.

Afshar-Oromieh, A., et al., PET/MRI with a 68Ga-PSMA ligand for the detection of Prostrate Cancer, European Journal of Nuclear Medical Molecular Imaging (2013) 40:1629-1630.

Armor, T., et al., A comparison of 2D and 3D regions within the same patient to derive organ and tissue kinetics, Journal of Nuclear Medicine, May 2012, vol. 53, No. Supplement 1 13.

(56) References Cited

OTHER PUBLICATIONS

Eder, Matthias, et al., Pharmacokinetic Properties of Peptidic Radiopharmaceuticals: Reduced Uptake of (EH)3-Conjugates in Important Organs, J Nucl Med. Aug. 2013;54(8):1327-30. doi: 10.2967/jnumed.112.114512. Epub Jun. 26, 2013.
Istard Posters, Radionuclide Therapy & Dosimetry: Bone Pain Palliation, European Journal of Nuclear Medical Molecular Imaging (2012) 39 (Suppl 2): S304-S353.
Hillier, S., et al., [131I]MIP-1466, a small molecule prostate-specific membrane antigen (PSMA) inhibitor for targeted radiotherapy of prostate cancer 9PCa), Journal of Nuclear Medicine, May 2012, vol. 53, No. Suppl. 1 170.
Kothari, P., et al., 18F-labeled small molecule inhibitors of prostate specific membrane antigen (PSMA) for PET imaging of prostate cancer, Journal of Nuclear Medicine, May 2012, vol. 53, No. Suppl. 1 1721.
Clinical Trials, NCT01572701, Pilot Study of 99mTc-MIP-1404 SPECT/CT Imaging in Men With Prostate Cancer Undergoing Prostatectomy and/or Pelvic Lymph Node Dissection, posted Apr. 6, 2012. https://clinicaltrials.gov/ct2/ show/NCT01572701.
Clinical Trials, NCT01615406, A Phase 1 Pilot Study of 99mTc-MIP-1404 SPECT/CT Imaging to Histology in Men With Prostate Cancer, posted Jun. 8, 2012. https://clinicaltrials.gov/ct2/show/NCT01615406.
Clinical Trials, NCT01654874, 99mTc-MIP-1404 for Imaging Prostate Cancer: Phase I Clinical Study to Assess the Image Quality of a Simplified Kit Formulation Compared to a Multi-step Preparation of 99mTc-MIP-1404, posted Aug. 1, 2012. https://clinicaltrials.gov/ct2/show/NCT01654874.
Clinical Trials, NCT01667536, A Phase 2 Study With MIP-1404 in Men With High-Risk PC Scheduled for RP and EPLND Compared to Histopathology, posted Aug. 17, 2012. https://clinicaltrials.gov/ct2/show/NCT01667536.
Office Action for counterpart Chinese Application No. 201610184873.1, dated Jul. 24, 2018.
Shelly James, "Urea Based Rhenium Tricarbonyl Dipeptide Compounds as Potential Radiopharmaceuticals for PSMA Imaging"; Poster; INOR 258; The 229th ACS National Meeting, San Diego, CA, Mar. 13-17, 2005. http://oasys2.confex.com/acs/229nm/techprogram/P830271.HTM.
Liu M., et al., "Synthesis and Biological Evaluation of Diethylenetriamine Pentaacetic acid-Polyethylene Glycol Folate: A new Folate-Derived, 99mTc-Based Radiopharmaceutical," Bioconjugate Chem., 2005 vol. 16, p. 1126-1132.
Muller C., et al. "Synthesis and in Vitro/in Vivo Evaluation of Novel 99mTc(CO)3-Folates," Bioconjugate Chem., 2006 vol. 17, p. 797-806.
Viola-Villegas N., et al. "Targeting Gallium to Cancer Cells through the Folate Receptor," Drug Target Insights, 2008 vol. 3, p. 13-25.
Indonesian Office Action for counterpart Application No. P00202003103, dated Dec. 14, 2021.
English Translation of Notice of Reasons for Rejection for counterpart Japanese Application No. 2020-203704, dated Feb. 1, 2022.
English Translation of Second Office Action for counterpart CN Application No. 201810815832.7, dated Jan. 6, 2022.
Banerjee, S. et al., "Sequential SPECT and Optical Imaging of Experimental Models of Prostate Cancer with a Dual Modality Inhibitor of the Prostate-Specific Membrane Antigen," Angewandte Chemie International Edition, 2011, 50, 9167-9170.
Banerjee, S.R. et al. "Synthesis and Evaluation of Technetium-99m- and Rhenium-Labeled Inhibitors of the Prostate- Specific Membrane Antigen (PSMA)," J. Med. Chem. Aug. 14, 2008; 51(15): 4504-4517.
Definition of ligand, Random House Kernerman Webster's College Dictionary, downloaded on Jan. 25, 2014 from http://www.thefreedictionary.com/ligand, 1 page.
Foss, Catherine A., et al. "Radiolabeled small-molecule ligands for prostate-specific membrane antigen: in vivo imaging in experimental models of prostate cancer." Clinical cancer research 11.11 (2005): 4022-4028.
Lupold, et al., "Identification and characterization of nuclease-stabilized RNA molecules that bind human prostate cancer cells via the prostate-specific membrane antigen." Cancer Res. 2002; 62:4029-4033.
Martin, et al., Ein neuer Zugang zu 2'-0-Alkylribonucleosiden und Eigenschaften deren Oligonucleotide, Helv. Chim. Acta, 78, 486-504 (1995) and Abstract.
McNamara et al., Cell type specific delivery of siRNAs with aptamer-siRNA chimeras, Nature Biotechnology, 2006; 24:1005-1015.
Melby, et at., "Entry of Protein Toxins in Polarized Epithelial Cells," Cancer Research 53(8), pp. 1755-1760 (1993).
Olsnes, S., et al., "Immunotoxins—entry into cells and mechanisms of action," Immunology Today, 10, pp. 291-295 (1989).
Pathak et al., Enzymatic protecting group techniques in organic synthesis, Stereoselective Biocatalysis, DOI: 10.1201/9781420027242. ch26, pp. 775-797 (2000).
Roy, et al., "DUPA Conjugation of a Cytotoxic Indenoisoquinoline Topoisomerase 1 Inhibitor for Selective Prostate Cancer Cell Targeting," J. Med. Chem. 58 (2015) 3094-3103.
Truffert, et al., "Synthesis, purification and characterization of two peptide-oligonucleotide conjugates as potential artifical nucleases," DOI https://doi.org/10.1016/0040-4020(96)00018-X, Tetrahedron, 52:3005 (1996).
Zophel, K. et al., "Is 11C-choline the most appropriate tracer for KP prostate cancer?" Eur J Nucl Med Mo/ Imaging, 2004, 31, 756-759.
Substantive Examination Clear Report and Search Report received from the Malaysian Patent Office in corresponding Malaysian Application No. PI2020002949 dated Aug. 11, 2022.
Examination Report received from the United Arab Emirates Office in corresponding United Aram Emirates Application No. 390/2016 dated Oct. 18, 2022.
Office Action received from the Canadian Intellectual Property Office in related Canadian Patent Application No. 2,924,360 dated May 4, 2021.
Government of India, Indian Office Action for counterpart related Application No. 201617011691 with English-language translation, dated Nov. 9, 2021 (5 pages).
Egyptian Patent Office, "Detailed Technical Report," issued in related Egyptian Application No. 667/2016 and English-language Translation, May 19, 2022 (7 pages).
National Centre of the Intellectual Property "Sakpatenti" of Georgia, "Documentary Conclusion and Search Report," issued in related Georgian Application No. AP 2014 15719 and English-language Translation, dated May 27, 2022 (8 pages).
National Centre of the Intellectual Property "Sakpatenti" of Georgia, "Documentary Conclusion and Search Report," issued in related Georgian Application No. AP 2014 15720 and English-language Translation, dated May 27, 2022 (8 pages).
National Centre of the Intellectual Property "Sakpatenti" of Georgia, "Documentary Conclusion and Search Report," issued in related Georgian Application No. AP 2014 15377 and English-language Translation, dated Apr. 28, 2022 (8 pages).
Chinese Office Action for Application No. 201810815832.7, dated Jun. 1, 2021. (translation not available).
Translation of Japanese Notice of Reasons for Refusal for Application No. 2019-128294, dated May 25, 2021.
Qatar Examination Report for Application No. QT20160400130, dated Jun. 9, 2021.
Substantive Examination Report for Saudia Arabian Application No. SA520411464, dated Jun. 13, 2021.
Goodman, O. B., Jr., Barwe, S. P., Ritter, B., McPherson, P. S., Vasko, A. J., Keen, J. H., Nanus, D. M., Bander, N. H., and Rajasekaran, A. K. (2007) Interaction of prostate specific membrane antigen with clathrin and the adaptor protein complex-2. Int J Oncol 31, 1199-203.
Graham, K., Lesche, R., Gromov, A. V., Bohnke, N., Schafer, M., Hassfeld, J., Dinkelborg, L., and Kettschau, G. (2012) Radiofluorinated derivatives of 2-(phosphonomethyl)pentanedioic acid as inhibitors of prostate specific membrane antigen (PSMA) for the imaging of prostate cancer. J Med Chem 55, 9510-20.
Grant, C. L., Caromile, L. A., Ho, V., Durrani, K., Rahman, M. M., Claffey, K. P., Fong, G. H., and Shapiro, L. H. (2012) Prostate

(56) References Cited

OTHER PUBLICATIONS specific membrane antigen (PSMA) regulates angiogenesis independently of VEGF during ocular neovascularization. PLoS One 7, e41285.
Gregor, P. D., Wolchok, J. D., Turaga, V., Latouche, J. B., Sadelain, M., Bacich, D., Heston, W. D., Houghton, A. N., and Scher, H. I. (2005) Induction of autoantibodies to syngeneic prostate-specific membrane antigen by xenogeneic vaccination. Int J Cancer 116, 415-21.
Haberkom, U., Mier, W., Dimitrakopoulou-Strauss, A., Eder, M., Kopka, K., and Altmann, A. (2014) Mechanistic and high-throughput approaches for the design of molecular imaging probes and targeted therapeutics. Clinical and Translational Imaging 2, 33-41.
Haffner, M. C., Kronberger, I. E., Ross, J. S., Sheehan, C. E., Zitt, M., Muhlmann, G., Ofner, D., Zelger, B., Ensinger, C., Yang, X. J., Geley, S., Margreiter, R., and Bander, N. H. (2009) Prostate-specific membrane antigen expression in the neovasculature of gastric and colorectal cancers. Hum Pathol 40, 1754-61.
Hain, S. F., and Maisey, M. N. (2003) Positron emission tomography for urological tumours. BJU Int 92, 159-64.
Hara, T. (2002) 11C-choline and 2-deoxy-2-[18F]fluoro-D-glucose in tumor imaging with positron emission tomography. Mol Imaging Biol 4, 267-73.
Hara, T., Kosaka, N., and Kishi, H. (1998) PET imaging of prostate cancer using carbon-11-choline. J Nucl Med 39, 990-5.
Hara, T., Kosaka, N., and Kishi, H. (2002) Development of (18)F-fluoroethylcholine for cancer imaging with PET: synthesis, biochemistry, and prostate cancer imaging. J Nucl Med 43, 187-99.
Harada, N., Kimura, H., Ono, M., and Saji, H. (2013) Preparation of asymmetric urea derivatives that target prostate-specific membrane antigen for SPECT imaging. J Med Chem 56, 7890-901.
Heidenreich, A. (2012) [Immunotherapy for metastatic prostate cancer: do we really need this?]. Der Urologe. Ausg. A 51, 32-8.
Henry, M. D., Wen, S., Silva, M. D., Chandra, S., Milton, M., and Worland, P. J. (2004) A prostate-specific membrane antigen-targeted monoclonal antibody-chemotherapeutic conjugate designed for the treatment of prostate cancer. Cancer Res 64, 7995-8001.
Hillier, S. M., Kern, A. M., Maresca, K. P., Marquis, J. C., Eckelman, W. C., Joyal, J. L., and Babich, J. W. (2011) 123I-MIP-1072, a small-molecule inhibitor of prostate-specific membrane antigen, is effective at monitoring tumor response to taxane therapy. J Nucl Med 52, 1087-93.
Hillier, S. M., Maresca, K. P., Femia, F. J., Marquis, J. C., Foss, C. A., Nguyen, N., Zimmerman, C. N., Barrett, J. A., Eckelman, W. C., Pomper, M. G., Joyal, J. L., and Babich, J. W. (2009) Preclinical evaluation of novel glutamate-urea-lysine analogues that target prostate-specific membrane antigen as molecular imaging pharmaceuticals for prostate cancer. Cancer Res 69, 6932-40.
Hillier, S. M., Maresca, K. P., Lu, G., Merkin, R. D., Marquis, J. C., Zimmerman, C. N., Eckelman, W. C., Joyal, J. L., and Babich, J. W. (2013) 99mTc-labeled small-molecule inhibitors of prostate-specific membrane antigen for molecular Imaging of prostate cancer. J Nucl Med 54, 1369-76.
Hlouchova, K., Barinka, C., Klusak, V., Sacha, P., Mlcochova, P., Majer, P., Rulisek, L., and Konvalinka, J. (2007) Biochemical characterization of human glutamate carboxypeptidase III. Journal of neurochemistry 101, 682-96.
Hlouchova, K., Barinka, C., Konvalinka, J., and Lubkowski, J. (2009) Structural insight into the evolutionary and pharmacologic homology of glutamate carboxypeptidases II and III. Febs J 276, 4448-62.
Hlouchova, K., Navratil, V., Tykvart, J., Sacha, P., and Konvalinka, J. (2012). GCPII variants, paralogs and orthologs. Curr Med Chem 19, 1316-22.
Ho, C. L., Liu, I. H., Wu, Y. H., Chen, L. C., Chen, C. L., Lee, W. C., Chuang, C. H., Lee, T. W., Lin, W. J., Shen, L. H., and Chang, C. H. (2011) Molecular imaging, pharmacokinetics, and dosimetry of In-AMBA in human prostate tumor- bearing mice. J Biomed Biotechnol 2011, 101497.
Holland, J. P., Divilov, V., Bander, N. H., Smith-Jones, P. M., Larson, S. M., and Lewis, J. S. (2010) 89Zr—DFO-J591 for immunoPET of prostate-specific membrane antigen expression in vivo. J Nucl Med 51, 1293-300.
Hong, H., Zhang, Y., Sun, J., and Cai, W. (2010) Positron emission tomography imaging of prostate cancer. Amino Acids 39, 11-27.
Hospers, G. A., Helmond, F. A., de Vries, E. G., Dierckx, R. A., and de Vries, E. F. (2008) PET imaging of steroid receptor expression in breast and prostate cancer. Curr Pharm Des 14, 3020-32.
Huang, B., Otis, J., Joice, M., Kotlyar, A., and Thomas, T. P. (2014) PSMA-Targeted Stably Linked "Dendrimer-Glutamate Urea-Methotrexate" as a Prostate Cancer Therapeutic. Biomacromolecules 15, 915-23.
Huang, S. S., Wang, X., Zhang, Y., Doke, A., DiFilippo, F. P., and Heston, W. D. (2014) Improving the biodistribution of PSMA-targeting tracers with a highly negatively charged linker. Prostate 74, 702-13.
Kozikowski, A. P., Zhang, J., Nan, F., Petukhov, P. A., Grajkowska, E., Wroblewski, J. T., Yamamoto, T., Bzdega, T., Wroblewska, B., and Neale, J. H. (2004) Synthesis of urea-based inhibitors as active site probes of glutamate carboxypeptidase II: efficacy as analgesic agents. J Med Chem 47, 1729-38.
Humblet, V., Lapidus, R., Williams, L. R., Tsukamoto, T., Rojas, C., Majer, P., Hin, B., Ohnishi, S., De Grand, A. M., Zaheer, A., Renze, J. T., Nakayama, A., Slusher, B. S., and Frangioni, J. V. (2005) High-affinity near-infrared fluorescent small-molecule contrast agents for in vivo imaging of prostate-specific membrane antigen. Mol Imaging 4, 448-62.
Humblet, V., Misra, P., Bhushan, K. R., Nasr, K., Ko, Y. S., Tsukamoto, T., Pannier, N., Frangioni, J. V., and Maison, W. (2009) Multivalent scaffolds for affinity maturation of small molecule cell surface binders and their application to prostate tumor targeting. J Med Chem 52, 544-50.
Husarik, D. B., Miralbell, R., Dubs, M., John, H., Giger, O. T., Gelet, A., Cservenyak, T., and Hany, T. F. (2008) Evaluation of [(18)F]-choline PET/CT for staging and restaging of prostate cancer. Eur J Nucl Med Mol Imaging 35, 253-63.
Hwang, D. R., Lang, L. X., Mathias, C. J., Kadmon, D., and Welch, M. J. (1989) N-3-[18F]fluoropropylputrescine as potential PET imaging agent for prostate and prostate derived tumors. J Nucl Med 30, 1205-10.
Hwang, D. R., Mathias, C. J., Welch, M. J., McGuire, A. H., and Kadmon, D. (1990) Imaging prostate derived tumors with PET and N-(3-[18F]fluoropropyl)putrescine. Int J Rad Appl Instrum B 17, 525-32.
Igerc, I., Kohlfurst, S., Gallowitsch, H. J., Matschnig, S., Kresnik, E., Gomez-Segovia, I., and Lind, P. (2008) The value of 18F-choline PET/CT in patients with elevated PSA-level and negative prostate needle biopsy for localisation of prostate cancer. Eur J Nucl Med Mol Imaging 35, 976-83.
Jackson P.F., Cole D.C., Slusher B.S., Stetz S.L., Ross L.E., Donzanti B.A., and D.A., T. (1996) Design, synthesis, and biological activity of a potent inhibitor of the neuropeptidase N-acetylated alpha-linked acidic dipeptidase. J Med Chem. Jan. 19, 1996;39(2):619-22. doi: 10.1021/jm950801q.
Jadvar, H. (2009) Molecular imaging of prostate cancer with 18F-fluorodeoxyglucose PET. Nat Rev Urol 6, 317-23.
Jadvar, H. (2012) Molecular imaging of prostate cancer: PET radiotracers. AJR Am J Roentgenol 199, 278-91.
Jadvar, H. (2013) Imaging evaluation of prostate cancer with (18)F-fluorodeoxyglucose PET/CT: utility and limitations. Eur J Nucl Med Mol Imaging 40 (Suppl 1), S5-S10.
Jadvar, H., Xiankui, L., Shahinian, A., Park, R., Tohme, M., Pinski, J., and Conti, P. S. (2005) Glucose metabolism of human prostate cancer mouse xenografts. Mol Imaging 4, 91-7.
Jambor, I., Borra, R., Kemppainen, J., Lepomaki, V., Parkkola, R., Dean, K., Alanen, K., Arponen, E., Nurmi, M., Aronen, H. J., and Minn, H. (2010) Functional imaging of localized prostate cancer aggressiveness using 11C-acetate PET/CT and 1H-MR spectroscopy. J Nucl Med 51, 1676-83.
Jemaa, A. B., Bouraoui, Y., Sallami, S., Banasr, A., Nouira, Y., Horchani, A., and Oueslati, R. (2013) Cellular distribution and

(56) References Cited

OTHER PUBLICATIONS heterogeneity of Psa and Psma expression in normal, hyperplasia and human prostate cancer. La tunisie Medicale 91, 458-463.

Kahn, D., Williams, R. D., Manyak, M. J., Haseman, M. K., Seldin, D. W., Libertino, J. A., and Maguire, R. T. (1998) 111Indium-capromab pendetide in the evaluation of patients with residual or recurrent prostate cancer after radical prostatectomy. The ProstaScint Study Group. J Urol 159, 2041-6; discussion 2046-7.

Kasperzyk, J. L., Finn, S. P., Flavin, R., Fiorentino, M., Lis, R., Hendrickson, W. K., Clinton, S. K., Sesso, H. D., Giovannucci, E. L., Stampfer, M. J., Loda, M., and Mucci, L. A. (2013) Prostate-specific membrane antigen protein expression in tumor tissue and risk of lethal prostate cancer. Cancer Epidemiol Biomarkers Prev 22, 2354-63.

Kasten, B. B., Liu, T., Nedrow-Byers, J. R., Benny, P. D., and Berkman, C. E. (2013) Targeting prostate cancer cells with PSMA inhibitor-guided gold nanoparticles. Bioorg Med Chem Lett 23, 565-8.

Kim, D., Kim, S. K., Valencia, C. A., and Liu, R. (2013) Tribody: robust self-assembled trimeric targeting ligands with high stability and significantly improved target-binding strength. Biochemistry 52, 7283-94.

Kinoshita, Y., Kuratsukuri, K., Landas, S., Imaida, K., Rovito, P. M., Jr., Wang, C. Y., and Haas, G. P. (2006) Expression of prostate-specific membrane antigen in normal and malignant human tissues. World J Surg 30, 628-36.

Klotz, L. (2012) Cancer overdiagnosis and overtreatment. Curr Opin Urol 22, 203-9.

Klusak, V., Barinka, C., Plechanovova, A., Micochova, P., Konvalinka, J., Rulisek, L., and Lubkowski, J. (2009) Reaction mechanism of glutamate carboxypeptidase II revealed by mutagenesis, X-ray crystallography, and computational methods. Biochemistry 48, 4126-38.

Kosuri, S., Akhtar, N. H., Smith, M., Osborne, J. R., and Tagawa, S. T. (2012) Review of salvage therapy for biochemically recurrent prostate cancer: the role of imaging and rationale for systemic salvage targeted anti-prostate-specific membrane antigen radioimmunotherapy. Advances in Urology 2012, 921674.

Kotzerke, J., Gschwend, J. E., and Neumaier, B. (2002) PET for prostate cancer imaging: still a quandary or the ultimate solution? J Nucl Med 43, 200-2.

Kovar, J. L., Cheung, L. L., Simpson, M. A., and Olive, D. M. (2014) Pharmacokinetic and Biodistribution Assessment of a Near Infrared-Labeled PSMA-Specific Small Molecule in Tumor-Bearing Mice. Prostate Cancer 2014, 104248.

Krohn, T., Verburg, F. A., Pufe, T., Neuhuber, W., Vogg, A., Heinzel, A., Mottaghy, F. M., and Behrendt, F. F. (2014) [Ga]PSMA-HBED uptake mimicking lymph node metastasis in coeliac ganglia: an important pitfall in clinical practice. Eur J Nucl Med Mol Imaging 42, 210-14.

Kularatne, S. A., Venkatesh, C., Santhapuram, H. K., Wang, K., Vaitilingam, B., Henne, W. A., and Low, P. S. (2010) Synthesis and biological analysis of prostate-specific membrane antigen-targeted anticancer prodrugs. J Med Chem 53, 7767-77.

Kularatne, S. A., Wang, K., Santhapuram, H. K., and Low, P. S. (2009) Prostate-specific membrane antigen targeted imaging and therapy of prostate cancer using a PSMA inhibitor as a homing ligand. Mol Pharm 6, 780-9.

Osborne, J. R., Akhtar, N. H., Vallabhajosula, S., Anand, A., Deh, K., and Tagawa, S. T. (2013) Prostate-specific membrane antigen-based imaging. Urol Oncol 31, 144-54.

Osborne, J. R., Green, D. A., Spratt, D. E., Lyashchenko, S., Fareedy, S. B., Robinson, B. D., Beattie, B. J., Jain, M., Lewis, J. S., Christos, P., Larson, S. M., Bander, N. H., and Scherr, D. S. (2013) A Prospective Pilot Study of Zr-J591/ Prostate Specific Membrane Antigen Positron Emission Tomography in Men with Localized Prostate Cancer Undergoing Radical Prostatectomy. J Urol 191, 1439-46.

Kularatne, S. A., Zhou, Z., Yang, J., Post, C. B., and Low, P. S. (2009) Design, synthesis, and preclinical evaluation of prostate-specific membrane antigen targeted (99m)Tc-radioimaging agents. Mol Pharm 6, 790-800.

Kuru, T. H., Tulea, C., Simpfendorfer, T., Popeneciu, V., Roethke, M., Hadaschik, B. A., and Hohenfellner, M. (2012) [MRI navigated stereotactic prostate biopsy: fusion of MRI and real-time transrectal ultrasound images for perineal prostate biopsies]. Der Urologe. Ausg. A 51, 50-6.

Kwee, S. A., Coel, M. N., Ly, B. H., and Lim, J. (2009) (18)F-Choline PET/CT imaging of RECIST measurable lesions In hormone refractory prostate cancer. Ann Nucl Med 23, 541-8.

Lambert, L. A., and Mitchell, S. L. (2007) Molecular evolution of the transferrin receptor/glutamate carboxypeptidase II family. Journal of Molecular Evolution 64, 113-28.

Lapi, S. E., Wahnishe, H., Pham, D., Wu, L. Y., Nedrow-Byers, J. R., Liu, T., Vejdani, K., VanBrocklin, H. F., Berkman, C. E., and Jones, E. F. (2009) Assessment of an 18F-labeled phosphoramidate peptidomimetic as a new prostate-specific membrane antigen-targeted imaging agent for prostate cancer. J Nucl Med 50, 2042-8.

Leek, J., Lench, N., Maraj, B., Bailey, A., Carr, I. M., Andersen, S., Cross, J., Whelan, P., MacLennan, K. A., Meredith, D. M., and et al. (1995) Prostate-specific membrane antigen: evidence for the existence of a second related human gene. Br J Cancer 72, 583-8.

Lees, K., Durve, M., and Parker, C. (2012) Active surveillance in prostate cancer: patient selection and triggers for Intervention. Curr Opin Urol 22, 210-5.

Lesche, R., Kettschau, G., Gromov, A. V., Bohnke, N., Borkowski, S., Monning, U., Hegele-Hartung, C., Dohr, O., Dinkelborg, L. M., and Graham, K. (2013) Preclinical evaluation of BAY 1075553, a novel F-labelled inhibitor of prostate-specific membrane antigen for PET imaging of prostate cancer. Eur J Nucl Med Mol Imaging 41, 89-101.

I, X., Liu, Q., Wang, M., Jin, X., Yao, S., Liu, S., and Li, J. (2008) C-11 choline PET/CT imaging for differentiating malignant from benign prostate lesions. Clin Nucl Med 33, 671-6.

Liu, H., Rajasekaran, A. K., Moy, P., Xia, Y., Kim, S., Navarro, V., Rahmati, R., and Bander, N. H. (1998) Constitutive and antibody-induced internalization of prostate-specific membrane antigen. Cancer Res 58, 4055-60.

Iu, T., Mendes, D. E., and Berkman, C. E. (2014) Functional prostate-specific membrane antigen is enriched in exosomes from prostate cancer cells. Int J Oncol 44, 918-22.

Liu, T., Nedrow-Byers, J. R., Hopkins, M. R., Wu, L. Y., Lee, J., Reilly, P. T., and Berkman, C. E. (2012) Targeting prostate cancer cells with a multivalent PSMA inhibitor-guided streptavidin conjugate. Bioorg Med Chem Lett 22, 3931-4.

Liu, T., Toriyabe, Y., Kazak, M., and Berkman, C. E. (2008) Pseudoirreversible inhibition of prostate-specific membrane antigen by phosphoramidate peptidomimetics. Biochemistry 47, 12658-60.

Liu, T., Wu, L. Y., Fulton, M. D., Johnson, J. M., and Berkman, C. E. (2012) Prolonged androgen deprivation leads to downregulation of androgen receptor and prostate-specific membrane antigen in prostate cancer cells. Int J Oncol 41, 2087-92.

Liu, T., Wu, L. Y., Hopkins, M. R., Choi, J. K., and Berkman, C. E. (2010) A targeted low molecular weight near-Infrared fluorescent probe for prostate cancer. Bioorg Med Chem Lett 20, 7124-6.

Lord, M., Ratib, O., and Vallee, J. P. (2011) (1)(8)F-Fluorocholine integrated PET/MRI for the initial staging of prostate cancer. Eur J Nucl Med Mol Imaging 38, 2288.

Lu, G., Maresca, K. P., Hillier, S. M., Zimmerman, C. N., Eckelman, W. C., Joyal, J. L., and Babich, J. W. (2013) Synthesis and SAR of (9)(9)mTc/Re-labeled small molecule prostate specific membrane antigen inhibitors with novel polar chelates. Bioorg Med Chem Lett 23, 1557-63.

Luboldt, W., Kufer, R., Blumstein, N., Toussaint, T. L., Kluge, A., Seemann, M. D., and Luboldt, H. J. (2008) Prostate carcinoma: diffusion-weighted imaging as potential alternative to conventional MR and 11C-choline PET/CT for detection of bone metastases. Radiology 249, 1017-25.

Lutje, S., Boerman, O. C., van Rij, C. M., Sedelaar, M., Helfrich, W., Oyen, W. J., and Mulders, P. F. (2012) Prospects in radionuclide imaging of prostate cancer. Prostate 72, 1262-72.

(56) References Cited

OTHER PUBLICATIONS

Lutje, S., Rijpkema, M., Franssen, G. M., Fracasso, G., Helfrich, W., Eek, A., Oyen, W. J., Colombatti, M., and Boerman, O. C. (2014) Dual-Modality Image-Guided Surgery of Prostate Cancer with a Radiolabeled Fluorescent Anti-PSMA Monoclonal Antibody. J Nucl Med 55, 995-1001.

Malik, N., Machulla, H. J., Solbach, C., Winter, G., Reske, S. N., and Zlatopolskiy, B. (2011) Radiosynthesis of a new PSMA targeting ligand ([18F]FPy-DUPA-Pep). Appl Radiat Isot 69, 1014-8.

Malik, N., Zlatopolskiy, B., Machulla, H.-J., Reske, S. N., and Solbach, C. (2012) One pot radiofluorination of a new potential PSMA ligand [Al18F]NOTA-DUPA-Pep. Journal of Labelled Compounds and Radiopharmaceuticals 55, 320-325.

Mannweiler, S., Amersdorfer, P., Trajanoski, S., Terrett, J. A., King, D., and Mehes, G. (2009) Heterogeneity of prostate-specific membrane antigen (PSMA) expression in prostate carcinoma with distant metastasis. Pathology oncology research : POR 15, 167-72.

Maresca, K. P., Hillier, S. M., Femia, F. J., Keith, D., Barone, C., Joyal, J. L., Zimmerman, C. N., Kozikowski, A. P., Barrett, J. A., Eckelman, W. C., and Babich, J. W. (2009) A series of halogenated heterodimeric inhibitors of prostate specific membrane antigen (PSMA) as radiolabeled probes for targeting prostate cancer. J Med Chem 52, 347-57.

Matthies, A., Ezziddin, S., Ulrich, E. M., Palmedo, H., Biersack, H. J., Bender, H., and Guhlke, S. (2004) Imaging of prostate cancer metastases with 18F-fluoroacetate using PET/CT. Eur J Nucl Med Mol Imaging 31, 797.

Mease RC, Foss CA, and MG, P. (2013) PET imaging in prostate cancer: focus on prostate-specific membrane antigen. Curr Top Med Chem 13, 951-962.

Mease, R. C., Dusich, C. L., Foss, C. A., Ravert, H. T., Dannals, R. F., Seidel, J., Prideaux, A., Fox, J. J., Sgouros, G., Kozikowski, A. P., and Pomper, M. G. (2008) N-[N-[(S)-1,3-Dicarboxypropyl]carbamoyl]-4-[18F]fluorobenzyl-L-cysteine, [18F]DCFBC: a new imaging probe for prostate cancer. Clin Cancer Res 14, 3036-43.

Meighan, M. A., Dickerson, M. T., Glinskii, O., Glinsky, V. V., Wright, G. L., Jr., and Deutscher, S. L. (2003) Recombinant glutamate carboxypeptidase II (prostate specific membrane antigen-PSMA)—cellular localization and bioactivity analyses. J Protein Chem 22, 317-26.

Meinhardt, W., van der Poel, H. G., Valdes Olmos, R. A., Bex, A., Brouwer, O. R., and Horenblas, S. (2012) Laparoscopic sentinel lymph node biopsy for prostate cancer: the relevance of locations outside the extended dissection area. Prostate Cancer 2012, 751753.

Mertens, K., Slaets, D., Lambert, B., Acou, M., De Vos, F., and Goethals, I. (2010) PET with (18)F-labelled choline-based tracers for tumour imaging: a review of the literature. Eur J Nucl Med Mol Imaging 37, 2188-93.

Mesters, J. R., Barinka, C., Li, W., Tsukamoto, T., Majer, P., Slusher, B. S., Konvalinka, J., and Hilgenfeld, R. (2006) Structure of glutamate carboxypeptidase II, a drug target in neuronal damage and prostate cancer. EMBO J 25, 1375-84.

Mhawech-Fauceglia, P., Zhang, S., Terracciano, L., Sauter, G., Chadhuri, A., Herrmann, F. R., and Penetrante, R. (2007) Prostate-specific membrane antigen (PSMA) protein expression in normal and neoplastic tissues and its sensitivity and specificity in prostate adenocarcinoma: an immunohistochemical study using mutiple tumour tissue microarray technique. Histopathology 50, 472-83.

Milowsky, M. I., Nanus, D. M., Kostakoglu, L., Vallabhajosula, S., Goldsmith, S. J., and Bander, N. H. (2004) Phase I trial of yttrium-90-labeled anti-prostate-specific membrane antigen monoclonal antibody J591 for androgen-independent prostate cancer. J Clin Oncol 22, 2522-31.

Minner, S., Wittmer, C., Graefen, M., Salomon, G., Steuber, T., Haese, A., Huland, H., Bokemeyer, C., Yekebas, E., Dierlamm, J., Balabanov, S., Kilic, E., Wilczak, W., Simon, R., Sauter, G., and Schlomm, T. (2011) High level PSMA expression is associated with early PSA recurrence in surgically treated prostate cancer. Prostate 71, 281-8.

Micochova, P., Plechanovova, A., Barinka, C., Mahadevan, D., Saldanha, J. W., Rulisek, L., and Konvalinka, J. (2007) Mapping of the active site of glutamate carboxypeptidase II by site-directed mutagenesis. FEBS J 274, 4731-41.

Moltzahn, F., and Thalmann, G. N. (2012) [Bone metastasis in prostate cancer]. Der Urologe. Ausg. A 51, 20-6.

Morris, M. J., and Scher, H. I. (2007) (11)C-acetate PET imaging in prostate cancer. Eur J Nucl Med Mol Imaging 34, 181-4.

Murphy, G. P., Elgamal, A. A., Su, S. L., Bostwick, D. G., and Holmes, E. H. (1998) Current evaluation of the tissue localization and diagnostic utility of prostate specific membrane antigen. Cancer 83, 2259-69.

Nedrow-Byers, J. R., Jabbes, M., Jewett, C., Ganguly, T., He, H., Liu, T., Benny, P., Bryan, J. N., and Berkman, C. E. (2012) A phosphoramidate-based prostate-specific membrane antigen-targeted SPECT agent. Prostate 72, 904-12.

Nedrow-Byers, J. R., Moore, A. L., Ganguly, T., Hopkins, M. R., Fulton, M. D., Benny, P. D., and Berkman, C. E. (2013) PSMA-targeted SPECT agents: mode of binding effect on in vitro performance. Prostate 73, 355-62.

Oehr, P., and Bouchelouche, K. (2007) Imaging of prostate cancer. Curr Opin Oncol 19, 259-64.

O'Keefe, D. S., Bacich, D. J., and Heston, W. D. (2004) Comparative analysis of prostate-specific membrane antigen (PSMA) versus a prostate-specific membrane antigen-like gene. Prostate 58, 200-10.

Omlin, A., and Gillessen, S. (2012) [Inhibitors of androgen and estrogen biosynthesis in castration-resistant prostate cancer]. Der Urologe. Ausg. A 51, 8-14.

Bostwick, D. G., Pacelli, A., Blute, M., Roche, P., and Murphy, G. P. (1998) Prostate specific membrane antigen expression in prostatic intraepithelial neoplasia and adenocarcinoma: a study of 184 cases. Cancer 82, 2256-61.

Bouchelouche, K., and Capala, J. (2010) 'Image and treat': an individualized approach to urological tumors. Curr Opin Oncol 22, 274-80.

Bouchelouche, K., Capala, J., and Oehr, P. (2009) Positron emission tomography/computed tomography and radioimmunotherapy of prostate cancer. Curr Opin Oncol 21, 469-74.

Bouchelouche, K., Choyke, P. L., and Capala, J. (2010) Prostate specific membrane antigen—a target for imaging and therapy with radionuclides. Discov Med 9, 55-61.

Bouchelouche, K., Tagawa, S. T., Goldsmith, S. J., Turkbey, B., Capala, J., and Choyke, P. (2011) PET/CT Imaging and Radioimmunotherapy of Prostate Cancer. Semin Nucl Med 41, 29-44.

Bzdega, T., Crowe, S. L., Ramadan, E. R., Sciarretta, K. H., Olszewski, R. T., Ojeifo, O. A., Rafalski, V. A., Wroblewska, B., and Neale, J. H. (2004) The cloning and characterization of a second brain enzyme with NAAG peptidase activity. Journal of neurochemistry 89, 627-35.

Ceci, F., Castellucci, P., Mamede, M., Schiavina, R., Rubello, D., Fuccio, C., Ambrosini, V., Boschi, S., Martorana, G., and Fanti, S. (2013) (11)C-Choline PET/CT in patients with hormone-resistant prostate cancer showing biochemical relapse after radical prostatectomy. Eur J Nucl Med Mol Imaging 40, 149-55.

Chandran, S. S., Banerjee, S. R., Mease, R. C., Pomper, M. G., and Denmeade, S. R. (2008) Characterization of a targeted nanoparticle functionalized with a urea-based inhibitor of prostate-specific membrane antigen (PSMA). Cancer Biol Ther 7, 974-82.

Chang, S. S., and Heston, W. D. (2002) The clinical role of prostate-specific membrane antigen (PSMA). Urol Oncol 7, 7-12.

Chang, S. S., Reuter, V. E., Heston, W. D., Bander, N. H., Grauer, L. S., and Gaudin, P. B. (1999) Five different anti-prostate-specific membrane antigen (PSMA) antibodies confirm PSMA expression in tumor-associated neovasculature. Cancer Res 59, 3192-8.

Chen, J., Zhao, Y., Li, X., Sun, P., Wang, M., Wang, R., and Jin, X. (2012) Imaging primary prostate cancer with 11C-Choline PET/CT: relation to tumour stage, Gleason score and biomarkers of biologic aggressiveness. Radiology and oncology 46, 179-88.

Chen, Y., Dhara, S., Banerjee, S. R., Byun, Y., Pullambhatla, M., Mease, R. C., and Pomper, M. G. (2009) A low molecular weight PSMA-based fluorescent imaging agent for cancer. Biochem Biophys Res Commun 390, 624-9.

(56) References Cited

OTHER PUBLICATIONS

Chen, Y., Foss, C. A., Byun, Y., Nimmagadda, S., Pullambhatla, M., Fox, J. J., Castanares, M., Lupold, S. E., Babich, J. W., Mease, R. C., and Pomper, M. G. (2008) Radiohalogenated prostate-specific membrane antigen (PSMA)-based ureas as imaging agents for prostate cancer. J Med Chem 51, 7933-43.

Chen, Y., Pullambhatla, M., Banerjee, S. R., Byun, Y., Stathis, M., Rojas, C., Slusher, B. S., Mease, R. C., and Pomper, M. G. (2012) Synthesis and biological evaluation of low molecular weight fluorescent imaging agents for the prostate-specific membrane antigen. Bioconjug Chem 23, 2377-85.

Chen, Y., Pullambhatla, M., Byun, Y., Foss, C. A., Nimmagadda, S., Senthamizhchelvan, S., Sgouros, G., Mease, R. C., and Pomper, M. G. (2011) 2-(3-{1-Carboxy-5-[(6-[18F]fluoro-pyridine-3-carbonyl)-amino]-pentyl}-ureido)-pentanedioic acid, [18F]DCFPyL, a PSMA-based PET Imaging Agent for Prostate Cancer. Clin Cancer Res 17, 7645-53.

Chen, Z., Penet, M. F., Nimmagadda, S., Li, C., Banerjee, S. R., Winnard, P. T., Jr., Artemov, D., Glunde, K., Pomper, M. G., and Bhujwalla, Z. M. (2012) PSMA-targeted theranostic nanoplex for prostate cancer therapy. ACS Nano 6, 7752-62.

Chopra, A. (2004) 68Ga-Labeled 2-[3-(1-carboxy-5-{7-[5-carboxy-5-(3-phenyl-2-{3-phenyl-2-[2-(4,7, 10-tris-carboxymethyl-1,4,7, 10-tetraazacyclododec-1-l)acetylamino]propionylamino}propionylamino )pentylcarbamoyl] heptanoylamino}pentyl)ureido]pentanedioic acid. Molecular Imaging and Contrast Agent Database (MICAD) [database online]. Bethesda (MD): National Center for Biotechnology Information (US); 2004-2013.

Chopra, A. (2004) 68Ga-Labeled 2-{3-[5-(7-{1-benzyloxycarbonyl-5-[2-(4,7, 10-tris-carboxymethyl-1,4,7, 10-tetraazacyclododec-1-ll)acetylamino]pentylcarbamoyl}-heptanoylamino)-1-carboxypentyl]ureido}pentanedioic acid. Molecular Imaging and Contrast Agent Database (MICAD) [database online]. Bethesda (MD): National Center for Biotechnology Information (US); 2004-2013.

Chuu, C. P., Kokontis, J. M., Hiipakka, R. A., Fukuchi, J., Lin, H. P., Lin, C. Y., Huo, C., Su, L. C., and Liao, S. (2011) Androgen suppresses proliferation of castration-resistant LNCaP 104-R2 prostate cancer cells through androgen receptor, Skp2, and c-Myc. Cancer Science 102, 2022-8.

Cimitan, M., Bortolus, R., Morassut, S., Canzonieri, V., Garbeglio, A., Baresic, T., Borsatti, E., Drigo, A., and Trovo, M. G. (2006) [18F]fluorocholine PET/CT imaging for the detection of recurrent prostate cancer at PSA relapse: experience In 100 consecutive patients. Eur J Nucl Med Mol Imaging 33, 1387-98.

Colabufo, N. A., Abate, C., Contino, M., Inglese, C., Niso, M., Berardi, F., and Perrone, R. (2008) PB183, a sigma receptor ligand, as a potential PET probe for the imaging of prostate adenocarcinoma. Bioorg Med Chem Lett 18, 1990-3.

Cunha, A. C., Weigle, B., Kiessling, A., Bachmann, M., and Rieber, E. P. (2006) Tissue-specificity of prostate specific antigens: comparative analysis of transcript levels in prostate and non-prostatic tissues. Cancer Lett 236, 229-38.

Dahl, M., Bouchelouche, P., Kramer-Marek, G., Capala, J., Nordling, J., and Bouchelouche, K. (2011) Sarcosine induces increase in HER2/neu expression in androgen-dependent prostate cancer cells. Molecular biology reports 38, 4237-43.

De Santis, M., and Bachner, M. (2012) [Role of chemotherapy in castration-resistant prostate cancer: are there new approaches?]. Der Urologe. Ausg. A 51, 39-43.

DeGrado, T. R., Baldwin, S. W., Wang, S., Orr, M. D., Liao, R. P., Friedman, H. S., Reiman, R., Price, D. T., and Coleman, R. E. (2001) Synthesis and evaluation of (18)F-labeled choline analogs as oncologic PET tracers. J Nucl Med 42, 1805-14.

DeGrado, T. R., Coleman, R. E., Wang, S., Baldwin, S. W., Orr, M. D., Robertson, C. N., Polascik, T. J., and Price, D. T. (2001) Synthesis and evaluation of 18F-labeled choline as an oncologic tracer for positron emission tomography: initial findings in prostate cancer. Cancer Res 61, 110-7.

Dimitrakopoulou-Strauss, A., and Strauss, L. G. (2003) PET imaging of prostate cancer with 11C-acetate. J Nucl Med 44, 556-8.

Divyya, S., Naushad, S. M., Murthy, P. V., Reddy Ch, R., and Kutala, V. K. (2013) GCPII modulates oxidative stress and prostate cancer susceptibility through changes in methylation of RASSF1, BNIP3, GSTP1 and Ec-SOD. Molecular Biology Reports 40, 5541-50.

Dumas, F., Gala, J. L., Berteau, P., Brasseur, F., Eschwege, P., Paradis, V., Lacour, B., Philippe, M., and Loric, S. (1999) Molecular expression of PSMA mRNA and protein in primary renal tumors. Int J Cancer 80, 799-803.

Eder, M., Eisenhut, M., Babich, J., and Haberkorn, U. (2013) PSMA as a target for radiolabelled small molecules. Eur J Nucl Med Mol Imaging 40, 819-23.

Eder, M., Neels, O., Muller, M., Bauder-Wust, U., Remde, Y., Schafer, M., Hennrich, U., Eisenhut, M., Afshar-Oromieh, A., Haberkorn, U., and Kopka, K. (2014) Novel Preclinical and Radiopharmaceutical Aspects of [68Ga]Ga-PSMA-Hbed-Cc: A New PET Tracer for Imaging of Prostate Cancer. Pharmaceuticals 7, 779-96.

Eder, M., Schafer, M., Bauder-Wust, U., Haberkorn, U., Eisenhut, M., and Kopka, K. (2014) Preclinical evaluation of a bispecific low-molecular heterodimer targeting both PSMA and GRPR for improved PET imaging and therapy of prostate cancer. Prostate 74(6):659-68. doi: 10.1002/pros.22784.

Eder, M., Schafer, M., Bauder-Wust, U., Hull, W. E., Wangler, C., Mier, W., Haberkorn, U., and Eisenhut, M. (2012) (68)Ga-Complex Lipophilicity and the Targeting Property of a Urea-Based PSMA Inhibitor for PET Imaging. Bioconjug Chem 23, 688-97.

Eiber, M., Nekolla, S. G., Maurer, T., Weirich, G., Wester, H. J., and Schwaiger, M. (2014) Ga-PSMA PET/MR with multimodality image analysis for primary prostate cancer. Abdom Imaging 40, 1769-71.

Elsasser-Beile, U., Buhler, P., and Wolf, P. (2009) Targeted therapies for prostate cancer against the prostate specific membrane antigen. Curr Drug Targets 10, 118-25.

Elsasser-Beile, U., Reischl, G., Wiehr, S., Buhler, P., Wolf, P., Alt, K., Shively, J., Judenhofer, M. S., Machulla, H. J., and Pichler, B. J. (2009) PET imaging of prostate cancer xenografts with a highly specific antibody against the prostate-specific membrane antigen. J Nucl Med 50, 606-11.

Elsasser-Beile, U., Wolf, P., Gierschner, D., Buhler, P., Schultze-Seemann, W., and Wetterauer, U. (2006) A new generation of monoclonal and recombinant antibodies against cell-adherent prostate specific membrane antigen for diagnostic and therapeutic targeting of prostate cancer. Prostate 66, 1359-70.

El-Zaria, M. E., Genady, A. R., Janzen, N., Petlura, C. I., Beckford Vera, D. R., and Valliant, J. F. (2014) Preparation and evaluation of carborane-derived inhibitors of prostate specific membrane antigen (PSMA). Dalton Trans 43, 4950-61.

Emonds, K. M., Swinnen, J. V., van Weerden, W. M., Vanderhoydonc, F., Nuyts, J., Mortelmans, L., and Mottaghy, F. M. (2011) Do androgens control the uptake of 18F-FDG, 11C-choline and 11C-acetate in human prostate cancer cell ines? Eur J Nucl Med Mol Imaging 38, 1842-53.

Evans, M. J., Smith-Jones, P. M., Wongvipat, J., Navarro, V., Kim, S., Bander, N. H., Larson, S. M., and Sawyers, C. L. (2011) Noninvasive measurement of androgen receptor signaling with a positron-emitting radiopharmaceutical that targets prostate-specific membrane antigen. Proc Natl Acad Sci U S A 108, 9578-82.

Fair, W. R., Israeli, R. S., and Heston, W. D. (1997) Prostate-specific membrane antigen. Prostate 32, 140-8.

Fall, K., Garmo, H., Andren, O., Bill-Axelson, A., Adolfsson, J., Adami, H. O., Johansson, J. E., and Holmberg, L. (2007) Prostate-specific antigen levels as a predictor of lethal prostate cancer. J Natl Cancer Inst 99, 526-32.

Fortmuller, K., Alt, K., Gierschner, D., Wolf, P., Baum, V., Freudenberg, N., Wetterauer, U., Elsasser-Beile, U., and Buhler, P. (2011) Effective targeting of prostate cancer by lymphocytes redirected by a PSMA x CD3 bispecific single-chain diabody. Prostate 71, 588-96.

Fortuin, A. S., Deserno, W. M., Meijer, H. J., Jager, G. J., Takahashi, S., Debats, O. A., Reske, S. N., Schick, C., Krause, B. J., van Oort, I., Witjes, A. J., Hoogeveen, Y. L., van Lin, E. N., and Barentsz, J.

(56) References Cited

OTHER PUBLICATIONS

O. (2012) Value of PET/CT and MR lymphography in treatment of prostate cancer patients with lymph node metastases. Int J Radiat Oncol Biol Phys 84, 712-8.

Foss, C. A., Mease, R. C., Cho, S. Y., Kim, H. J., and Pomper, M. G. (2012) GCPII imaging and cancer. Curr Med Chem 19, 1346-59.

Foss, C. A., Mease, R. C., Fan, H., Wang, Y., Ravert, H. T., Dannals, R. F., Olszewski, R. T., Heston, W. D., Kozikowski, A. P., and Pomper, M. G. (2005) Radiolabeled small-molecule ligands for prostate-specific membrane antigen: in vivo imaging in experimental models of prostate cancer. Clin Cancer Res 11, 4022-8.

Franc, B. L., Cho, S. Y., Rosenthal, S. A., Cui, Y., Tsui, B., Vandewalker, K. M., Holz, A. L., Poonamallee, U., Pomper, M. G., and James, R. B. (2013) Detection and localization of carcinoma within the prostate using high resolution transrectal gamma imaging (TRGI) of monoclonal antibody directed at prostate specific membrane antigen (PSMA)-Proof of concept and initial imaging results. European Journal of Radiology 82, 1877-84.

Frigerio, B., Fracasso, G., Luison, E., Cingarlini, S., Mortarino, M., Coliva, A., Seregni, E., Bombardieri, E., Zuccolotto, G., Rosato, A., Colombatti, M., Canevari, S., and Figini, M. (2013) A single-chain fragment against prostate specific membrane antigen as a tool to build theranostic reagents for prostate cancer. Eur J Cancer 49, 2223-32.

Ghosh, A., and Heston, W. D. (2004) Tumor target prostate specific membrane antigen (PSMA) and its regulation in prostate cancer. J Cell Biochem 91, 528-39.

Giovacchini, G., Picchio, M., Coradeschi, E., Bettinardi, V., Gianolli, L., Scattoni, V., Cozzarini, C., Di Muzio, N., Rigatti, P., Fazio, F., and Messa, C. (2010) Predictive factors of [(11)C]choline PET/CT in patients with biochemical failure after radical prostatectomy. Eur J Nucl Med Mol Imaging 37, 301-9.

Benešová, et al., "Preclinical Evaluation of a Tailor-Made DOTA-Conjugated PSMA Inhibitor with Optimized Linker Moiety for Imaging and Endoradiotherapy of Prostate Cancer", jnm.snmjournals. org, Food & Drug Admin., The Journal of Nuclear Medicine, vol. 56, No. 6, 13 pages, Jun. 2015.

Benešová, et al., "Linker Modification Strategies To Control the Prostate-Specific Membrane Antigent (PSMA)—Targeting and Pharmacokinetic Properties of DOTA-Conjugated PSMA Inhibitors", Journal of Medicinal Chemistry, 2016, 59, ACS Publications, pp. 1761-1775.

International Search Report and Written Opinion of the International Searching Authority for counterpart Application No. PCT/US20/33584, dated Aug. 14, 2020.

Khreish, et al., "225Ac-PSMA-617/177 Lu-PSMA-617 tandem therapy of metastatic castration-resistant prostate cancer: pilot experience", European Journal of Nuclear Nedicine and Molecular Imaging (2020) 47:721-728.

Kratochwil, et al., "225Ac-PSMA-617 for PSMA-Targeted a-Radiation Therapy of Metastastic Castration-Resistant Prostate Cancer", Prostate Cancer Therapy, The Journal of Nuclear Medicine, vol. 57, No. 12, pp. 1941-1944, (Dec. 2016).

Lymperis, et al., "Radiometal-Dependent Biological Profile of the Radiolabeled Gastrin-Releasing Peptide Receptor Antagonist SB3 in Cancer Theranostics: Metabolic and Biodistribution Patterns Defined by Neprilysin", Bioconjugage Chem. 29, pp. 1774-1784, (2018).

Pratesi, et al., "Design and Solid Phase Synthesis of New DOTA Conjugated (+)-Biotin Dimers Planned to Develop Molecular Weight-Tuned Avidin Oligomers", Organic & Biomolecular Chemistry, RSCPublishing, J. Name, 00, 1-3, pp. 1-14, (2013).

Rosar, et al., "Molecular imaging and biochemical response assessment after a single cycle of [225Ac]Ac-PSMA-617 [177Lu]Lu-PSMA-617 tandem therapy in mCPRC patients who have progressed on [177Lu]Lu-PSMA-617 monotherapy", Theranostics 2021, vol. 11, Issue 9, (2021) 4050-4060.

Rossi, et al., "N-Nmoc-L-Glutamate, a New Caged Glutamate with High Chemical Stability and Low Pre-photolysis Activity", The Journal of Biological Chemistry, vol. 272, No. 52, pp. 32933-32939, (1997).

Communication Pursuant to Article 94(3) EPC for European Application No. 18172716.5-1110, dated Jun. 15, 2023.

Chatalic et al., "Towards Personalized Treatment of Prostate Cancer: PSMA I&T, a Promising Prostate-Specific Membrane Antigen-Targeted Theranostic Agent," Theranostics 2016, vol. 6, Issue 6, pp. 849-861.

Majer et al., "Discovery of Orally Available Prodrugs of the Glutamate Carboxypeptidase II (GCPII) Inhibitor 2-Phosphonomethylpentanedioic Acid (2-PMPA)," Journal of Medicinal Chemistry, 59, 2016, pp. 2810-2819.

Hamilou, et al., "Treatment of Castration-naive Metastatic Prostate Cancer", European Urology Focus, 3, www.europeanurology.com. eufocus; pp. 518-521, (2017).

Translation of Indonesian First Examination Report for counterpart Application No. P00202003113, dated Mar. 2, 2023.

Translation of Brazilian Technical Examination Report for counterpart Application No. BR112016008319-9, dated Apr. 25, 2023.

Office Action for counterpart Vietnam Patent AppIn 1-2016-01203, dated Dec. 27, 2022, with Translation.

Partial European Search Report for U.S. Appl. No. 19/167,560, dated Jul. 26, 2019.

Poster—"INOR 258—Urea based rhenium tricarbonyl dipeptide compounds as potential radiopharmaceuticals for PSMA imaging," 229th ACS National Meeting, San Diego, CA, Mar. 13-17, 2005.

Qatar Decision of Fulfillments and Amendment for counterpart Application No. QA/201604/00130, dated Apr. 28, 2020, with translation.

Rahbar et al., "Delayed response after repeated 177Lu-PSMA-617 radioligand therapy in patients with metastatic castration resistant prostate cancer," Eur J Nucl Med Mol Imaging (2018) 45: pp. 243-246.

Sartor et al., "Lutetium-177-PSMA-617 for Metastatic Castration-Resistent Prostate Cancer," The New England Journal of Medicine, downloaded from nejm.or at NovartisLibrary on Jun. 23, 2021, pp. 1-13.

Sathekge et al., "225Ac-PSMA-617 in chemotherapy-naïve patients with advanced prostate cancer: a pilot study," European Journal of Nuclear Medicine and Molecular Imaging (2019) 46:129-138.

Silverman, "The Organic Chemistry of Drug Design and Drug Action," 2nd Edition, pp. 1-97.

Silvola et al., "Imaging Session Title: Nuclear Cardiology: New Findings from Basic Science Studies," Abstract, http://cir.ahajournals.org/content/132/Suppl_3/A18873?cited-by=yes&legid=circulationaha; 2015.

Supplementary European Search Report for European U.S. Appl. No. 19/789,294, dated Nov. 18, 2021.

Violet et al., "Long-Term Follow-up and Outcomes of Retreatment in an Expanded 50-Patient Single-Center Phase II Prospective Trial of 177Lu-PSMA-617 Theranostics in Metastatic Castration-Resistant Prostate Cancer," The Journal of Nuclear Medicine, vol. 61, No. 6, Jun. 2020, pp. 857-865.

Wang et al., "Single Low-Dose Injection of Evans Blue Modified PSMA-617 Radioligand Therapy Eliminates Prostate- Specific Membrane Antigen Positive Tumors," Bioconjugate Chemistry, 2018, 29, pp. 3213-3221.

Wu et al., "A mild deprotection procedure for tert-butyl esters and tert-butyl ethers using ZnBR2 in methylene Chloride," Tetrahedron Letters 41 (2000), pp. 2847-2849.

Yadav et al., "177Lu-DKFZ-PSMA-617 therapy in metastatic castration resistant prostate cancer: safety, efficacy, and quality of life assessment," Eur J Nucl Med Mol Imaging (2017) 44:81-9.

National Centre of the Intellectual Property "Sakpatenti" of Georgia, "Documentary Conclusion and Search Report," issued in related Georgian Application No. AP 2014 15377—English-language Translation, dated Feb. 2017.

National Centre of the Intellectual Property "Sakpatenti" of Georgia, "Documentary Conclusion and Search Report," issued in related Georgian Application No. AP 2014 15377—English-language Translation, dated Mar. 2017.

(56) References Cited

OTHER PUBLICATIONS

Unfavorable Technical Opinion issued for the Brazilian patent application BR112016008319-9, in the name of Deutsches Krebsforschungszentrum (De), Ruprecht-Karls-Universität Heidelberg (DE), as published in the Industrial Property Magazine n°2706, from Nov. 16, 2022.
Translation of Indonesian Office Action for counterpart Application No. P00202003113, dated Mar. 2, 2023.
"4.2.G. Example of the Mechanisms of Enzyme Catalysis," Enzymes, Chapter 4, pp. 186-285.
"Chapter 5 Enzyme Inhibition and Inactivation," Enzymes, Chapter 5, pp. 286-385.
"Against," European Journal of Nuclear Medicine and Molecular Imaging, vol. 31, No. 5, May 2004.
Ahmadzadehfar, et al., Overall survival and response pattern of castration-resistant metastatic prostate cancer to multiple cycles of radioligand therapy using [177Lu]Lu-PSMA-617. Eur J Nucl Med Mol Imaging (2017) 44:1448-1454.
Brauer, et al., 177Lu-PSMA-617 radioligand therapy and outcome in patients with metastasized castration-resistant prostate cancer, Eur J Nucl Med Mol Imaging (2017) 44:1663-1670.
Canadian OA 100098 2ND OA Dated Aug. 15, 2017.
Chile Patent Application No. 201600883 Second Exam Report dated Nov. 1, 2019 With Eng. Translation.
Chinese Office Action for CN Application No. 201610184873.1 dated Jul. 24, 2018, with translation.
Clinical Trials Results Website, RESIST, 24 pages.
DNA-Interactive Agents, Chapter 6, Section 6.6, Problems, pp. 386-485.
Drug Discovery, Design and Development, General References, Section 2.3, pp. 98-184.
Drug Metabolism, Chapter 7, Prodrugs and Drug Delivery Systems, pp. 486-592.
Eurasian Patent Office for counterpart EA Application No. 201690495/28, dated Dec. 20, 2018, with English translation.
European Office Action for U.S. Appl. No. 13/855,243, dated May 27, 2019.
European Search Report for counterpart EP Application No. 18175078, dated Sep. 14, 2018.
European Search Report for counterpart EP Application No. 18184296, dated Jan. 23, 2019.
European Search Report for counterpart EP Application No. 18203547, dated Apr. 4, 2019.
First Office Action for counterpart Korean Application No. 1020167012314 dated Mar. 6, 2017.
Foss et al., "Abstract ID: 362 Synthesis and Validation of a Novel Small-Molecule Fluorescent Probe for PSMA Expression in Human Tumor Neovasculature," Molecular Imaging, vol. 4, No. 3, Jul. 2005, p. 321.
Greene et al., "Protective Groups in Organic Synthesis," Second Edition (front of book, copyright page, and Contents page).
Hofman et al., "[177Lu]Lu-PSMA-617 versus cabazitaxel in patients with metastatic castration-resistant prostate cancer (TheraP): a randomised, open-label, phase 2 trial," www.thelancet.com, Published online Feb. 11, 2021, https://doi.org/10.1016/S0140-6736(21)00237-3.
International Preliminary Report received in related application BR112016008319-9 dated Jan. 12, 2021.
International Search Report and Conclusion received from the Eurasian Patent Office in related Georgia Patent Application No. AP 2014 15377 dated Apr. 21, 2021.
International Search Report and Written Opinion for counterpart Application No. PCT/US19/51903, dated Dec. 2, 2019.
International Search Report and Written Opinion for counterpart Applicaton No. PCT/US21/18447, dated May 24, 2021.
International Search Report and Written Opinion for counterpart Application No. PCT/US2019/027720, dated Jun. 14, 2019.
International Search Report and Written Opinion for counterpart Application No. PCT/US08/73375, dated Nov. 17, 2008.
International Search Report and Written Opinion for counterpart Application No. PCT/US09/61049, dated Mar. 24, 2010.
International Search Report and Written Opinion for counterpart Application No. PCT/US09/61067, dated Jun. 17, 2010.
International Search Report and Written Opinion for counterpart Application No. PCT/US11/26238, dated Apr. 27, 2011.
International Search Report and Written Opinion for counterpart Application No. PCT/US13/70007, dated Mar. 5, 2014.
International Search Report and Written Opinion for counterpart Application No. PCT/US2014/065467, dated Apr. 15, 2015.
International Search Report and Written Opinion for counterpart Application No. PCT/US16/12653, dated Mar. 11, 2016.
Israeli Office Action for counterpart Application No. 245113, dated Jan. 10, 2019, with English translation.
Japanese Notice of Reasons for Refusal for Application No. 2018-208786, dated Oct. 1, 2019, with translation.
Japanese Notice of Reasons for Refusal for Application No. 2017-210775, dated Nov. 6, 2018, with translation.
Japanese Notice of Reasons for Rejection for JP Application No. 2018-193272, dated Jul. 16, 2019, with translation.
Jemaa et al., "A Comparison of the Biological Features of Prostate Cancer with (PSA+, PSMA+) Profile according to RKIP," BioMed Research International, vol. 2013, Article ID 409179, 7 pages, Http://dx.doi.org/10.1155/2013/409179.
Kratochwil et al., "PSMA-Targeted Radionuclide Therapy of Metastic Castration-Resistant Prostrate Cancer with 177Lu-Labeled PSMA-617," The Journal of Nuclear Medicine, vol. 57, No. 8, Aug. 2016, pp. 1170-1176.
Indonesian Office Action for counterpart Application No. P00201603202, dated Feb. 18, 2020, with translation.
Lau et al., "Bench to Bedside: Albumin Binders for Improved Cancer Radioligand Therapies," Bioconjugate Chemistry, 2019, 30, pp. 487-502.
Liu et al., "A targeted low molecular weight near-infrared fluorescent probe for prostate cancer," Bioorganic & Medicinal Chemistry Letters, 20 (2010) pp. 7124-7126.
Malaysian Office Action for counterpart MY Application No. PI 2015001086, dated Apr. 3, 2019.
Meienhofer et al., "Solid-Phase Synthesis with Attachment of Peptide to Resin through an Amino Acid Side Chain: [8-Lysine]-Vasopressin," Proc. Nat. Acad. Sci. USA, vol. 68, No. 5, May 1971, pp. 1006-1009.
Mexican Office Action for counterpart MX Application No. MX/a/2016/005013, dated Jul. 24, 2019 with translation.
Mexican Office Action for counterpart MX Application No. MX/a/2016/005013, dated Jan. 30, 2020, with Eng. Translation.
Office Action for counterpart Canadian Application No. 2924360 dated Nov. 12, 2020.

\* cited by examiner

MB17

PET-imaging

Time-activity-curves

Organ distribution at 1 h post injection

|  | MB17 | | | MB17 blocked | | |
|---|---|---|---|---|---|---|
|  | %ID/g | SD | n | %ID/g | SD | n |
| Blood | 1.08 | 0.25 | 3 | 1.24 | 0.92 | 3 |
| Heart | 0.53 | 0.15 | 3 | 0.49 | 0.27 | 3 |
| Lung | 1.41 | 0.41 | 3 | 1.10 | 0.53 | 3 |
| Spleen | 2.13 | 0.16 | 3 | 0.53 | 0.36 | 3 |
| Liver | 1.17 | 0.10 | 3 | 0.73 | 0.07 | 3 |
| Kidney | 113.34 | 24.45 | 3 | 2.38 | 1.40 | 3 |
| Muscle | 0.50 | 0.07 | 3 | 0.24 | 0.09 | 3 |
| Intestine | 0.46 | 0.13 | 3 | 0.35 | 0.23 | 3 |
| Brain | 0.12 | 0.01 | 3 | 0.07 | 0.01 | 3 |
| LNCaP Tumor | 8.47 | 4.09 | 3 | 0.98 | 0.32 | 3 |

MB04

PET-imaging

Time-activity-curves

| 24 h | %ID/g | SD | n |
|---|---|---|---|
| Blood | 0,01 | 0,00 | 5 |
| Heart | 0,02 | 0,01 | 5 |
| Lung | 0,11 | 0,13 | 5 |
| Spleen | 0,13 | 0,05 | 5 |
| Liver | 0,08 | 0,03 | 5 |
| Kidney | 2,13 | 1,36 | 5 |
| Muscle | 0,02 | 0,01 | 5 |
| Intestine | 0,02 | 0,01 | 5 |
| Brain | 0,05 | 0,03 | 5 |
| LNCaP Tumor | 10,58 | 4,50 | 5 |

MB-17 vs MB-17.D

PET-imaging after 2 hours post injection, comparison of whole-body scan

LABELED INHIBITORS OF PROSTATE SPECIFIC MEMBRANE ANTIGEN (PSMA) AS AGENTS FOR THE TREATMENT OF PROSTATE CANCER

RELATED APPLICATIONS AND INCORPORATION BY REFERENCE

This application is a divisional of U.S. application Ser. No. 16/551,198, filed Aug. 26, 2019, which is a divisional of U.S. application Ser. No. 16/114,988, filed Aug. 28, 2018, which is a continuation of U.S. application Ser. No. 15/131,118 filed Apr. 18, 2016, which is a continuation-in-part application of international patent application Serial No. PCT/EP2014/002808 filed Oct. 17, 2014, which published as PCT Publication No. WO 2015/055318 on Apr. 23, 2015, which claims benefit of European patent application Serial Nos. 13004991.9 filed Oct. 18, 2013, and 14175612.2 filed Jul. 3, 2014.

The foregoing applications, and all documents cited therein are incorporated herein by reference in their entireties.

FIELD OF THE INVENTION

The present invention generally relates to the field of radiopharmaceuticals and their use in nuclear medicine as tracers, imaging agents and for the treatment of various disease states of prostate cancer.

BACKGROUND OF THE INVENTION

Prostate cancer (PCa) is the leading cancer in the US and European population. At least 1-2 million men in the western hemisphere suffer from prostate cancer and it is estimated that the disease will strike one in six men between the ages of 55 and 85. There are more than 300.000 new cases of prostate cancer diagnosed each year in USA. The mortality from the disease is second only to lung cancer. Currently anatomic methods, such as computed tomography (CT), magnetic resonance (MR) imaging and ultrasound, predominate for clinical imaging of prostate cancer. An estimated $2 billion is currently spent worldwide on surgical, radiation, drug therapy and minimally invasive treatments. However, there is presently no effective therapy for relapsing, metastatic, androgen-independent prostate cancer.

A variety of experimental low molecular weight PCa imaging agents are currently being pursued clinically, including radiolabeled choline analogs [$^{18}$F]fluorodihydrotestosterone ([$^{18}$F]FDHT), anti-1-amino-3-[$^{18}$F]fluoro-cyclobutyl-1-carboxylic acid (anti[18F]F-FACBC, [$^{11}$C]acetate and 1-(2-deoxy-2-[$^{18}$F]fluoro-L-arabinofuranosyl)-5-methyluracil (—[$^{18}$F]FMAU) (Scher, B.; et al. Eur J Nucl Med Mol Imaging 2007, 34, 45-53; Rinnab, L.; et al. BJU Int 2007, 100, 786,793; Reske, S. N.; et al. J Nucl Med 2006, 47, 1249-1254; Zophel, K.; Kotzerke, J. Eur J Nucl Med Mol Imaging 2004, 31, 756-759; Vees, H.; et al. BJU Int 2007, 99, 1415-1420; Larson, S. M.; et al. J Nucl Med 2004, 45, 366-373; Schuster, D. M.; et al. J Nucl Med 2007, 48, 56-63; Tehrani, O. S.; et al. J Nucl Med 2007, 48, 1436-1441). Each operates by a different mechanism and has certain advantages, e.g., low urinary excretion for [$^{11}$C]choline, and disadvantages, such as the short physical half-life of positron-emitting radionuclides.

It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. A promising new series of low molecular weight imaging agents targets the prostate-specific membrane antigen (PSMA) (Mease R. C. et al. Clin Cancer Res. 2008, 14, 3036-3043; Foss, C. A.; et al. Clin Cancer Res 2005, 11, 4022-4028; Pomper, M. G.; et al. Mol Imaging 2002, 1, 96-101; Zhou, J.; et al. Nat Rev Drug Discov 2005, 4, 1015-1026; WO 2013/022797).

PSMA is a trans-membrane, 750 amino acid type II glycoprotein that has abundant and restricted expression on the surface of PCa, particularly in androgen-independent, advanced and metastatic disease (Schulke, N.; et al. Proc Natl Acad Sci USA 2003, 100, 12590-12595). The latter is important since almost all PCa become androgen independent over the time. PSMA possesses the criteria of a promising target for therapy, i.e., abundant and restricted (to prostate) expression at all stages of the disease, presentation at the cell surface but not shed into the circulation and association with enzymatic or signaling activity (Schulke, N.; et al. Proc. Natl. Acad. Sci. USA 2003, 100, 12590-12595). The PSMA gene is located on the short arm of chromosome 11 and functions both as a folate hydrolase and neuropeptidase. It has neuropeptidase function that is equivalent to glutamate carboxypeptidase II (GCPII), which is referred to as the "brain PSMA", and may modulate glutamatergic transmission by cleaving N-acetylaspartylglutamate (NAAG) to N-acetylaspartate (NAA) and glutamate (Nan, F.; et al. J Med Chem 2000, 43, 772-774). There are up to $10^6$ PSMA molecules per cancer cell, further suggesting it as an ideal target for imaging and therapy with radionuclide-based techniques (Tasch, J.; et al. Crit Rev Immunol 2001, 21, 249-261).

The radio-immunoconjugate of the anti-PSMA monoclonal antibody (mAb) 7E11, known as the PROSTASCINT® scan, is currently being used to diagnose prostate cancer metastasis and recurrence. However, this agent tends to produce images that are challenging to interpret (Lange, P. H. PROSTASCINT scan for staging prostate cancer. Urology 2001, 57, 402-406; Haseman, M. K.; et al. Cancer Biother Radiopharm 2000, 15, 131-140; Rosenthal, S. A.; et al. Tech Urol 2001, 7, 27-37). More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability of the monoclonal antibody in solid tumors.

The selective targeting of cancer cells with radiopharmaceuticals, either for imaging or therapeutic purposes is challenging. A variety of radionuclides are known to be useful for radio-imaging or cancer radiotherapy, including $^{111}$In, $^{90}$Y, $^{68}$Ga, $^{177}$Lu, $^{99m}$Tc, $^{123}$I and $^{131}$I. Recently it has been shown that some compounds containing a glutamate-urea-glutamate (GUG) or a glutamate-urea-lysine (GUL) recognition element linked to a radionuclide-ligand conjugate exhibit high affinity for PSMA.

Citation or identification of any document in this application is not an admission that such document is available as prior art to the present invention.

SUMMARY OF THE INVENTION

New agents that will enable rapid visualization of prostate cancer and specific targeting to allow radiotherapy present are needed.

Thus, the object of the present invention is to develop ligands that interact with PSMA and carry appropriate radionuclides which provide a promising and novel targeting option for the detection, treatment and management of prostate cancer.

The solution of said object is achieved by providing the embodiments characterized in the claims.

The inventors found new compounds which are useful radiopharmaceuticals and their use in nuclear medicine as tracers, imaging agents and for the treatment of various disease states of prostate cancer.

The novel imaging agents with structural modifications in the linker region have improved tumor targeting properties and pharmacokinetics. The pharmacophore presents three carboxylic groups able to interact with the respective side chains of PSMA and an oxygen as part of zinc complexation in the active center. Besides these obligatory interactions, the inventors were able to optimize the lipophilic interactions in the linker region.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
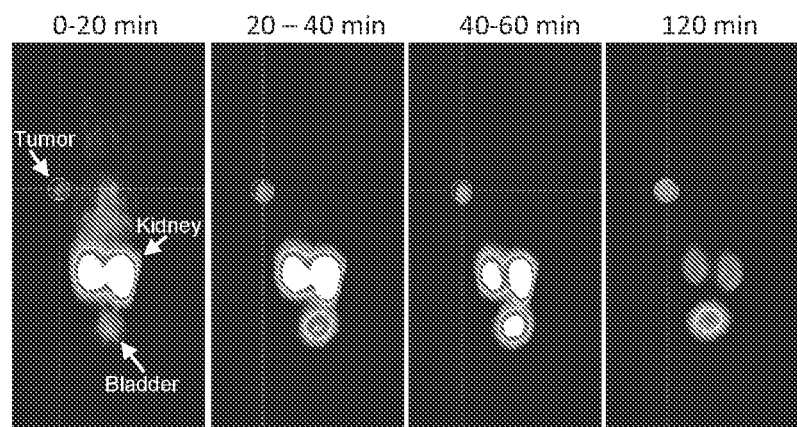
FIG. 1: PET—Imaging of MB17. Whole-body coronal microPET images of an athymic male nude mice bearing LNCaP tumor xenografts. The tumor-targeting efficacy and pharmacokinetic properties of [$^{68}$Ga]MB17 were evaluated by dynamic microPET scans. Approximately 15 MBq/mouse were injected. Graph A shows the respective time-activity-curves of kidney and balder and graph B the respective time-activity-curves of heart, muscle and tumor. The values are expressed as mean SUV (standardized uptake values).
Figure 1:
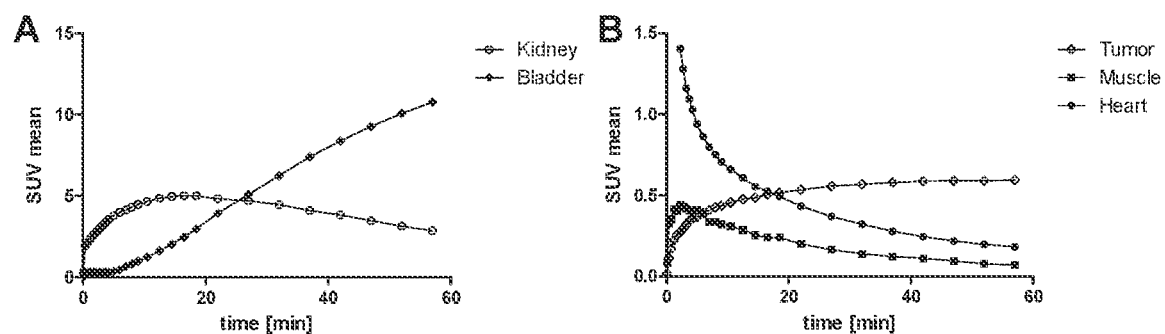

The present invention relates to radiopharmaceuticals and their use in nuclear medicine as tracers, imaging agents and for the treatment of various disease states of prostate cancer.

Thus, the present invention concerns compounds that are represented by the general Formulae (Ia) or (Ib):

Formula (Ia)

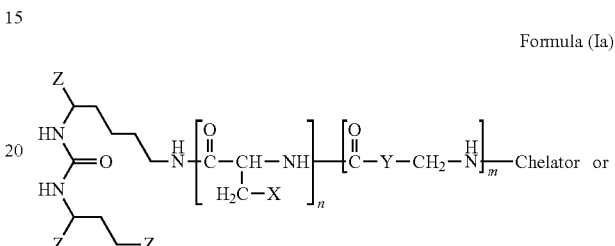

Formula (Ib)

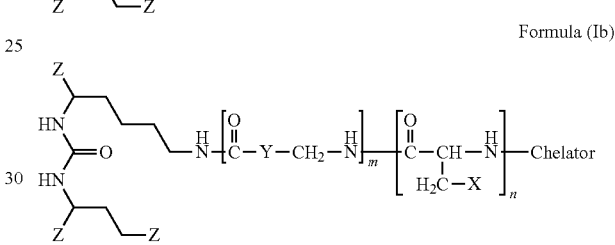

with:

| | |
|---|---|
| n: | 0, 1 |
| m: | 1, 2, 3, 4 |
| Z: | —CO$_2$H, —SO$_2$H, —SO$_3$H, —SO$_4$H, —PO$_2$H, —PO$_3$H, —PO$_4$H$_2$ |
| X: | Naphthyl, Phenyl, Biphenyl, Indolyl (=2,3-benzopyrrolyl), Benzothiazolyl |
| Y: | Aryl, Alkylaryl, Cyclopentyl, Cyclohexyl, Cycloheptyl |
| Chelator radical of: | 1,4,7,10-tetraazacyclododecane-N,N',N'',N'''-tetraacetic acid (DOTA), N,N''-bis[2-hydroxy-5-(carboxyethyl)benzyl]ethylenediamine-N,N''-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)pentanedioic acid (DOTAGA), 1,4,7-triazacyclononane phosphinic acid (TRAP), 1,4,7-triazacyclononane-1-[methyl(2-carboxyethyl)phosphinic acid]-4,7-bis[methyl(2-hydroxymethyl)phosphinic acid] (NOPO), 3,6,9,15-tetraazabicyclo[9.3.1]pentadeca-1(15),11,13-triene-3,6,9-triacetic acid (PCTA), N'-{5-[Acetyl(hydroxy)amino] pentyl}-N-[5-({4-[(5-aminopentyl)(hydroxy)amino]-4-oxobutanoyl}amino)pentyl]-N-hydroxysuccinamide (DFO), Diethylenetriaminepentaacetic acid (DTPA) Trans-cyclohexyl-diethylenetriaminepentaacetic acid (CHX-DTPA) 1-oxa-4,7,10-triazacyclododecane-4,7,10-triacetic acid (oxo-Do3A) p-isothiocyanatobenzyl-DTPA (SCN-Bz-DTPA) 1-(p-isothiocyanatobenzyl)-3-methyl-DTPA (1B3M) 2-(p-isothiocyanatobenzyl)-4-methyl-DTPA (1M3B) 1-(2)-methyl-4-isocyanatobenzyl-DTPA (MX-DTPA) |

If not stated otherwise, in the present invention the "alkyl" residue (preferably: $C_1$ to $C_{10}$) can be linear or branched, unsubstituted or substituted. Preferred alkyl residues are methyl, ethyl, n-propyl, iso-propyl, n-butyl, tert-butyl, n-pentanyl, n-hexanyl. The same also applies to the corresponding cycloalkyl compounds having preferably 3 to 10 carbon atoms.

"Aryl" refers to an aromatic monocyclic or polycyclic ring system having 6 to 14 carbon atoms, preferably 6 to 10 carbon atoms. The aryl group can be substituted, where appropriate, with one or several ring substituents, like alkyl groups. Preferred aryl groups are phenyl, benzyl or naphthyl.

Although it is preferred that the Z-Group is —$CO_2H$ it may be easily replaced with biosteric replacements such as —$SO_2H$, —$SO_3H$, —$SO_4H$, —$PO_2H$, —$PO_3H$, —$PO_4H_2$, see e g. "The Practice of Medicinal Chemistry" (Academic Press New York, 1996), page 203.

Within the meaning of the invention, all residues are considered combinable unless stated otherwise in the definition of the residues. All conceivable subgroupings thereof are considered to be disclosed.

In a preferred embodiment, the motif specifically binding to cell membranes of neoplastic cells is a motif specifically binding to cell membranes of cancerous cells, preferably wherein said motif may comprise a prostate-specific membrane antigen (PSMA), in particular wherein said PSMA may comprise a glutamate-urea-lysine motif according to the following formula in Scheme 1.

Thus, preferred molecules of the present invention consist of three principal components (Scheme 1): the hydrophilic PSMA binding motif (radical of Glu-Urea-Lys; =Glu-NH—CO—NH-Lys), a variable linker and the chelator which is preferably a radical of DOTA.

Scheme 1: Structure of Preferred Compounds of the Present Invention

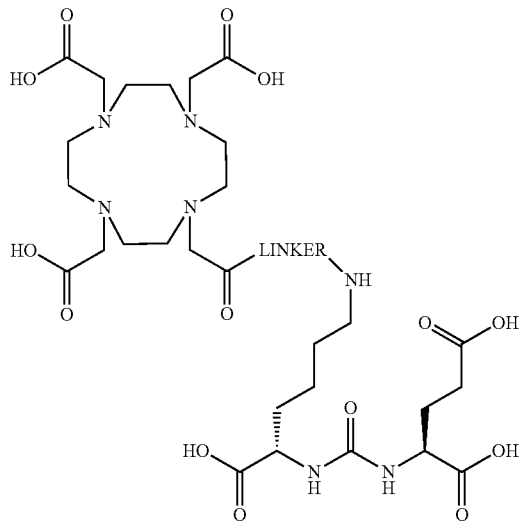

The different preferred linkers are shown below, wherein R=radical of Glu-urea-Lys and R'=radical of DOTA (as a preferred example for the chelator), as shown above.

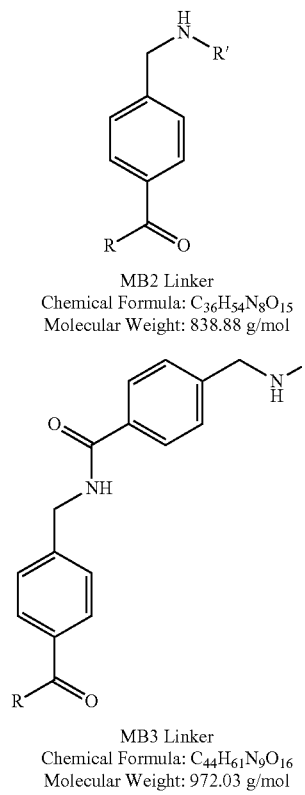

MB2 Linker
Chemical Formula: $C_{36}H_{54}N_8O_{15}$
Molecular Weight: 838.88 g/mol

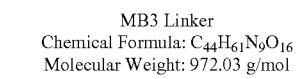

MB3 Linker
Chemical Formula: $C_{44}H_{61}N_9O_{16}$
Molecular Weight: 972.03 g/mol

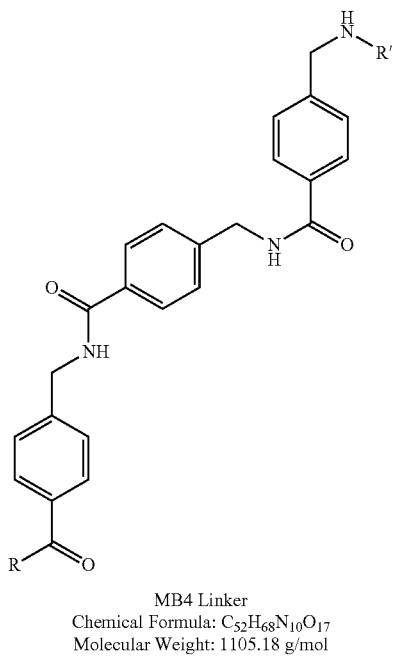

MB4 Linker
Chemical Formula: $C_{52}H_{68}N_{10}O_{17}$
Molecular Weight: 1105.18 g/mol

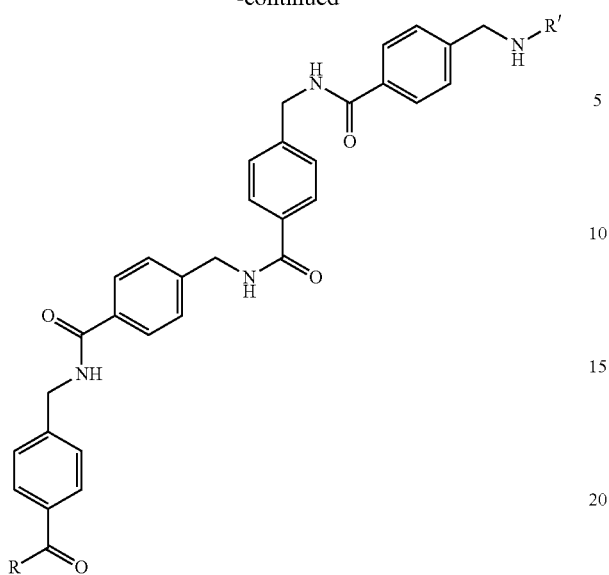
MB10 Linker
Chemical Formula: $C_{65}H_{70}N_{11}O_8$
Molecular Weight: 1238.33 g/mol
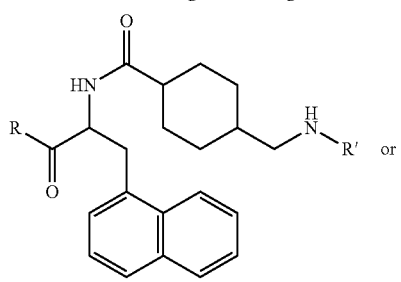 or
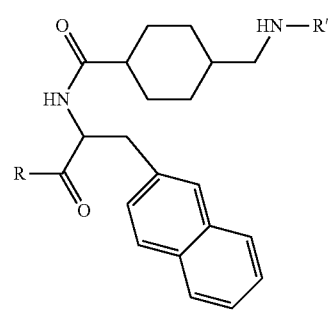
MB 17 Linker
Chemical Formula: $C_{49}H_{71}N_9O_{16}$
Molecular Weight: 1042.16 g/mol
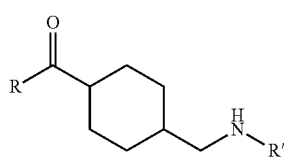
MB22 Linker
Chemical Formula: $C_{36}H_{60}N_8O_{15}$
Molecular Weight: 844.92 g/mol
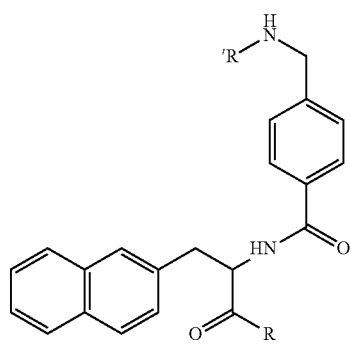
MB24
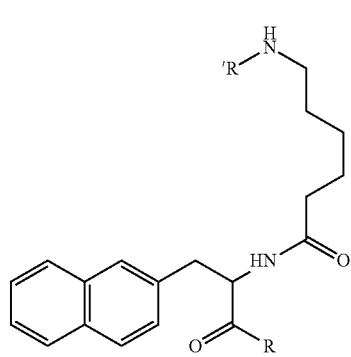
MB25
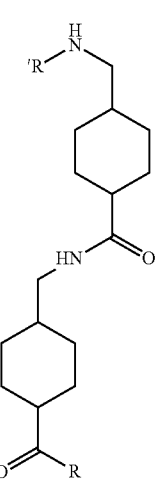
MB31

MB33
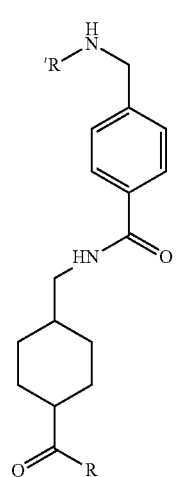
MB35
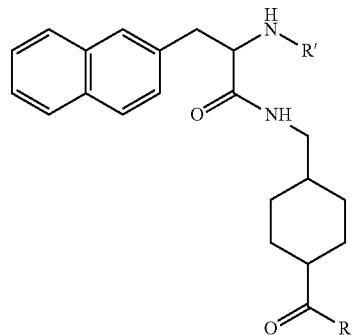
Preferred compounds of the present invention are e.g.
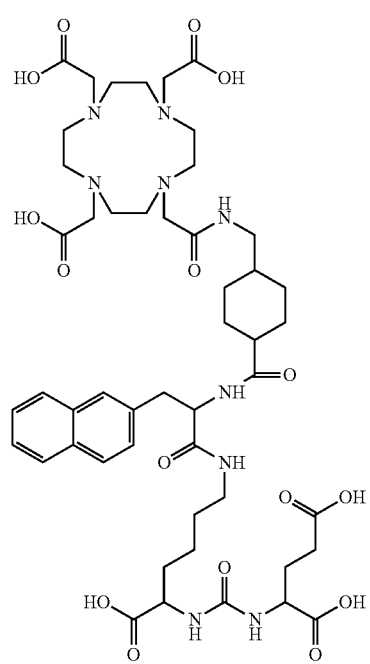
or
MB 17
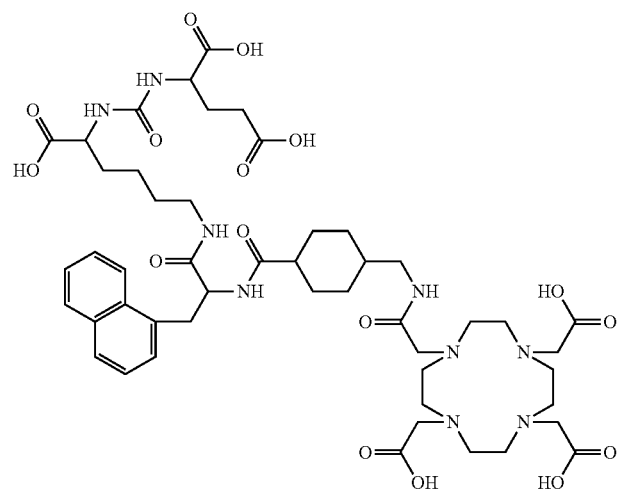

MB 4
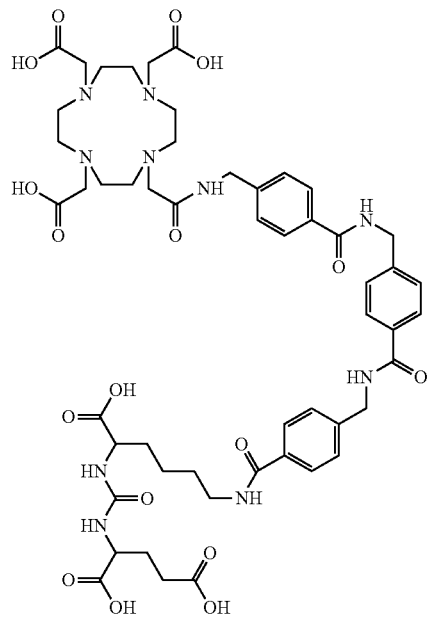
MB 10
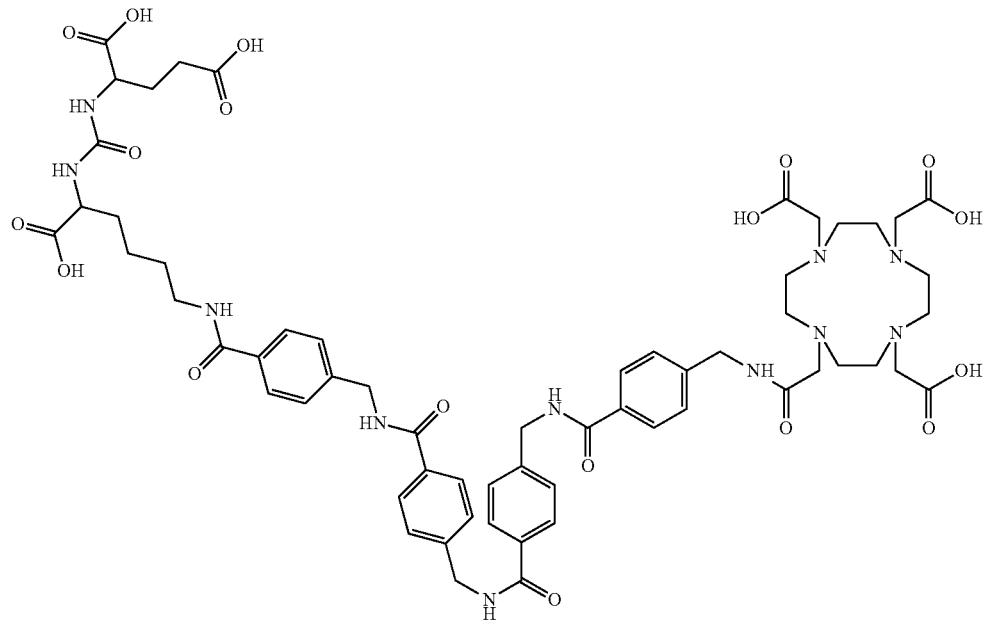

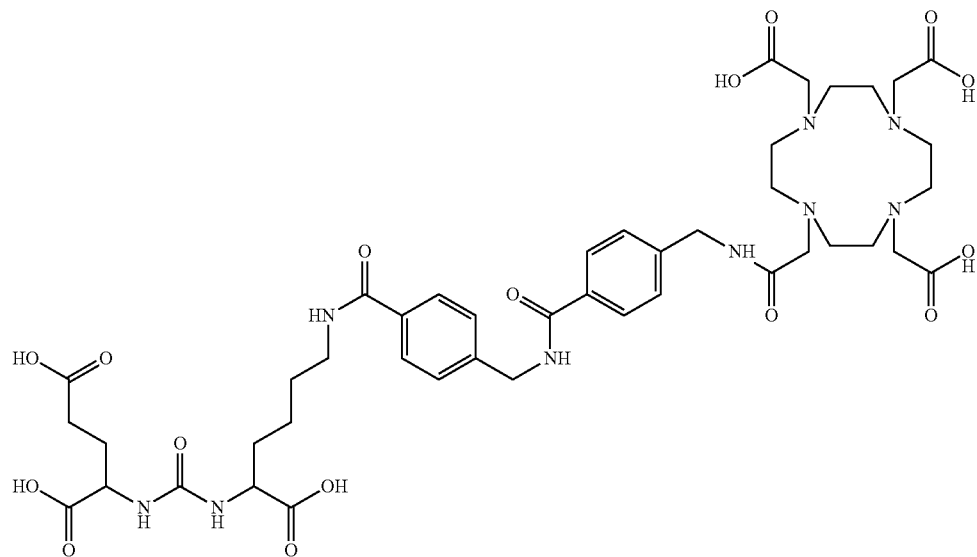
MB 3
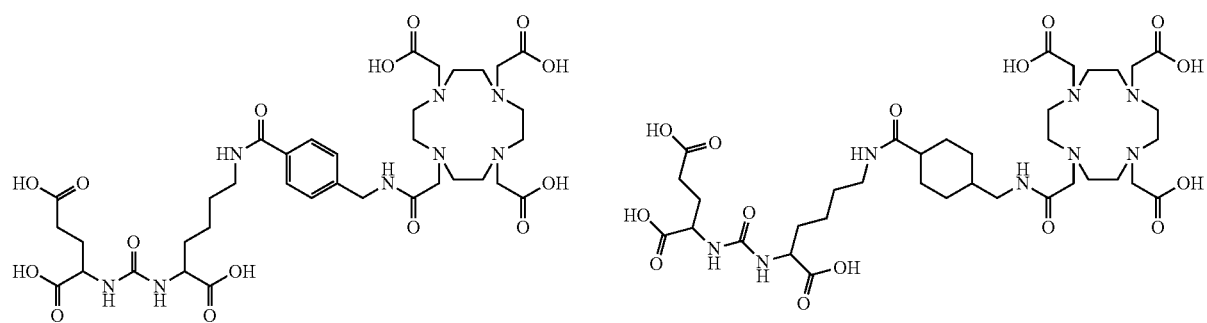
MB 2
MB 22
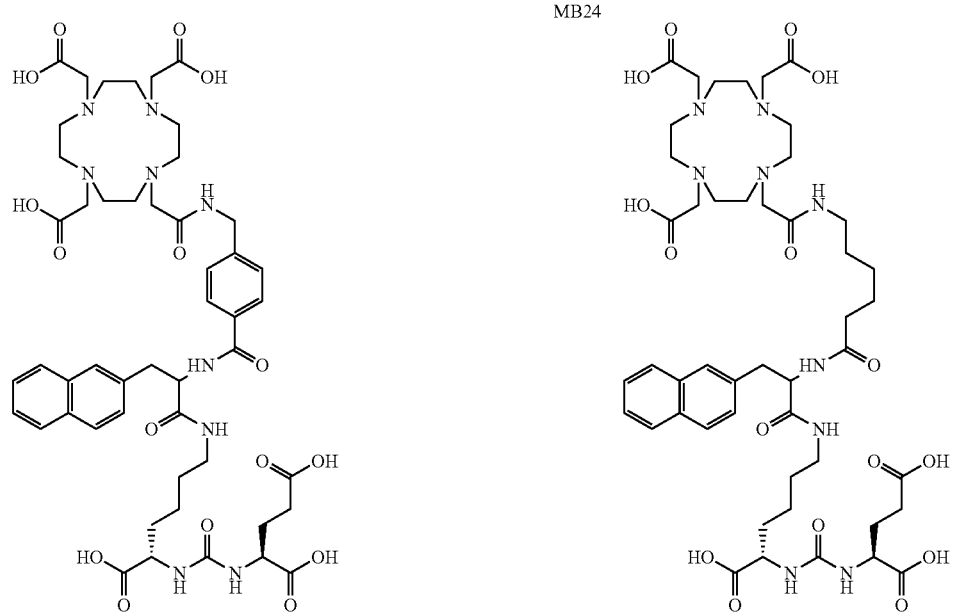
MB24
MB25

-continued

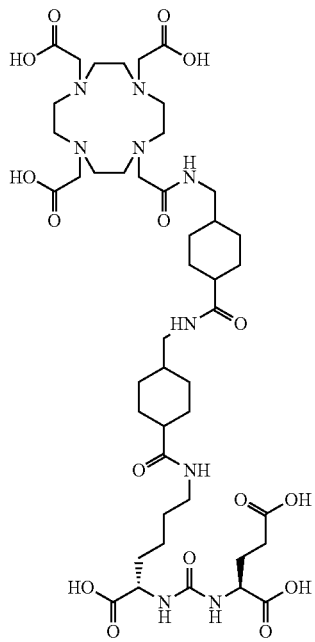
MB31

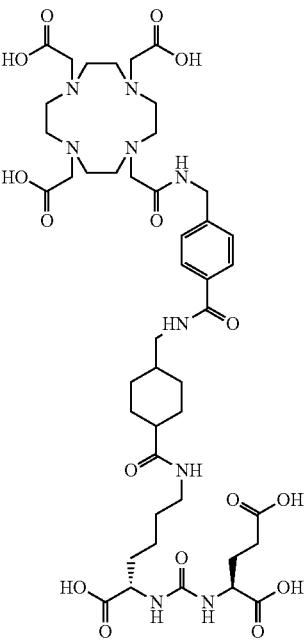
MB33

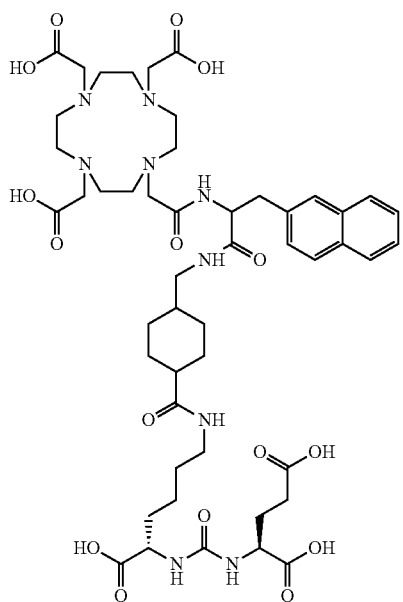
MB35

The invention also relates to pharmaceutically acceptable salts of the compounds of general formula (Ia) and/or (Ib). The invention also relates to solvates of the compounds, including the salts as well as the active metabolites thereof and, where appropriate, the tautomers thereof according to general formula (Ia) and/or (Ib) including prodrug formulations.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, carbonate, chloride, gluconate, glutamate, lactate, laurate, malate or tartrate.

The term "prodrug" refers to a precursor of a drug that is a compound which upon administration to a patient, must undergo chemical conversion by metabolic processes before becoming an active pharmacological agent. Illustrative prodrugs of compounds in accordance with Formula (Ia) and/or (Ib) are esters and amides, preferably alkyl esters of fatty acid esters. Prodrug formulations here may comprise all substances which are formed by simple transformation including hydrolysis, oxidation or reduction either enzymatically, metabolically or in any other way. A suitable prodrug contains e.g. a substance of general formula (Ia) and/or (Ib) bound via an enzymatically cleavable linker (e.g. carbamate, phosphate, N-glycoside or a disulfide group) to a dissolution-improving substance (e.g. tetraethylene glycol, saccharides, formic acids or glucuronic acid, etc.). Such a prodrug of a compound according to the invention can be applied to a patient, and this prodrug can be transformed into a substance of general formula (Ia) and/or (Ib) so as to obtain the desired pharmacological effect.

Some compounds of Formula (Ia) and/or (Ib) are encompassed in form of the racemates, their enantiomers and optionally in form of their diastereomers and all possible mixtures thereof.

According to the invention all chiral C-atoms shall have D- and/or L-configuration; also combinations within one compound shall be possible, i.e. some of the chiral C-atoms may be D- and others may be L-configuration.

The obtained compounds can be optionally separated by known methods (e.g. Allinger, N. L. und Elliel E. L. in "Topics in Stereochemistry" Vol. 6, Wiley Interscience, 1971) in their enantiomers and/or diastereomers. One possible method of enantiomeric separation is the use of chromatography.

The invention also relates to pharmaceutical preparations which contain a therapeutically effective amount of the active ingredients (compound according to the invention of formula (Ia) or (Ib) together with organic or inorganic solid or liquid, pharmaceutically acceptable carriers which are suited for the intended administration and which interact with the active ingredients without drawbacks.

The phrase "pharmaceutically acceptable" is employed herein to refer to those compounds, material, compositions, and/or dosage forms which are, within the scope of sound medical judgment, suitable for use in contact with the tissues of a patient without excessive toxicity, irritation, allergic response, or other problem or complication, commensurate with a reasonable benefit/risk ratio.

A "patient" includes an animal, such as a human, monkey, cow, horse, cat or dog. The animal can be a mammal such as a non-primate and a primate (e.g., monkey and human). In one embodiment, a patient is a human being.

In general, the Formula (Ia) or (Ib) compound or pharmaceutical compositions thereof, may be administered orally or via a parenteral route, usually injection or infusion.

A "parenteral administration route" means modes of administration other than enteral and topical administration, usually by injection, and includes, without limitation, intravenous, intramusclular, intraarterial, intrathecal, intracapsular, intraorbital, intracardiac, intradermal, intraperitoneal, transtracheal, subcutaneous, subcuticular, intraarticluare, subcapsular, subarachnoid, intraspinal and intrasternal injection and infusion.

The dosage of the compounds according to the invention is determined by the physician on the basis of the patient-specific parameters, such as age, weight, sex, severity of the disease, etc. The dosage is preferably from 0.00001 mg/kg to 100 mg/kg body weight, preferably from 0.001 to 50 mg/kg body weight and most preferably from 0.01 to 10 mg/kg body weight.

Corresponding to the kind of administration, the medicament is suitably formulated, e.g. in the form of solutions or suspensions, simple tablets or dragees, hard or soft gelatine capsules, suppositories, ovules, preparations for injection, which are prepared according to common galenic methods.

The compounds according to the invention can be formulated, where appropriate, together with further active substances and with excipients and carriers common in pharmaceutical compositions, e.g.—depending on the preparation to be produced—talcum, gum arabic, lactose, starch, magnesium stearate, cocoa butter, aqueous and non-aqueous carriers, fatty bodies of animal or vegetable origin, paraffin derivatives, glycols (in particular polyethylene glycol), various plasticizers, dispersants or emulsifiers, pharmaceutically compatible gases (e.g. air, oxygen, carbon dioxide, etc.), preservatives.

In order to produce liquid preparations, additives, such as sodium chloride solution, ethanol, sorbitol, glycerine, olive oil, almond oil, propylene glycol or ethylene glycol, can be used.

When solutions for infusion or injection are used, they are preferably aqueous solutions or suspensions, it being possible to produce them prior to use, e.g. from lyophilized preparations which contain the active substance as such or together with a carrier, such as mannitol, lactose, glucose, albumin and the like. The ready made solutions are sterilized and, where appropriate, mixed with excipients, e.g. with preservatives, stabilizers, emulsifiers, solubilizers, buffers and/or salts for regulating the osmotic pressure. The sterilization can be obtained by sterile filtration using filters having a small pore size according to which the composition can be lyophilized, where appropriate. Small amounts of antibiotics can also be added to ensure the maintenance of sterility.

The phrases "effective amount" or "therapeutically-effective amount" as used herein means that amount of a compound, material, or composition which may comprise a compound of the invention, or other active ingredient which is effective for producing some desired therapeutic effect in at least a sub-population of cells in an animal at a reasonable benefit/risk ratio applicable to any medical treatment. A therapeutically effective amount with respect to a compound of the invention means that amount of therapeutic agent alone, or in combination with other therapies, that provides a therapeutic benefit in the treatment of prevention of a disease. Used in connection with a compound of the invention, the term can encompass an amount that improves overall therapy, reduces or avoids symptoms or causes of disease, or enhances the therapeutic efficacy of or synergies with another therapeutic agent.

As used herein, the terms "treating" or "treatment" is intended to encompass also diagnosis, prophylaxis, prevention, therapy and cure.

The terms "prevent", "preventing," and "prevention" refer to the prevention of the onset, recurrence, or spread of the disease in a patient resulting from the administration of a prophylactic or therapeutic agent.

Depending on whether the inventive Formula (Ia) and/or (Ib) compounds are to be used as radio-imaging agents or radio-pharmaceuticals different radionuclides are complexed to the chelator. Illustrative radionuclides include, for example, $^{89}$Zr, $^{44}$Sc, $^{111}$In, $^{90}$Y, $^{66}$Ga, $^{67}$Ga, $^{68}$Ga, $^{177}$Lu, $^{99m}$Tc, $^{61}$Cu, $^{62}$Cu, $^{64}$Cu, $^{67}$Cu, $^{149}$Tb, $^{152}$Tb, $^{155}$Tb, $^{161}$Tb, $^{153}$Gd, $^{155}$Gd, $^{157}$Gd, $^{213}$Bi, $^{225}$Ac, $^{230}$U, $^{223}$Ra, $^{165}$Er and Fe. According to one aspect of this invention, the radionuclide is $^{111}$In, $^{90}$Y, $^{68}$Ga, $^{64}$Cu, $^{153}$Gd, $^{155}$Gd, $^{213}$Bi, $^{225}$Ac, Fe, or $^{177}$Lu.

As noted above, complexes of the compounds according Formula (Ia) or (Ib) may contain one or more radionuclides which are suitable for use as radio-imaging agents or as therapeutics for the treatment of rapidly proliferating cells, for example, PSMA expressing prostate cancer cells. According to the present invention they are called "metal complexes" or "radiopharmaceuticals".

Preferred imaging methods are positron emission tomography (PET) or single photon emission computed tomography (SPECT).

Accordingly, in one embodiment, a pharmaceutical composition is provided including a complex that includes a radionuclide and a compound of Formula (Ia) or Formula (Ib), a salt, solvate, stereoisomer, or tautomer thereof, and a pharmaceutically acceptable carrier.

According to another aspect, a pharmaceutical composition is provided, which is suitable for in vivo imaging and radiotherapy. Suitable pharmaceutical compositions may contain a radio imaging agent, or a radiotherapeutic agent that has a radionuclide either as an element, i.e. radioactive iodine, or a radioactive metal chelate complex of the compound of Formula (Ia) and/or (Ib) in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc; sterile water physiological saline; and balanced ionic solutions containing chloride and or dicarbonate salts or normal blood plasma cautions such as calcium potassium, sodium and magnesium.

The concentration of the imaging agent or the therapeutic agent in the radiological vehicle should be sufficient to provide satisfactory imaging. For example, when using an aqueous solution, the dosage is about 1.0 to 100 millicuries. The actual dose administered to a patient for imaging or therapeutic purposes, however, is determined by the physician administering treatment. The imaging agent or therapeutic agent should be administered so as to remain in the patient for about 1 hour to 10 days, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable imaging or scanning machine, such as a tomograph or gamma camera. In certain embodiments, a method of imaging a region in a patient includes the steps of: (i) administering to a patient a diagnostically effective amount of a compound complexed with a radionuclide; exposing a region of the patient to the scanning device; and (ii) obtaining an image of the region of the patient. In certain embodiments of the region imaged is the head or thorax. In other embodiments, the compounds and complexes of Formula I(a) and/or (Ib) target the PSMA protein.

Thus, in some embodiments, a method of imaging tissue such as spleen tissue, kidney tissue, or PSMA-expressing tumor tissue is provided including contacting the tissue with a complex synthesized by contacting a radionuclide and a Formula (Ia) and/or Formula (Ib) compound.

The amount of the compound of the present invention, or a formulation which may comprise a complex of a metal and a compound according to Formula (Ia) and/or (Ib), or its salt, solvate, stereoisomer, or tautomer that is administered to a patient depends on several physiological factors that are routinely used by the physician, including the nature of imaging to be carried out, tissue to be targeted for imaging or therapy and the body weight and medical history of the patient to be imaged or treated using a radiopharmaceutical.

Accordingly in another aspect, the invention provides a method for treating a patient by administering to a patient a therapeutically effective amount of a Formula (Ia) and/or (Ib) compound complexed to a radionuclide, or a pharmaceutically acceptable salt or solvate of the complex to treat a patient suffering from a cell proliferative disease or disorder. Specifically, the cell proliferative disease or disorder to be treated or imaged using a compound, pharmaceutical composition or radiopharmaceutical in accordance with this invention is a cancer, for example, prostate cancer and/or prostate cancer metastasis in e.g. lung, liver, kidney, bones, brain, spinal cord, bladder, etc.

The synthesis of the compounds of the present invention is described in detail in the example section. An overview of the synthesis is exemplified in Scheme 2 concerning DOTA conjugated-PSMA inhibitors. However, a person skilled in the art would be able to modify the reactions e.g. by using another chelator. Thus, this scheme shall not be understood to limit the compounds of the present invention to the DOTA chelator only.

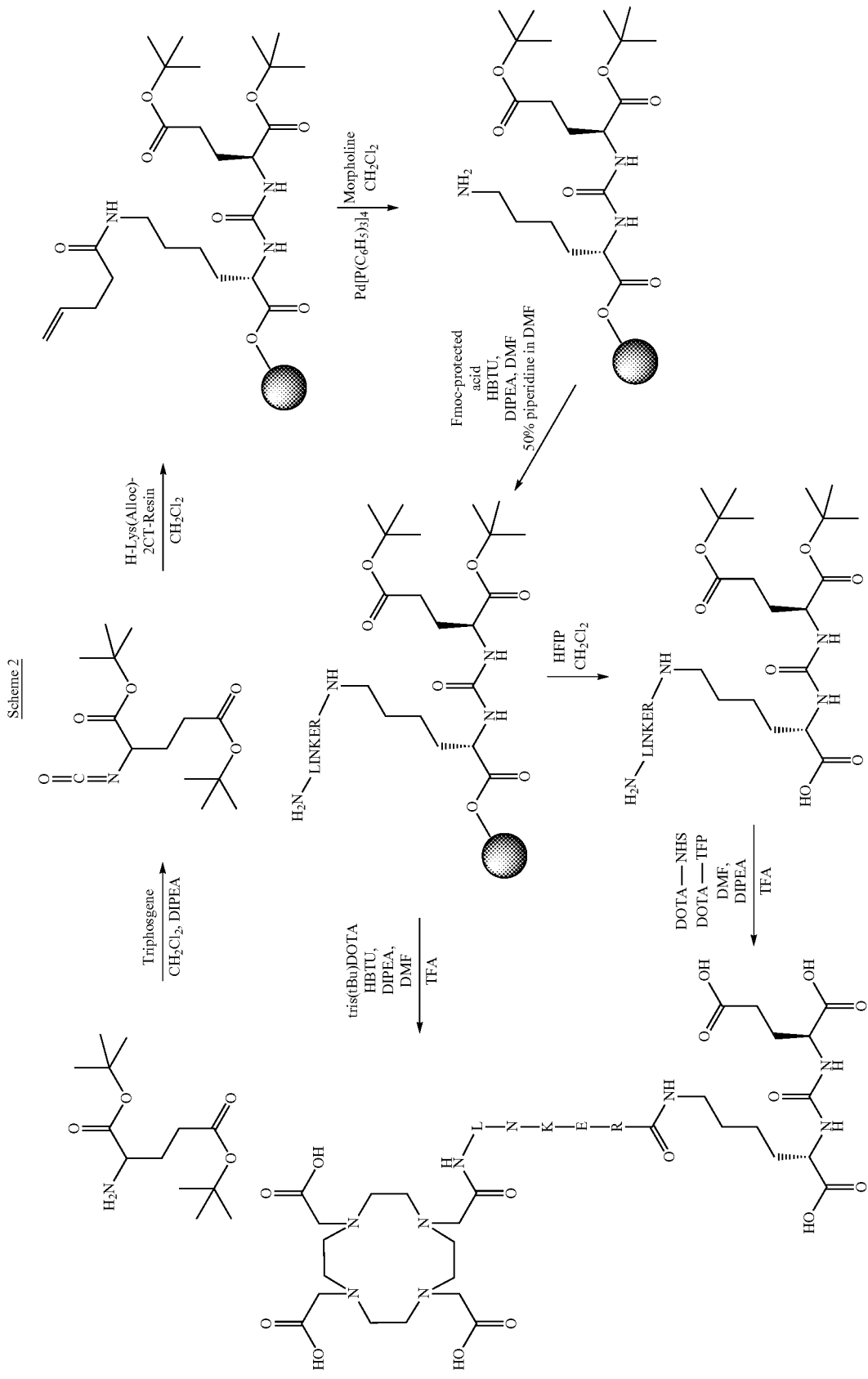

The synthesized compounds are chemically characterized by RP-HPLC, MS, and/or NMR.

The novel chelator-conjugated imaging agents with structural modifications in the linker region have improved tumor targeting properties and pharmacokinetics. The pharmacophore presents three carboxylic group able to interact with the respective side chains of PSMA and an oxygen as part of zinc complexation in the active center. Besides these obligatory interactions, the inventors were able to optimize the lipophilic interactions in the linker region.

The preclinical evaluation includes in vitro assays (affinity, internalization) and in vivo experiments (µPET screening and organ distribution).

The compounds of the present invention are better than known reference compounds with regard to kidney clearance and enrichment in the tumor. The binding affinity of PSMA inhibitors of the present invention can be influenced by linker modifications. Two cyclic moieties and at least one aromatic moiety in the linker region of the substance seem to be preferable and resulted in the high affinity compounds MB4 and MB17. In this regard, a very promising compound is MB17.

Figure 17A:
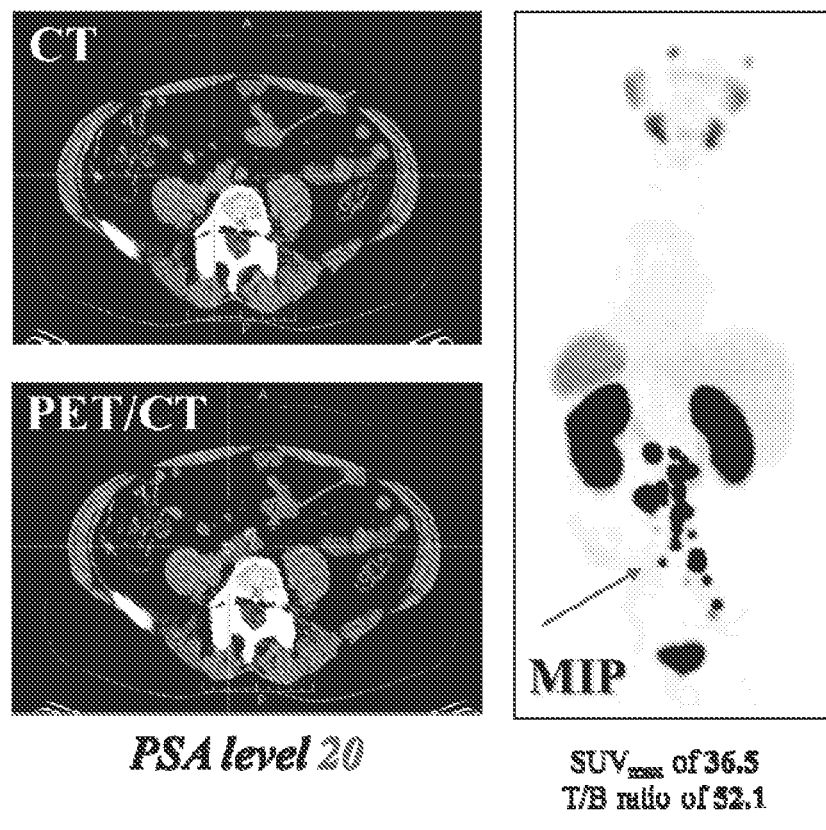
FIGS. 17A-B: Human PET/CT imaging $^{68}$Ga-labeled MB17. (a) First clinical experience with $^{68}$Ga-labeled MB17 PET/CT demonstrates the detection of small lymph node metastases 1 hour post injection, primarily due to a high radiotracer uptake. Red arrows point to a representative lesion with a SUVmax of 36.5 and a tumor-to-background ratio of 52.1 one hour post injection. MIP=maximum intensity projection of the PET 1 h post injection, (b) The significant advantage of $^{68}$Ga-labeled MB17 PET/CT is the sensitive detection of lesions even at low PSA level.
Figure 17B:
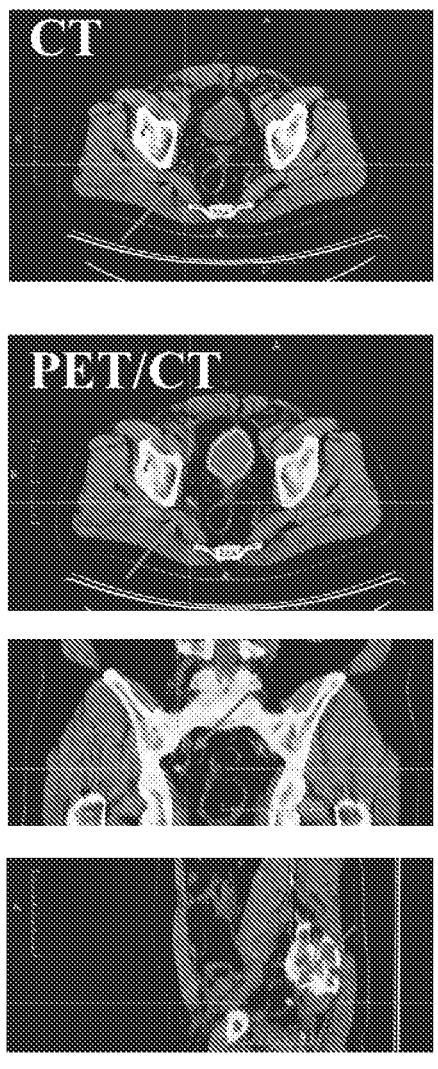
Figure 18A:
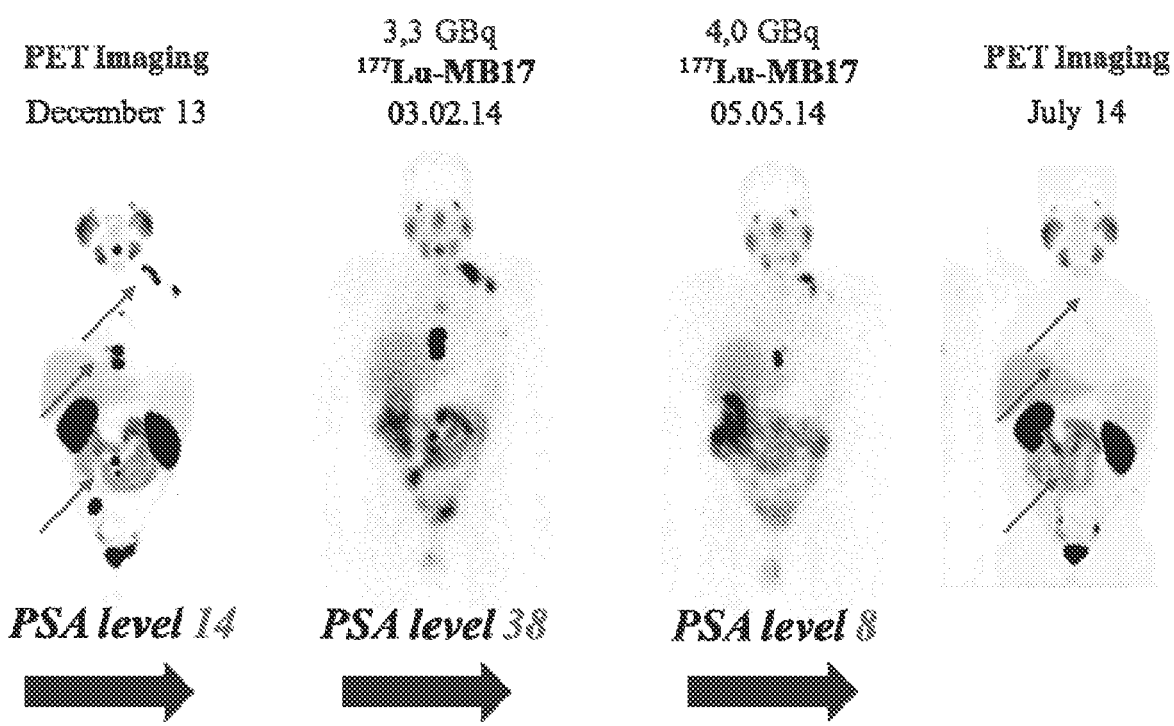
FIGS. 18A-B: PET imaging of patient with multiple prostate cancer metastasis, (a) First scan demonstrate initial PET imaging of the patient with multiple prostate cancer metastases with blood PSA value of 14. Two months later 3.3 GBq of $^{177}$Lu-labeled MB17 was applied. At this time point, the amount of PSA in blood reached a value of 38. After the first cycle, the PSA level decreased to 8. Three months after the first cycle another 4 GBq of $^{177}$Lu-labeled MB17 was applied. The control PET scan was performed one month after the second cycle. The treatment has shown a significant impact on the tumor lesions and PSA value and resulted in a reduction of bone pain, (b) The graph demonstrates the significant impact on the PSA value which decreased after the first application of the therapeutic dose of $^{177}$Lu-labeled MB17.
Figure 18B:
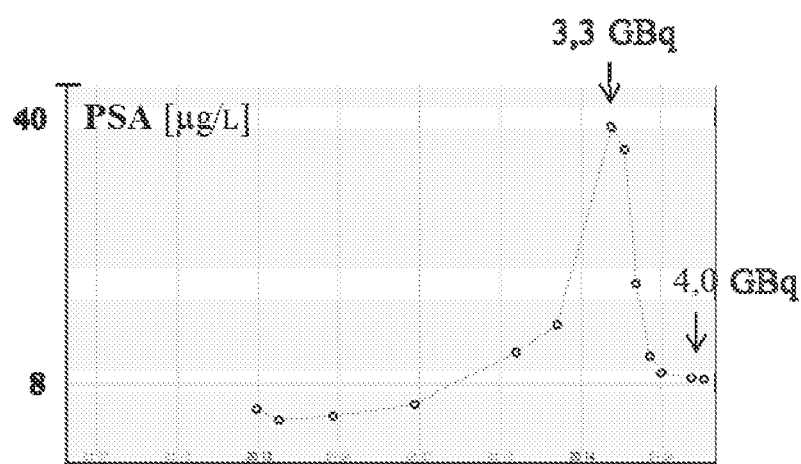

Thus, the compounds of the present invention represent novel PSMA-targeting probes with optimal characteristics which was also confirmed by organ distribution and small animal PET imaging. The compounds of the present invention show a high PSMA-specific tumor uptake. In addition, they are characterized by an early enrichment in the bladder and also the maximum kidney uptake. With regard to therapeutic use, this gives clear clinical advantages for the compounds of the present invention compared to other PSMA-inhibitors. In the PET diagrams the compounds of the present invention, in particular MB17, show a rapid background clearance as well as a substantial reduction of the enrichment in the kidney after 2 hours while it is further accumulated and retained in the PSMA-expressing tumor. Also first in vivo treatments with MB 17 showed promising data (c.f. FIGS. 17 and 18).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The below example explains the invention in more detail but are not construed to limit the invention in any way to the exemplified embodiments only.

EXAMPLES

Example 1: Synthesis of DOTA-Conjugated Inhibitors

The DOTA conjugated-PSMA inhibitors are synthesized via solid-phase peptide synthesis (c.f. Scheme 2). In a first step, the isocyanate of the glutamyl moiety was generated in situ by adding a mixture of 3 mmol of bis(tert-butyl)-L-glutamate hydrochloride and 3 mL of N-ethyldiisopropylamine (DIPEA) in 200 mL of dry $CH_2Cl_2$ to a solution of 1 mmol triphosgene in 10 mL of dry $CH_2Cl_2$ at 5° C. for 3 h. After the reaction, 0.5 mmol of a resin-immobilized (2-chloro-tritylresin) ε-allyloxycarbonyl protected lysine was added and reacted for 16 h with gentle agitation. The resin was filtered off and the allyloxy-protecting group was removed using 50 mg tetrakis-(triphenyl)palladium and 400 µL morpholine in 4 mL $CH_2Cl_2$ for 2 h.

The subsequent synthesis of the peptidomimetic PSMA binding motif was performed according to standard Fmoc protocol. The following coupling of the linker part was performed using 2 mmol of the corresponding Fmoc-protected acid, 3.96 mmol of HBTU and 2 mmol of N-ethyldiisopropylamine in a final volume of 4 mL DMF. After activation with 3.95 eq of HBTU and DIPEA for 2 h, 4 eq of tris(t-bu)-DOTA (Chematech) relative to the resin loading were reacted in a final volume of 3 mL DMF. The product was cleaved from the resin in a 2 mL mixture consisting of trifluoroacetic acid, triisopropylsilane, and water (95:2.5:2.5).

The chelator was also conjugated by using HBTU activated DOTA-NHS ester (CheMatech) or DOTA-TFP ester (Mier W., Hoffend J., Krämer S., Schuhmacher J., Hull W. E., Eisenhut M., Haberkorn U., Bioconjugate Chem. 2005, 16: 237-240).

Analysis of the synthesized molecules was performed using reversed-phase high performance liquid chromatography (RP-HPLC; Chromolith RP-18e, 100×4.6 mm; Merck, Darmstadt, Germany) with a linear A-B gradient (0% B to 100% B in 6 min) at a flow rate of 4 mL/min (analysis) or 6 mL/min (purification). Solvent A consisted of 0.1% aqueous TFA and solvent B was 0.1% TFA in $CH_3CN$. The HPLC system (L6200 A; Merck-Hitachi, Darmstadt, Germany) was equipped with a UV and a gamma detector (Bioscan; Washington, USA). UV absorbance was measured at 214 nm. Mass spectrometry was performed with a MALDI-MS Daltonics Microflex system (Bruker Daltonics, Bremen, Germany).

Example 2: Radiolabeling

Typically, 1.5 nmol of a synthesized compound of Example 1 (dissolved in 0.1 M HEPES buffer pH 7.5) was added in a volume of 100 µL to a mixture of 10 µL 2.1 M HEPES solution and 40 µL [$^{68}$Ga]Ga$^{3+}$ eluate (40 MBq). The pH of the labeling solution was adjusted to 4.5.

The radiolabeling of the compounds resulted in a radiochemical yield of >97% after 15 minutes at 95° C. and was determined by RP-HPLC and TLC. Subsequent purification was done using Sep-Pak C18 cartridges.

Example 3: Synthesis of Compounds MB4 and MB17

The isocyanate of the glutamyl moiety was generated in situ by adding a mixture of 3 mmol of bis(tert-butyl) L-glutamate hydrochloride and 1.5 mL of N-ethyldiisopropylamine (DIPEA) in 200 mL of dry $CH_2Cl_2$ to a solution of 1 mmol triphosgene in 10 mL of dry $CH_2Cl_2$ at 0° C. over 4 h. After agitation of the reaction mixture for 1 h at 25° C., 0.5 mmol of the resin-immobilized (2-chloro-tritylresin) s-allyloxycarbonyl protected lysine in 4 mL DCM was added and reacted for 16 h with gentle agitation. The resin was filtered off and the allyloxy-protecting group was removed using 30 mg tetrakis(triphenyl)palladium(0) and 400 µL morpholine in 4 mL $CH_2Cl_2$ for 3 hours. The following coupling of 3 times 4-(Fmoc-aminomethyl)benzoic acid (in case of MB4) or Fmoc-3-(2-naphthyl)-L-alanine and trans-4-(Fmoc-aminomethyl)cyclohexanecarboxylic acid (in case of MB17), respectively, was performed stepwise using 2 mmol of the Fmoc-protected acid, 1.96 mmol of HBTU and 2 mmol of N-ethyldiisopropylamine in a final volume of 4 mL DMF. After activation with 3.95 eq of HBTU and DIPEA for 2 h, 4 eq of tris(t-bu)-DOTA (Chematech) relative to the resin loading were reacted for 3 h in a final volume of 3 mL DMF. The product was cleaved from the resin in a 2 mL mixture consisting of trifluoroacetic acid, triisopropylsilane, and water (95:2.5:2.5). Purification was performed using RP-HPLC and the purified product was analysed by analytical RP-HPLC and MALDI-MS.

For preparing MB-17D which is the stereoisomer of MB17(L), the synthesis was based on Fmoc-3(2-naphthyl)-D-alanine. If not stated otherwise, in the present description MB17 means the L-stereoisomer.

Example 4: Coupling to Various Chelators

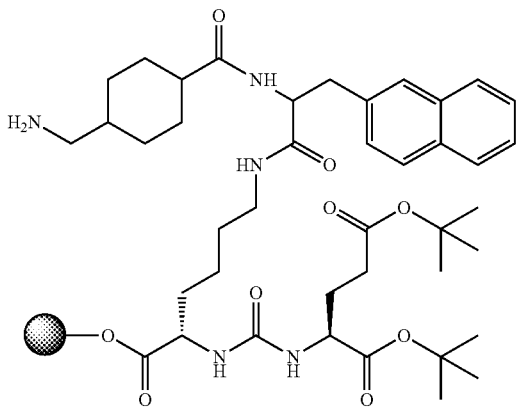 [SMILES: COC(=O)[C@H](CCCCNC(=O)C(Cc1ccc2ccccc2c1)NC(=O)C1CCC(CN)CC1)NC(=O)N[C@@H](CCC(=O)OC(C)(C)C)C(=O)OC(C)(C)C]

The chelators (DOTA, NOTA, NODAGA, DTPA, CHX-DTPA, PCTA, Do3A) were coupled to the MB17 linker by solid phase synthesis. In general, 13 µmol of resin which was coupled with the PSMA binding motif was swollen with DCM in a syringe with a filter. After washing the resin 5× with DMF, it was incubated 2× for 5 min with 20% of piperidine in DMF to deprotect the N-terminus. Another 5× washing with DMF followed.

Between 1.5 and 4 equivalents of the chelator (depending of the chelator), $0.98 \times n_{chelator}$ HATU (if needed) and 10 equivalents of DIPEA were dissolved in 500 µl of DMF, the solution was drawn up into the syringe containing the resin and incubated overnight. Next, the resin was washed 5× each with DMF, methanol, DCM and diethyl ether and dried over vacuum.

To check the state of the reaction, test separations were used. This was achieved by washing a small amount of resin with DCM into a filter tip and adding 100 µl of separation solution containing 95% TFA, 2.5% water and 2.5% TIPS. After 30 min of incubation, the solution was pipetted into ice cold diethyl ether and centrifuged. The diethyl ether was decanted and the remaining pellet was dissolved in 35 µl of ACN:H$_2$O (1:1) and analysed by HPLC (0-100% ACN in water within 5 min) and LC/MS.

If the desired product was obtained, the complete peptide was separated from the resin. The dried resin was incubated with 500 µl of the separation solution (95% TFA, 2.5% H$_2$O, 2.5% TIPS) for 2 hours. The resulting solution was mixed with ice cold diethyl ether and centrifuged (4000 min$^{-1}$, 5 min). The supernatant was discarded, new diethyl ether was added and the receptacle was shaken vigorously to resuspend the pellet. Again, the solution was centrifuged (4000 min$^{-1}$, 5 min) and the resulting supernatant discarded. The pellet was then vacuum dried and finally resuspended in 1 ml of ACN:H$_2$O (1:1).

Purification was achieved by preparative HPLC, the peaks were analysed by analytic HPLC (0-100% ACN in water within 5 min) and LC/MS and those containing the product were pooled and lyophilized.

Example 5: Radiolabelling $^{177}$Lu-Labelling $^{177}$Lu (approx. 100 MBq) was mixed with 200 µl of 0.4 M sodium acetate buffer containing Chelex (pH=5). 10 µl of a 1 mM solution of the compound in 10% DMSO in water, 2 µl of a saturated solution of ascorbic acid and 40 µl of the solution containing $^{177}$Lu were mixed and heated to 95° C. for 10 min. The labelling was checked by radio-HPLC (0-100% ACN in water within 5 min, Monolith column).

$^{68}$Ga-Labelling

For the PET scan CHX-DTPA was labelled with $^{68}$Ga. 1 ml of $^{68}$Ga was eluted from a $^{68}$Ge/$^{68}$Ga generator with 0.6 M HCl. 298 µl NaOAc buffer and 1 µl of a 10 mM solution of CHX-DTPA in DMSO was added and incubated for 5 min. Afterwards the product was purified using a SOLA cartridge. Washing was done with a 0.9% NaCl solution and for elution ethanol was used. The ethanol then was vaporized and the remaining product was dissolved in 100 µl of a 0.9% NaCl solution and 10 µl of phosphate buffer.

Example 6: Determination of the IC$_{50}$ Value

A filter plate MultiScreen$_{HTS}$-DV was incubated at room temperature with 100 µl PBS with 1% BSA per well for 30 min. After removing the PBS/BSA solution 10$^5$ LNCaP cells in 50 µl of Opti-MEM were applied to each well. Different concentrations of the compounds (leading to concentrations of 0, 0.5, 1, 2.5, 5, 10, 25, 50, 100, 500, 1000 and 5000 nM in each well) in 300 µl of Opti-MEM were mixed with 3 µl of a 150 nM solution of $^{125}$I-labeled MTP-1466 in Opti-MEM. 50 µl of the resulting solution were added to each well, each concentration was pipetted in quadruples. Each well now contained the radioactively labelled ligand in a concentration of 0.75 nM and the competitive, not labelled ligand in the concentration mentioned above. The plate was then incubated for 45 min at room temperature on a shaker.

After the incubation, the cells were washed 2× with 100 µl of ice cold PBS and 1× with 200 µl of ice cold PBS. Finally, the filters were collected and the remaining radioactivity was measured with a gamma counter. Each tube was measured for 5 min.

The data measured by the gamma counter were evaluated with Graphpad Prism to achieve an inhibition concentration 50 (IC$_{50}$) against the radioactively labelled MIP-1095.

| Conjugate | IC$_{50}$ [nM] |
|---|---|
| MB17-DOTA | 0.13 ± 0.08 |
| MB17-NOTA | 0.14 ± 0.08 |
| MB17-DTPA | 0.12 ± 0.05 |
| MB17-CHX-DTPA | 0.06 ± 0.04 |
| MB17-PCTA | 0.10 ± 0.06 |
| MB17-DO3A | 0.10 ± 0.05 |
| MB17-NODAGA | 0.09 ± 0.08 |

Example 7: µPET-Imaging Using CHX-DTPA-MB17

Figure 15:
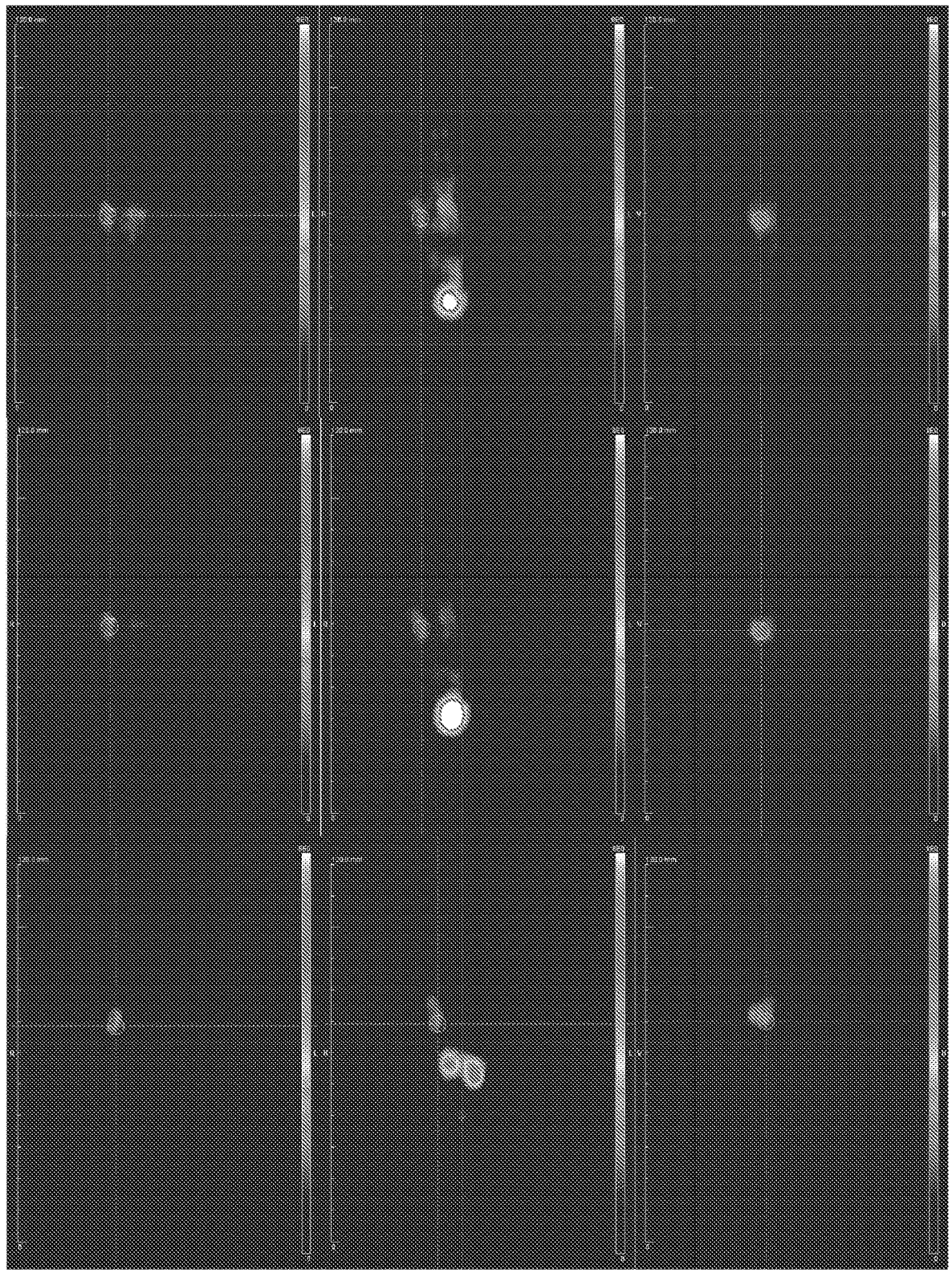
FIG. 15: PET scan of a mouse injected with $^{68}$Ga-CHX-DTPA. On the left the caudal, in the centre the dorsal and on the right the lateral view. The pictures cover the time spans of 20-40 min (top), 40-60 min (centre) and 120-140 min (bottom).
Figure 16:
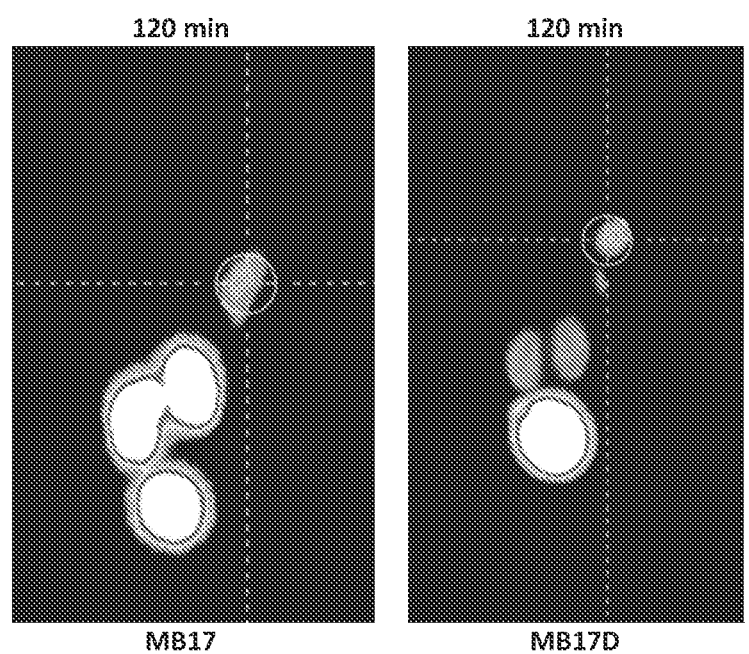
FIG. 16: MB-17 vs MB-17.D. Whole-body coronal microPET images of athymic male nude mice bearing LNCaP tumor xenografts. The tumor-targeting efficacy and pharmacokinetic properties of the stereoisomers MB-17 and MB-17 D were directly compared at 2 hours post injection.

Before injection into the mouse, the solution containing the purified $^{68}$Ga-CHX-DTPA-coupled PSMA inhibitor was sterile-filtered. 100 µl of this solution was taken up into a syringe and then injected into a BALB/c nude mouse LNCaP xenograft, intravenously into the tail vein. The PET scan was recorded for 140 min with a Siemens Inveon PET (FIG. 15)

Example 8: Determination of the Competitive Binding Affinity

In order to compare the series of novel compounds the competitive binding affinity and the specific internalization was analyzed using the PSMA expressing cell line LNCaP. To determine specific cellular uptake, cells were blocked with 2-(phosphonomethyl)-pentanedioic acid (PMPA). The inhibition potency was also investigated by the enzyme-based NAALADase assay.

Cell Culture

For binding studies and in vivo experiments LNCaP cells (metastatic lesion of human prostatic adenocarcinoma, ATCC CRL-1740) were cultured in RPMI medium supplemented with 10% fetal calf serum and Glutamax (PAA, Austria). During cell culture, cells were grown at 37° C. in an incubator with humidified air, equilibrated with 5% CO2. The cells were harvested using trypsin-ethylenediaminetetraacetic acid (trypsin-EDTA; 0.25% trypsin, 0.02% EDTA, all from PAA, Austria) and washed with PBS.

Cell Binding and Internalization

The competitive cell binding assay and internalization experiments were performed as described previously (Eder et al. 2012). Briefly, the respective cells ($10^5$ per well) were incubated with the radioligand (68Ga-labeled [Glu-urea-Lys (Ahx)]2-HBED-CC (Schafer et al., 2012) in the presence of 12 different concentrations of analyte (0-5000 nM, 100 µL/well). After incubation, washing was carried out using a multiscreen vacuum manifold (Millipore, Billerica, Mass.). Cell-bound radioactivity was measured using a gamma counter (Packard Cobra II, GMI, Minnesota, USA). The 50% inhibitory concentration (IC50) was calculated by fitting the data using a nonlinear regression algorithm (GraphPad Software). Experiments were performed three times.

To determine the specific cell uptake and internalization, $10^5$ cells were seeded in poly-L-lysine coated 24-well cell culture plates 24 h before incubation. After washing, the cells were incubated with 25 nM of the radiolabeled compounds for 45 min at 37° C. and at 4° C., respectively. Specific cellular uptake was determined by competitive blocking with 2-(phosphonomethyl)pentanedioic acid (500 µM final concentration, PMPA, Axxora, Loerrach, Germany). Cellular uptake was terminated by washing 4 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to $10^6$ cells [% ID/$10^6$ cells], Naaladase Assay Recombinant human PSMA (rhPSMA, R&D systems, Wiesbaden, Germany) was diluted in assay buffer (50 mM HEPES, 0.1 M NaCl, pH 7.5) to 0.4 µg/mL. The substrate Ac-Asp-Glu (Sigma, Taufkirchen, Germany, 40 µM final concentration) was mixed with natGa labeled analyte at concentrations ranging from 0.05 nM to 1000 nM in a final volume of 125 µL assay buffer. The mixtures were combined with 125 µL of the rhPSMA solution (0.4 µg/mL) and incubated for one hour at 37° C. The reaction was stopped by heating at 95° C. for 5 minutes. 250 µL of a 15 mM solution of ortho-phthaldialdehyde (Sigma, Taufkirchen, Germany) was added to all vials and incubated for 10 minutes at ambient temperature. Finally, 200 µL of the reaction solutions were loaded onto a F16 Black Maxisorp Plate (Nunc, Langenselbold, Germany) and read at excitation and emission wavelengths of 330 nm and 450 nm, respectively, using a microplate reader (DTX-880, Beckman Coulter, Krefeld, Germany). The data were analyzed by a one site-total binding regression algorithm of GraphPad (GraphPad Software, California, USA).

Biodistribution 7- to 8-week-old male BALB/c nu/nu mice (Charles River Laboratories) were subcutaneously inoculated into the right trunk with $5 \times 10^6$ cells of LNCaP (in 50% Matrigel; Becton Dickinson, Heidelberg, Germany). The tumors were allowed to grow until approximately 1 cm3 in size. The radiolabeled compounds were injected into the tail vein (approx. 1 MBq per mouse; 0.06 nmol). At 1 h after injection the animals were sacrificed. Organs of interest were dissected, blotted dry, and weighed. The radioactivity was measured using a gamma counter and calculated as % ID/g.

MicroPET

For the microPET studies, 10-25 MBq of the radiolabeled compounds in a volume of 0.15 ml (~0.5 nmol) were injected via a lateral tail vein into mice bearing LNCaP tumor xenografts. The anesthetized animals (2% sevoflurane, Abbott, Wiesbaden, Germany) were placed in prone position into the Inveon small animal PET scanner (Siemens, Knoxville, Tenn., EISA) to perform dynamic micro-PET scans and 20 min-static scans; c.f. FIG. 1, 3, 5-14

TABLE A

| Substance | IC$_{50}$ [nM] | Internalization [% IA/$10^6$ cells] |
|---|---|---|
| MB2 | 2.75 ± 0.82 | 8.78 ± 3.96 for Ga-68 |
|  |  | 5.22 ± 0.67 for Lu-177 |
| MB3 | 10.51 ± 6.06 | 3.65 ± 1.32 for Lu-177 |
| MB4 | 0.74 ± 0.50 | 14.18 ± 0.98 for Ga-68 |
|  |  | 14.25 ± 4.61 for Lu-177 |
| MB10 | 8.67 ± 1.58 | 6.96 ± 3.90 for Lu-177 |
| MB17 | 0.13 ± 0.08 | 17.02 ± 4.36 for Ga-68 |
|  |  | 17.51 ± 3.99 for Lu-177 |
| MB17.D | 12.41 ± 5.10 | 2.60 ± 0.14 for Lu-177 |
| MB22 | 52.80 | 1.15 ± 0.19 for Lu-177 |
| MB24 | 3.33 | 7.26 ± 2.76 for Lu-177 |
| MB25 | 6.64 | 3.91 ± 0.54 forLu-177 |
| MB31 | 91.80 | 0.53 ± 0.48 for Lu-177 |
| MB33 | 59.33 | 1.96 ± 0.20 for Lu-177 |
| MB35 | 26.18 | 0.97 ± 0.17 for Lu-177 |

Figure 2:
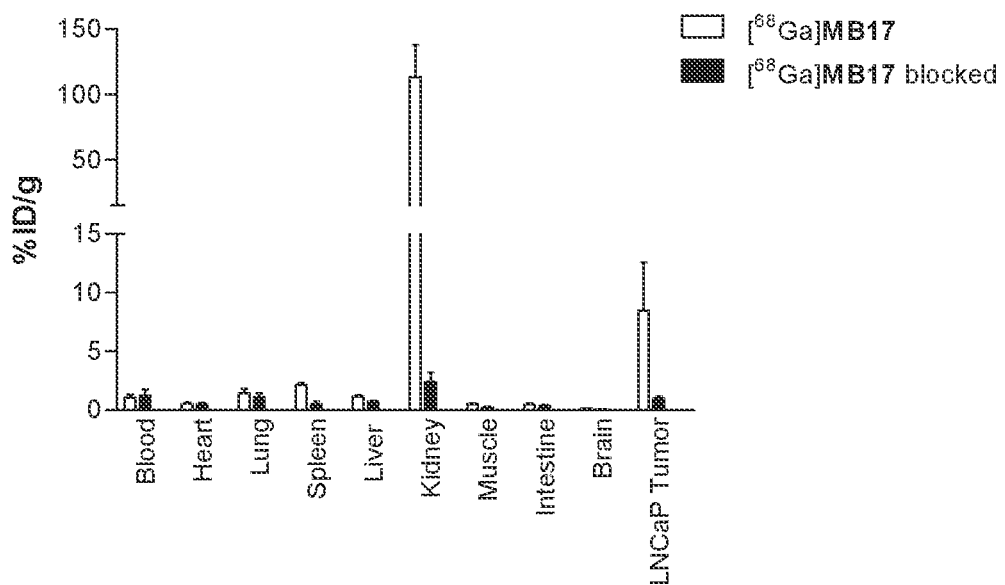
FIG. 2: Organ Distribution at 1 h post injection. Organ distribution at one hour post injection of 0.06 nmol of the $^{68}$Ga labeled PSMA inhibitor MB17. PSMA-blocking by co-administration of 2 mg/kg body weight 2-PMPA indicates PSMA-specific uptake in the tumor and the kidneys. Data are expressed as mean % ID/g tissue±SD (n=3).
Figure 3:
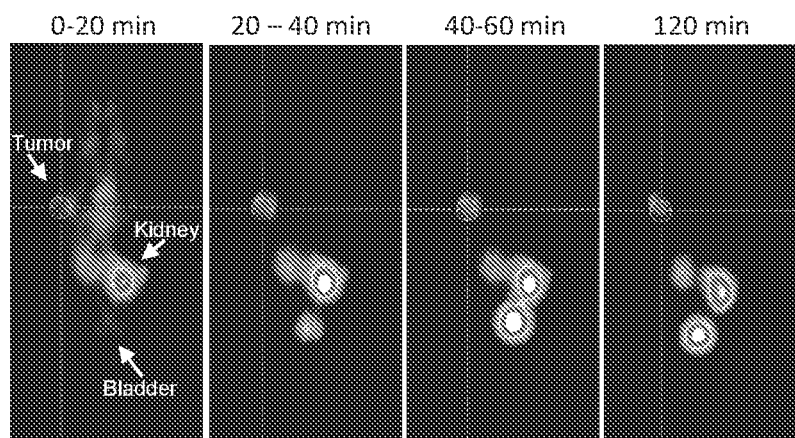
FIG. 3: PET—Imaging of MB4. Whole-body coronal microPET images of an athymic male nude mice bearing LNCaP tumor xenografts. The tumor-targeting efficacy and pharmacokinetic properties of [$^{68}$Ga]MB4 were evaluated by dynamic microPET scans. Approximately 15 MBq/mouse were injected. Graph A shows the respective time-activity-curves of kidney and bladder and graph B the respective time-activity-curves of heart, muscle and tumor. The values are expressed as mean SUV (standardized uptake values)
Figure 3:
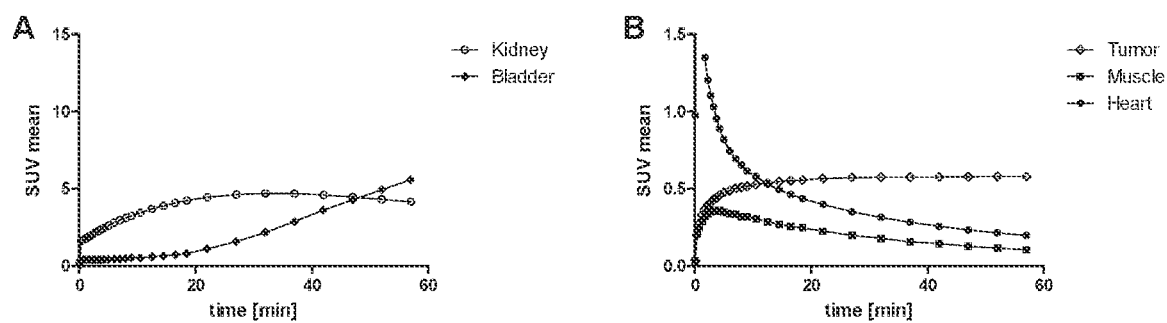

The present example shows that the binding affinity of PSMA inhibitors can be influenced by linker modifications. Two cyclic moieties and at least one aromatic moiety in the linker region of the substance seem to be preferable and resulted in the high affinity compounds MB4 and MB17. These novel variants show low nanomolar affinity to LNCap cell line and were specifically internalized at 37° C. up to 48% ID/$10^6$ cells. Former studies showed that besides binding affinity the internalization properties of PSMA-targeting probes are highly important and high internalization rates are essential for high in vivo tumor uptake and retention. Thus, MB17 represents a novel PSMA-targeting probe with optimal characteristics which was also confirmed by organ distribution and small animal PET imaging. MB17 shows a high PSMA-specific tumor uptake (FIG. 2). In addition, dynamic PET imaging of MB17 (FIG. 2) shows an early enrichment in the bladder and also the maximum kidney uptake (highest point in the time-activity-curve) is as early as 15 min after injection of the radiotracer and diminishes substantially already after 20 minutes. With regard to therapeutic use, this gives clear clinical advantages for MB17 compared to other PSMA-inhibitors. In the PET diagrams (FIG. 1) MB17 shows a rapid background clearance as well as a substantial reduction of the enrichment in the kidney after 2 hours while it is further accumulated and retained in the PSMA-expressing tumor.

Figure 4:
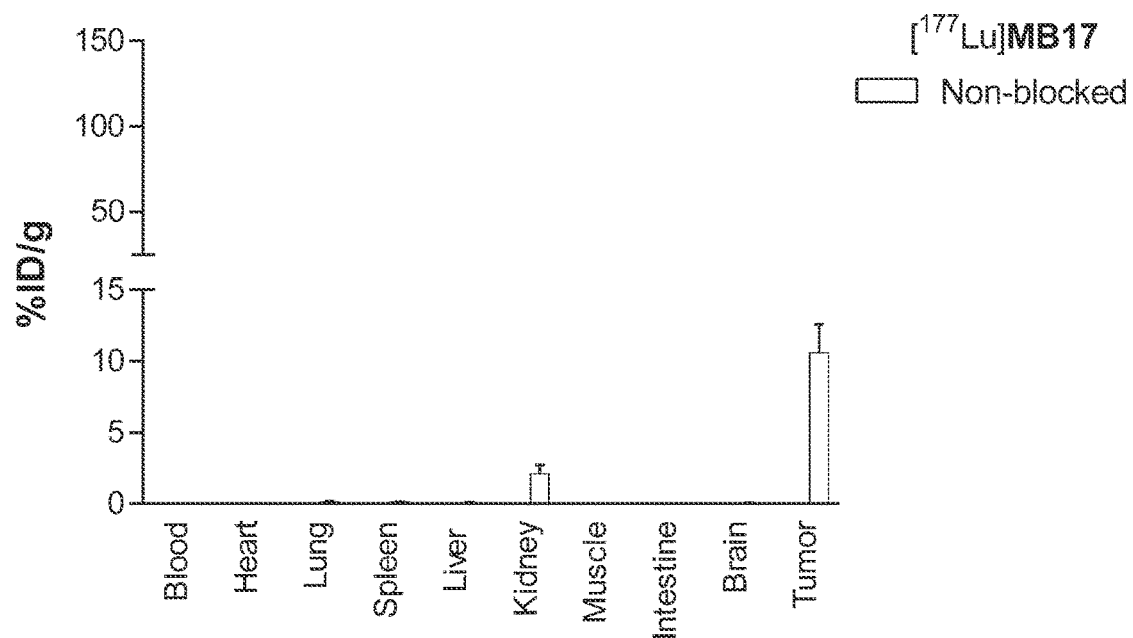
FIG. 4: Organ distribution expressed as % ID/g tissue±SD (n=5) 24 h post injection of 0.06 nmol of the $^{177}$Lu-labeled MB17. Organ distribution with $^{177}$Lu shows that the high initial kidney uptake is nearly completely washed out (2.13±1.36% ID/g) after 24 hours while the tumor uptake remained high and even increased (10.58±4.50% ID/g). Other organs as liver (0.08±0.03% ID/g), lung (0.11±0.13% ID/g) and spleen (0.13±0.05% ID/g) showed very low uptake. The favourable pharmacokinetics led to extremely high tumor-to-background ratios (Tumor/Blood: 1058; Tumor/Muscle: 529) after 24 hours
Figure 5:
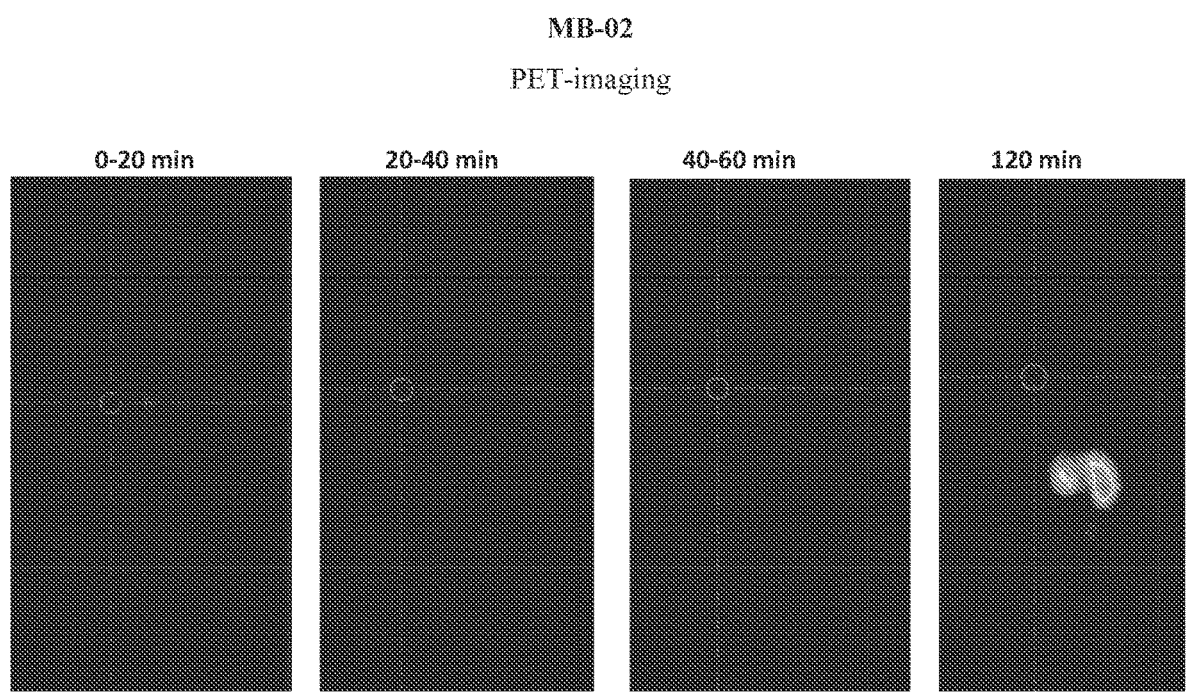
FIG. 5: PET—Imaging of MB 2. Whole-body coronal microPET images of an athymic male nude mouse bearing LNCaP tumor xenografts. The tumor-targeting efficacy and pharmacokinetic properties of [$^{68}$Ga]MB2 were evaluated by dynamic microPET scans. Approximately 15 MBq/mouse were injected.
Figure 6:
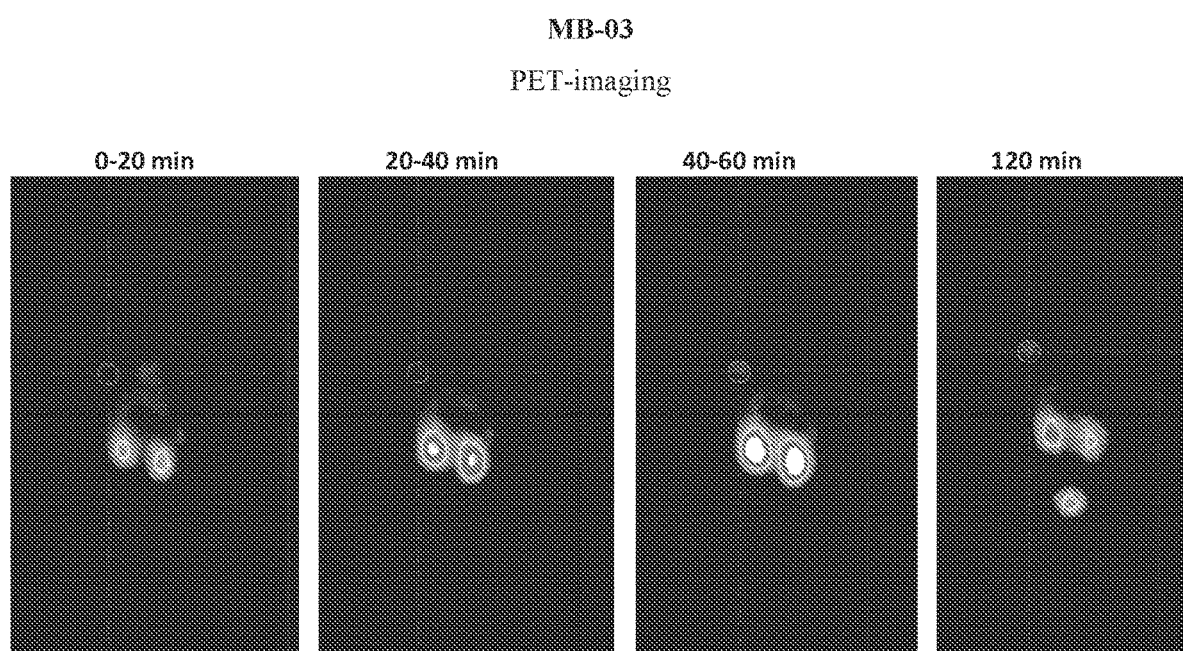
FIG. 6: PET—Imaging of MB 3. Whole-body coronal microPET images of an athymic male nude mouse bearing LNCaP tumor xenografts. The tumor-targeting efficacy and pharmacokinetic properties of [$^{68}$Ga]MB 3 were evaluated by dynamic microPET scans. Approximately 15 MBq/mouse were injected.
Figure 7:
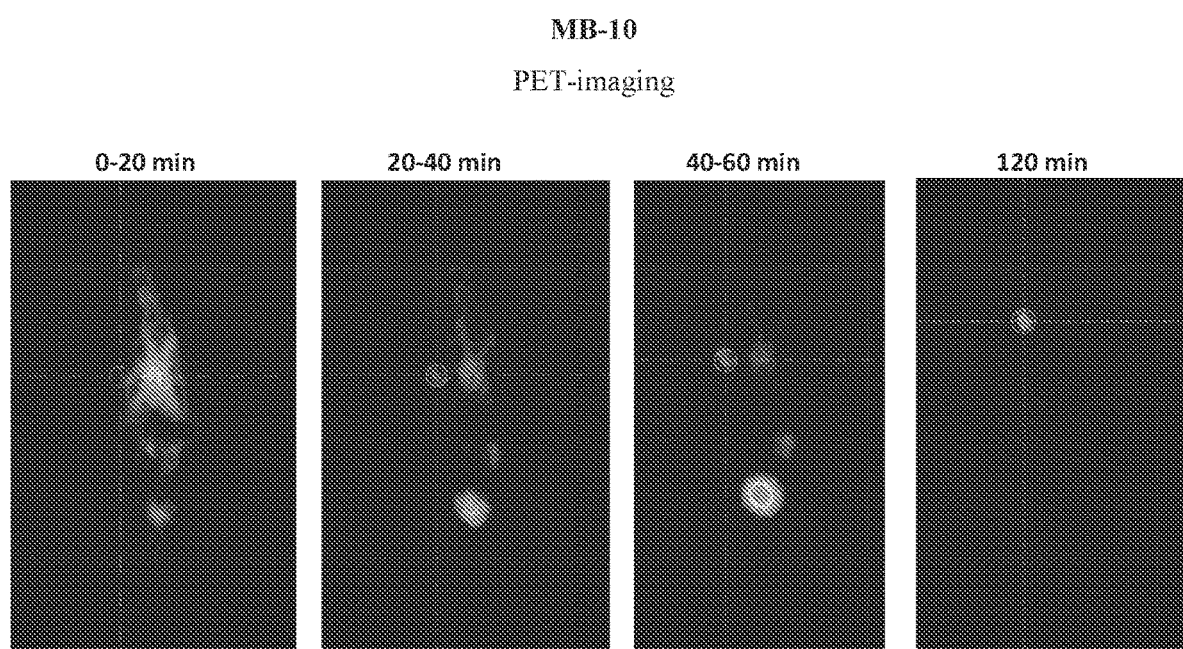
FIG. 7: PET—Imaging of MB10. Whole-body coronal microPET images of an athymic male nude mouse bearing LNCaP tumor xenografts. The tumor-targeting efficacy and pharmacokinetic properties of [$^{68}$Ga]MB10 were evaluated by dynamic microPET scans. Approximately 15 MBq/mouse were injected.
Figure 8:
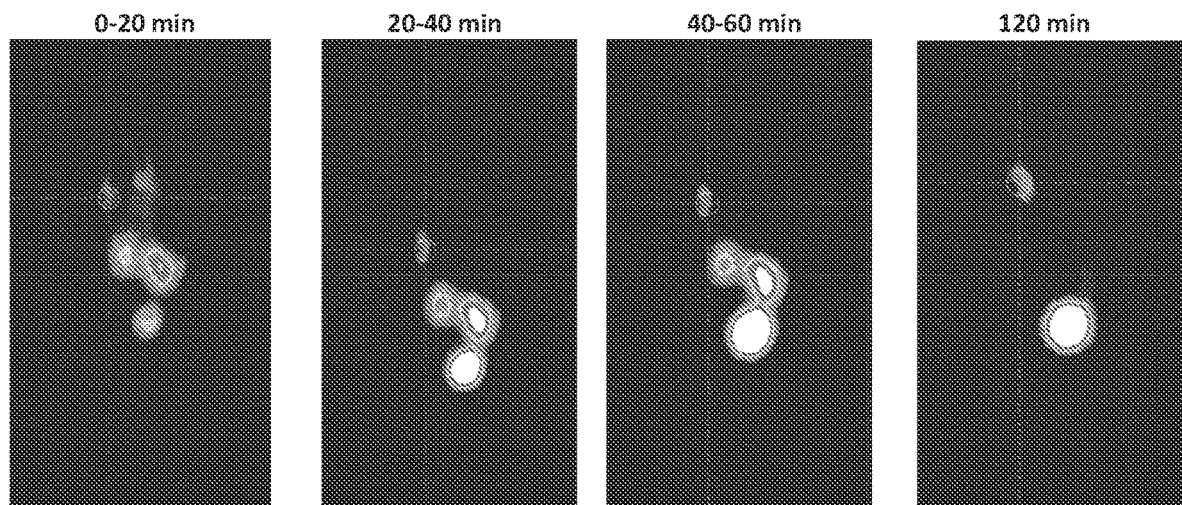
FIG. 8: PET—Imaging of MB17.D. Whole-body coronal microPET images of an athymic male nude mouse bearing LNCaP tumor xenografts. The tumor-targeting efficacy and pharmacokinetic properties of [$^{68}$Ga]MB17.D were evaluated by dynamic microPET scans. Approximately 15 MBq/mouse were injected. MB17D: stereoisomer of MB17(L); synthesis based on Fmoc-3(2-naphthyl)-D-alanine
Figure 9:
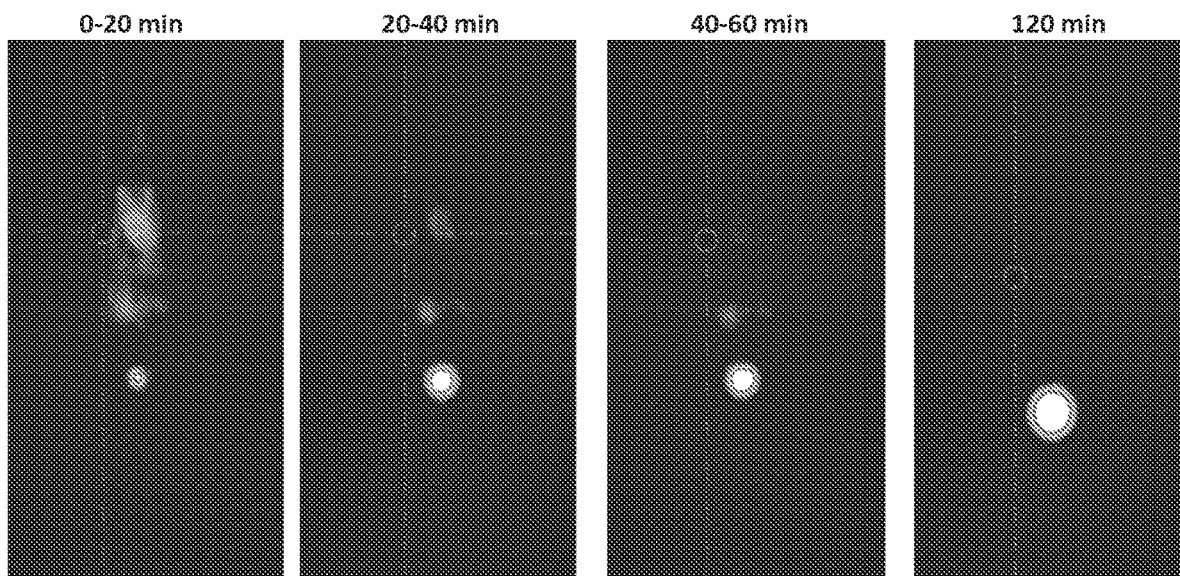
FIG. 9: PET—Imaging of MB22. Whole-body coronal microPET images of an athymic male nude mouse bearing LNCaP tumor xenografts. The tumor-targeting efficacy and pharmacokinetic properties of [$^{68}$Ga]MB22 were evaluated by dynamic microPET scans. Approximately 15 MBq/mouse were injected.
Figure 10:
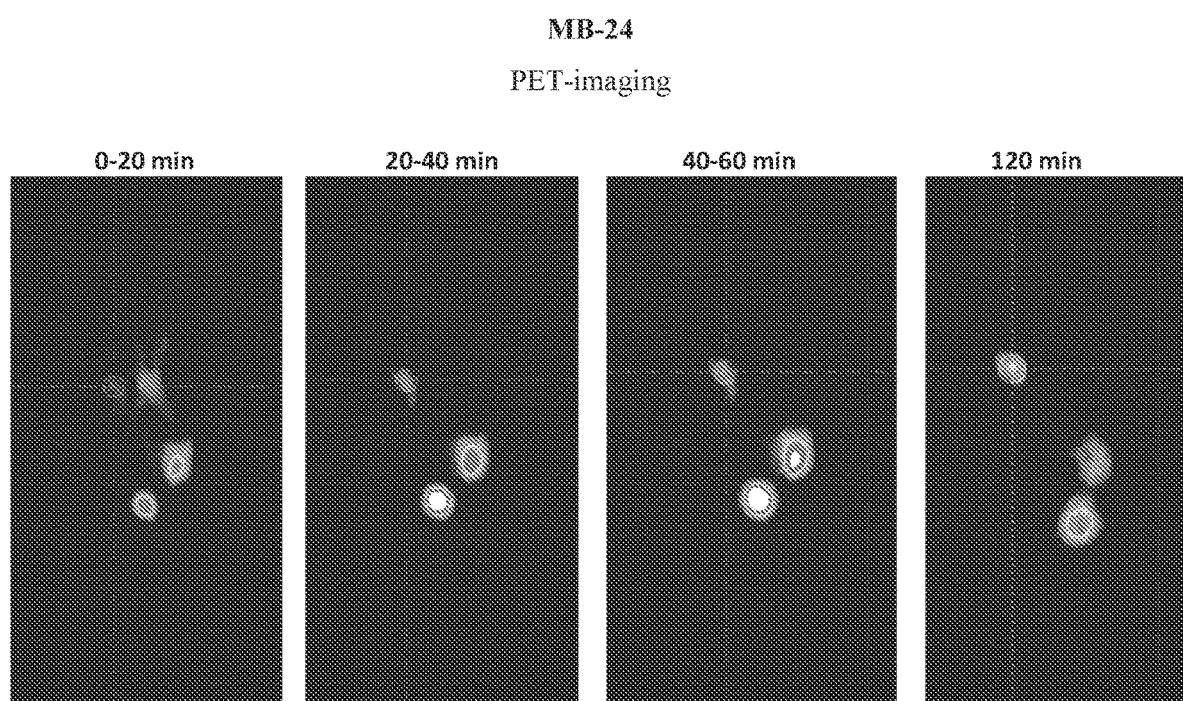
FIG. 10: PET—Imaging of MB 24. Whole-body coronal microPET images of an athymic male nude mouse bearing LNCaP tumor xenografts. The tumor-targeting efficacy and pharmacokinetic properties of [$^{68}$Ga]MB 24 were evaluated by dynamic microPET scans. Approximately 15 MBq/mouse were injected.
Figure 11:
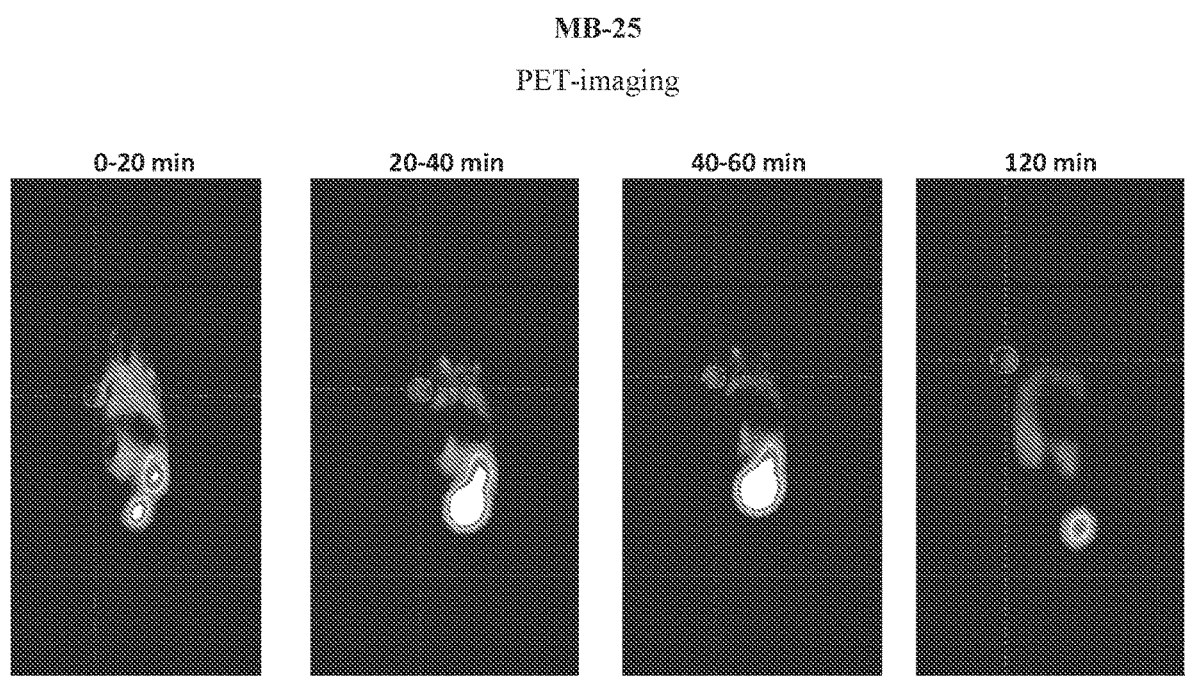
FIG. 11: PET—Imaging of MB25. Whole-body coronal microPET images of an athymic male nude mouse bearing LNCaP tumor xenografts. The tumor-targeting efficacy and pharmacokinetic properties of [$^{68}$Ga]MB25 were evaluated by dynamic microPET scans. Approximately 15 MBq/mouse were injected.
Figure 12:
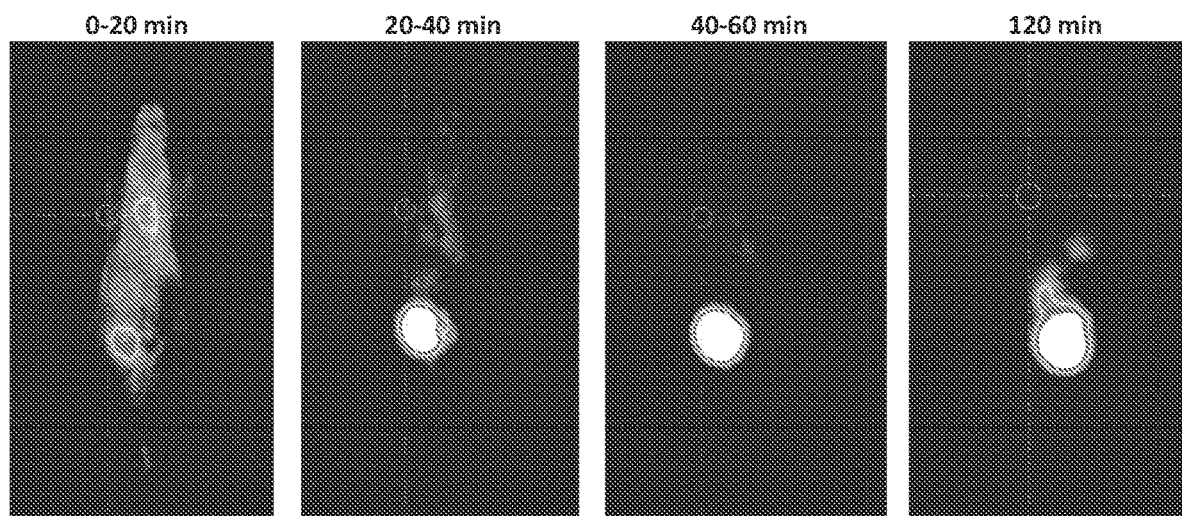
FIG. 12: PET—Imaging of MB31. Whole-body coronal microPET images of an athymic male nude mouse bearing LNCaP tumor xenografts. The tumor-targeting efficacy and pharmacokinetic properties of [$^{68}$Ga]MB31 were evaluated by dynamic microPET scans. Approximately 15 MBq/mouse were injected.
Figure 13:
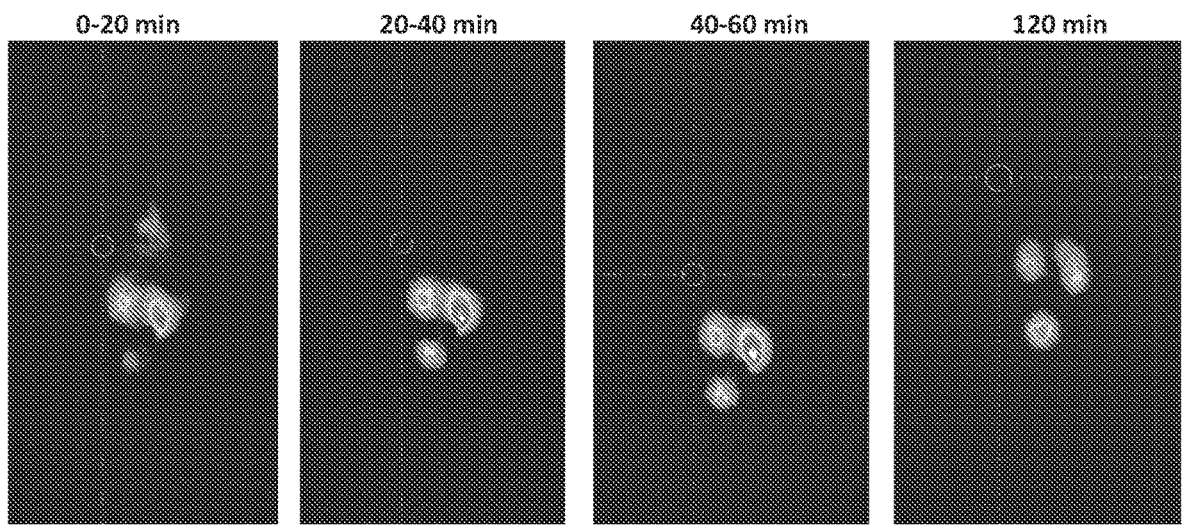
FIG. 13: PET—Imaging of MB33. Whole-body coronal microPET images of an athymic male nude mouse bearing LNCaP tumor xenografts. The tumor-targeting efficacy and pharmacokinetic properties of [$^{68}$Ga]MB33 were evaluated by dynamic microPET scans. Approximately 15 MBq/mouse were injected.
Figure 14:
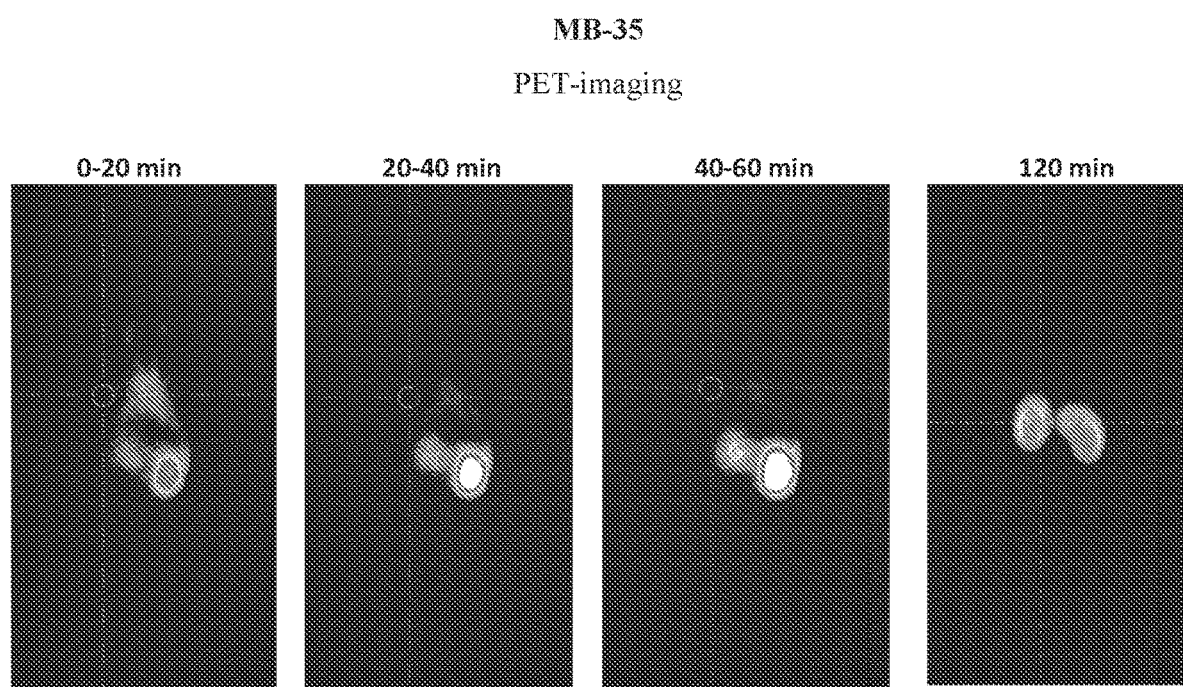
FIG. 14: PET—Imaging of MB35. Whole-body coronal microPET images of an athymic male nude mouse bearing LNCaP tumor xenografts. The tumor-targeting efficacy and pharmacokinetic properties of [$^{68}$Ga]MB35 were evaluated by dynamic microPET scans. Approximately 15 MBq/mouse were injected.

In addition, organ distribution with $^{177}$Lu (FIG. 4) showed that the high initial kidney uptake is nearly completely washed out (2.13±1.36% ID/g) after 24 hours while the tumor uptake remained high and even increased (10.58±4.50% ID/g). Other organs as liver (0.08±0.03% ID/g), lung (0.11±0.13% ID/g) and spleen (0.13±0.05% ID/g) showed very low uptake. The favourable pharmacokinetics led to extremely high tumor-to-background ratios (Tumor/Blood: 1058; Tumor/Muscle: 529) after 24 hours Table A clearly confirms that the chemical modifications in the linker region of the molecule affect the biological properties, e.g. affinity and internalization efficacy. MB17 and MB4 show the most promising binding properties on cells.

Example 9: Clinical Data Concerning MB17

PET/CT imaging was performed using the radiotracer MB17 labeled with Ga-68 (c.f FIG. 17)

The $^{68}$Ge/$^{68}$Ga-generator used for radiopharmaceutical production was purchased from IDB-Holland BV (Baarle-Nassau, The Netherlands). Disposable cassette kits and chemicals including the precursor in GMP-compliant grade used for the radiosynthesis were obtained from ABX advanced biochemical compounds (Radeberg, Germany). An Ultimate 3000 HPLC system (Dionex) (acetonitrile (A), water+0.1% TFA (B); gradient: 0.5 min 95% B, 10.0 min 80% A, flowrate: 2 mL/min) equipped with a Chromolith Performance RP-18e column (100×4.6 mm, Merck) and a NaI radiodetector (Raytest) was used to determine the radiochemical purity. Residual solvents were determined using a 6850 Series gas chromatograph (Agilent Technologies). Endotoxin testing was performed with an Endosafe®-PTS device (Charles River).

2 µg of MB17 were dissolved in 1.5 M acetate buffer pH 4.5 (1 mL) and 1 M ascorbic acid (10 µL) and transferred into the reaction vessel. The $^{68}$Ge/$^{68}$Ga-generator was eluted with 10 mL of 0.6 M HCl and the eluate diluted with 9 mL of ultrapure water. The mixture was then transferred to a cation exchange cartridge (Macherey-Nagel PS-H+, Size M) and eluted with 5 M NaCl solution (1.2 mL) into the preheated reaction vessel (100° C.). The reaction mixture was heated for 10 minutes. The crude reaction mixture was then removed from the reaction vessel and transferred to a pre-conditioned (10 mL EtOH/10 mL ultrapure water) C18 cartridge (Waters Sep-Pak light). 9 mL ultrapure water was used to rinse the reaction vessel and passed over the C18 cartridge. The C18 cartridge was washed with another 5 mL of ultrapure water. The final product was eluted from the C18 cartridge with 2 mL of EtOH/H$_2$O (v:v 1:1), sterile filtered (Millipore Cathivex-GV, 0.22 µm) and diluted with 10 mL of phosphate buffered saline (PBS) solution pH 7.4 (according to Eur. Ph. 8.0 (4005000)). The $^{68}$Ga-MB17 complex solution was applied to patients via an intravenous bolus.

Example 10: Human Therapy with $^{177}$Lu-Labeled MB17

For therapy, the PSMA ligand MB17 was radiolabeled with Lu-177. $^{177}$LuCl$_3$ was obtained from Perkin Elmer (4 GBq, NEZ307D, 0.04 M HCl). 80 nmoles of MB17 were dissolved in 400 µL sodium acetate buffer (0.4 M, pH 5) supplemented with 5 µL of 20% ascorbic acid. The solution was transferred to the $^{177}$LuCl$_3$ and incubated for 10 minutes at 95° C. Finally, 2 mL 0.9% NaCl was added. For quality control, ITLC and radio-HPLC was performed.

The $^{177}$Lu-labeled MB17 was applied to patients via an intravenous bolus (5 mL, slowly within 30 seconds). The intravenous application was accompanied by an infusion of 0.9% NaCl for 4.5 h starting at 0.5 h before injection. Reference is made to FIG. 18.

The invention is further described by the following numbered paragraphs:

1. A compound of Formula (Ia) or (Ib):

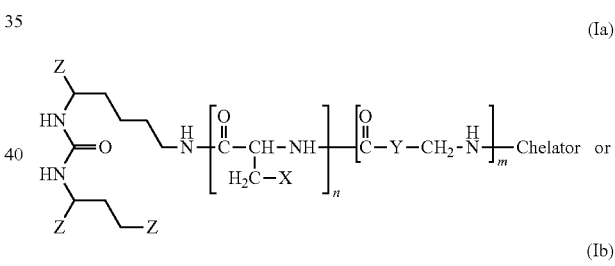

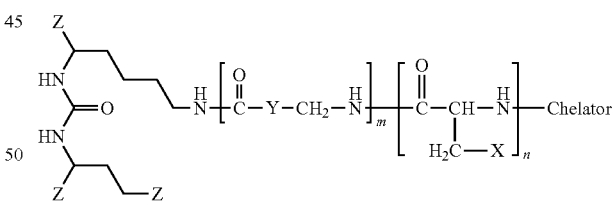

with:

| | |
|---|---|
| n: | 0, 1 |
| m: | 1, 2, 3, 4 |
| Z: | —CO$_2$H, —SO$_2$H, —SO$_3$H, —SO$_4$H, —PO$_2$H, —PO$_3$H, —PO$_4$H$_2$ |
| X: | Naphthyl, Phenyl, Biphenyl, Indolyl (=2,3-benzopyrrolyl), Benzothiazolyl |
| Y: | Aryl, Alkylaryl, Cyclopentyl, Cyclohexyl, Cycloheptyl |
| Chelator radical of: | 1,4,7,10-tetraazacyclododecane-N,N',N'',N'''-tetraacetic acid (DOTA), N,N''-bis[2-hydroxy-5-(carboxyethyl)benzyl]ethylenediamine-N,N''-diacetic acid (HBED-CC), 1,4,7-triazacyclononane-1,4,7-triacetic acid (NOTA), 2-(4,7-bis(carboxymethyl)-1,4,7-triazonan-1-yl)pentanedioic acid (NODAGA), |

| |
|---|
| 2-(4,7,10-tris(carboxymethyl)-1,4,7,10-tetraazacyclododecan-1-yl)pentanedioic acid (DOTAGA), |
| 1,4,7-triazacyclononane phosphinic acid (TRAP), |
| 1,4,7-triazacyclononane-1-[methyl(2-carboxyethyl)phosphinic acid]-4,7-bis[methyl(2-hydroxymethyl)phosphinic acid] (NOPO), |
| 3,6,9,15-tetraazabicyclo[9.3.1]pentadeca-1(15),11,13-triene-3,6,9-triacetic acid (PCTA), |
| N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), |
| Diethylenetriaminepentaacetic acid (DTPA) |
| Trans-cyclohexyl-diethylenetriaminepentaacetic acid (CHX-DTPA) |
| 1-oxa-4,7,10-triazacyclododecane-4,7,10-triacetic acid (oxo-Do3A) |
| p-isothiocyanatobenzyl-DTPA (SCN-Bz-DTPA) |
| 1-(p-isothiocyanatobenzyl)-3-methyl-DTPA (1B3M) |
| 2-(p-isothiocyanatobenzyl)-4-methyl-DTPA (1M3B) |
| 1-(2)-methyl-4-isocyanatobenzyl-DTPA (MX-DTPA). |

2. The compound of paragraph 1 having the structure R'-LINKER-R, wherein R' radical of =DOTA and R=radical of Glu-Urea-Lys:

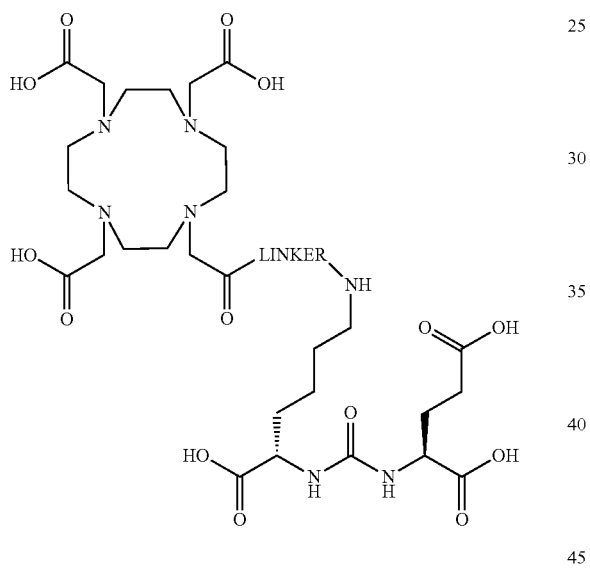

wherein the compound R'-LINKER-R is selected from:

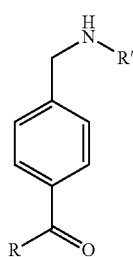

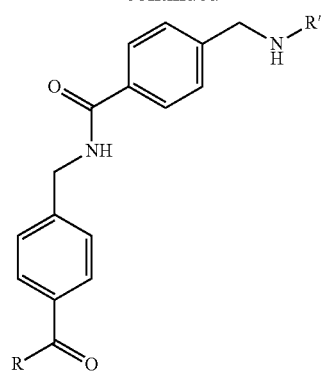

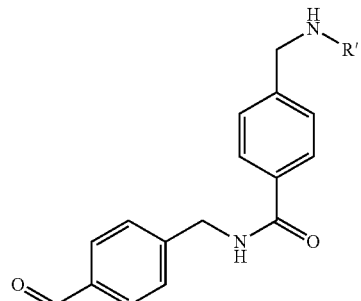

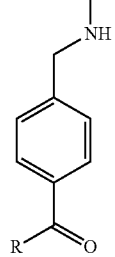

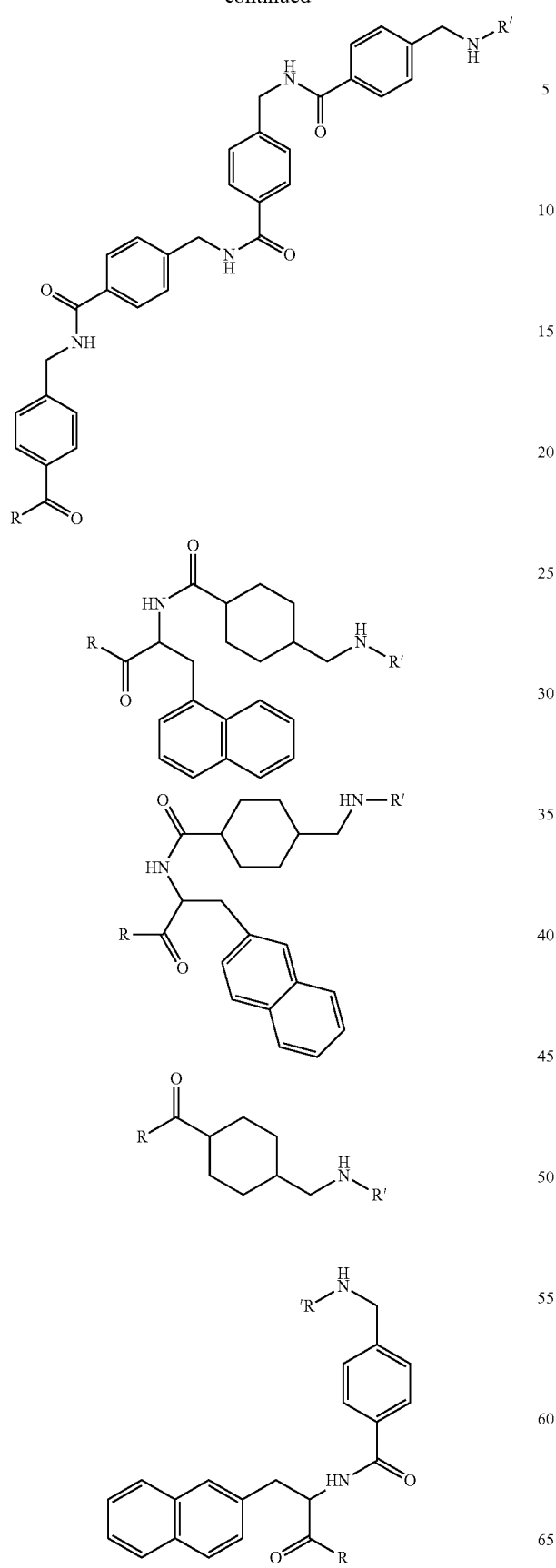
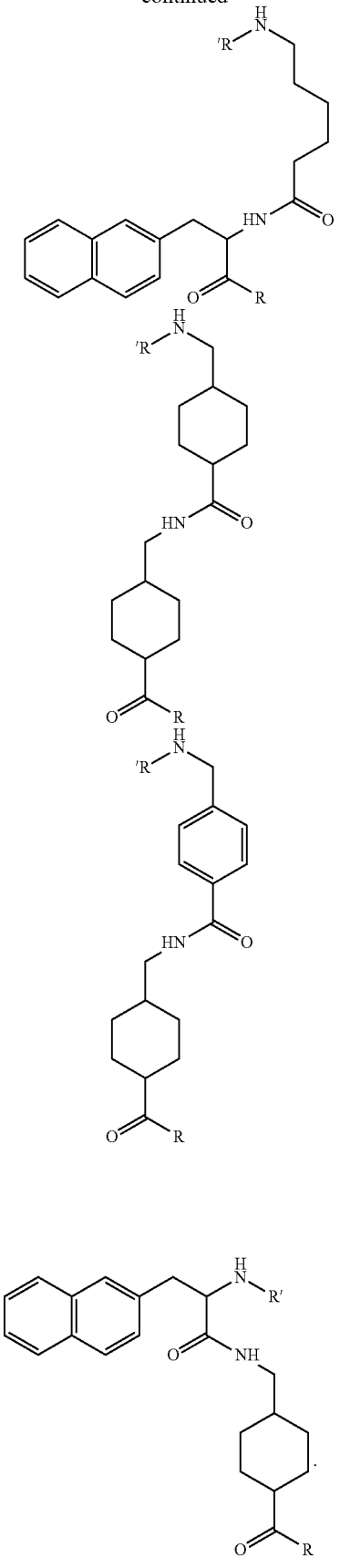

3. The compound of paragraph 1 or 2, selected from the following:
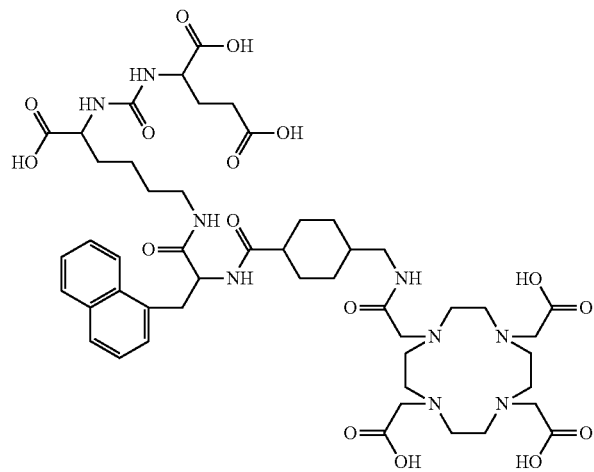
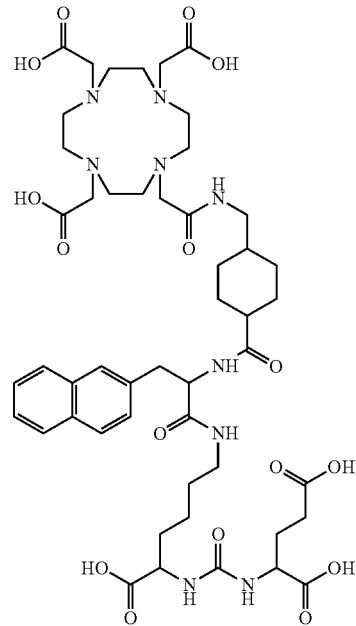
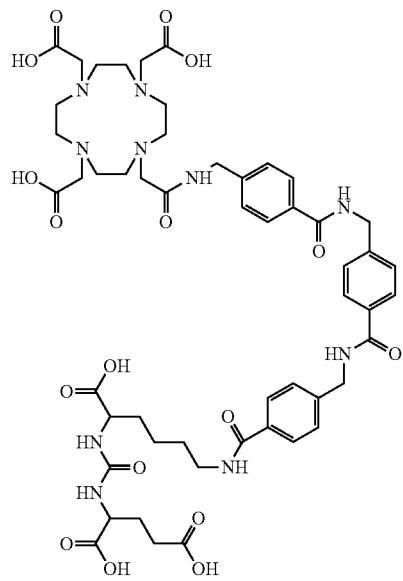
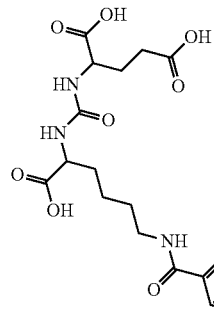
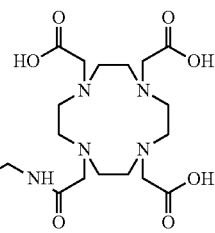

-continued
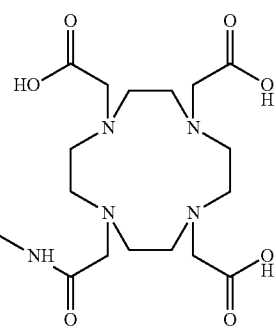
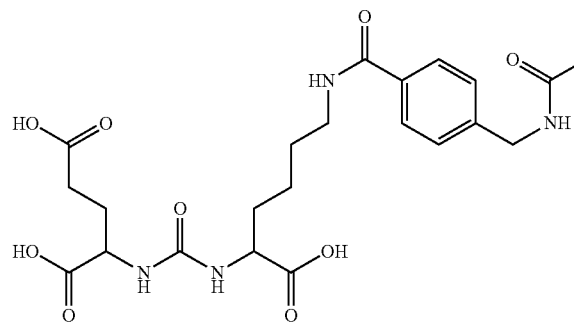
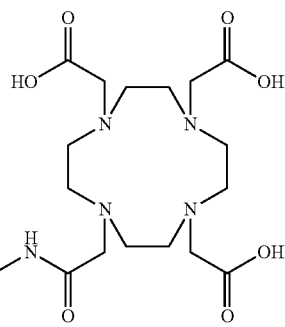
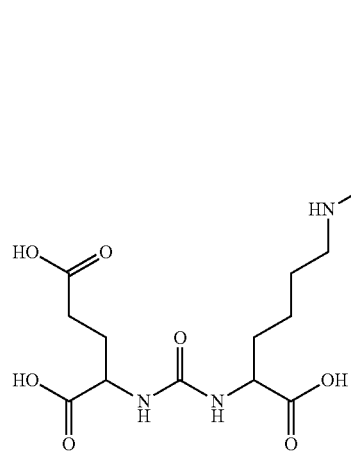
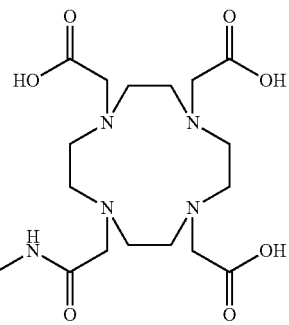
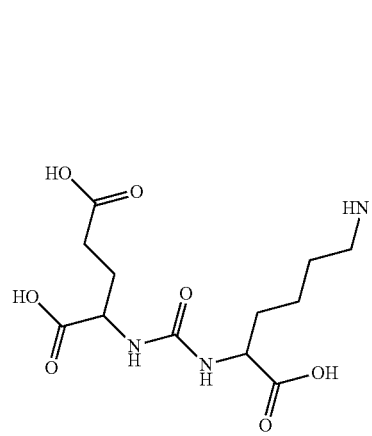

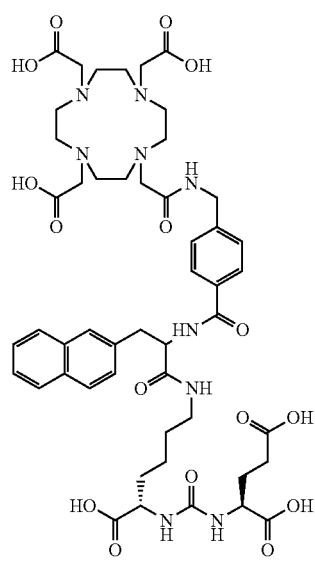
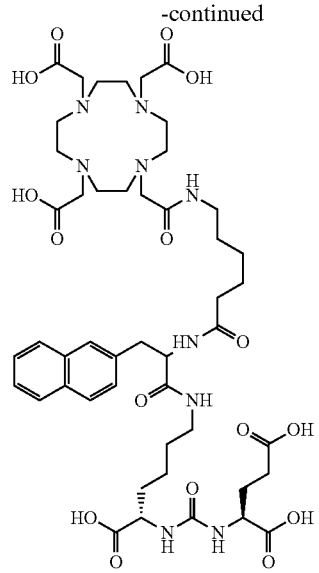
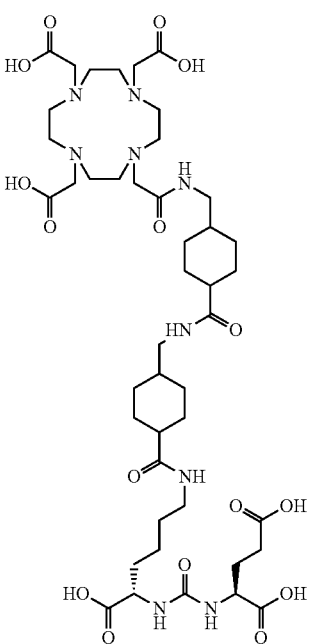
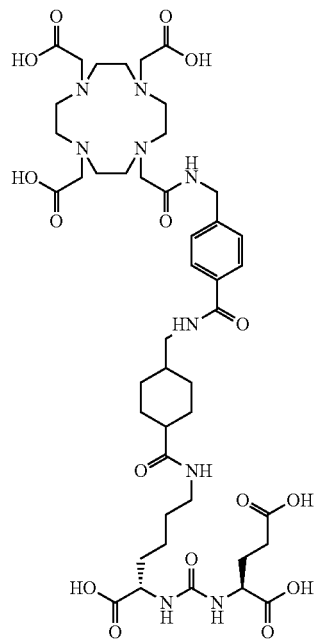
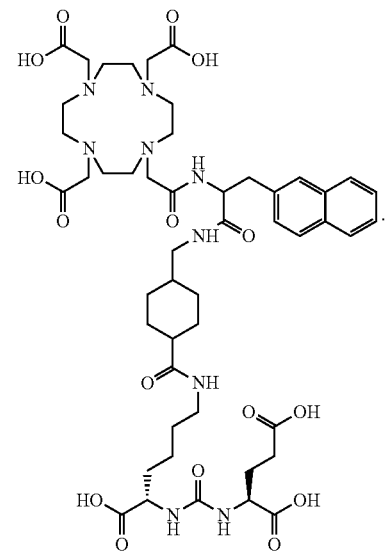

4. Use of the compound of any of paragraphs 1 to 3 for the preparation of radiolabeled compounds.

5. A metal complex comprising a radionuclide and a compound of any of paragraphs 1 to 3.

6. The metal complex of paragraph 5, wherein the radionuclide is $^{111}$In, $^{90}$Y, $^{68}$Ga, $^{177}$Lu, $^{99m}$Tc, $^{64}$Cu, $^{153}$Gd, $^{155}$Gd, $^{157}$Gd, $^{213}$Bi, $^{225}$Ac or Fe.

7. A pharmaceutical composition comprising a compound of any of paragraphs 1 to 3 or metal complex of paragraph 5 or 6, or a pharmaceutically acceptable salt, or ester thereof, and a pharmaceutically acceptable carrier.

8. Compound of any of paragraphs 1 to 3 or metal complex of paragraph 5 or 6 for use in a method of imaging in a patient.

9. Compound of any of paragraphs 1 to 3 or metal complex of paragraph 5 or 6 for use in a method of diagnosing prostate cancer and/or metastasis thereof.

10. Compound of any of paragraphs 1 to 3 or metal complex of paragraph 5 or 6 for use in a method of treating prostate cancer and/or metastasis thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of the formula:

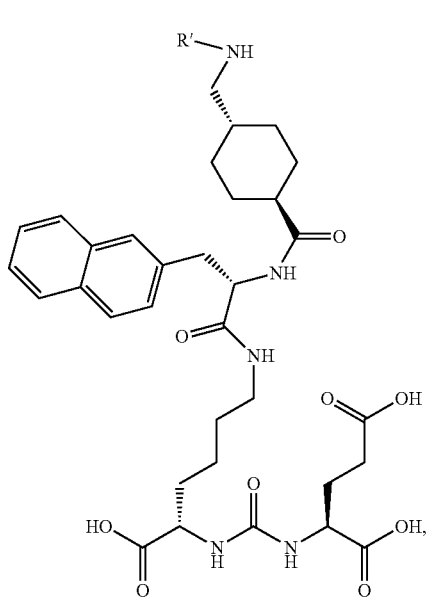

or a salt thereof,
wherein R' is a chelator of the formula:

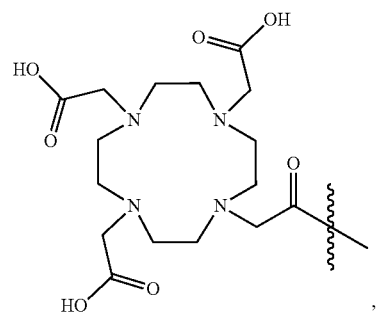 [SMILES: *C(=O)CN1CCN(CC(=O)O)CCN(CC(=O)O)CCN(CC(=O)O)CC1]

and
wherein $^{90}Y$ is complexed to the chelator.

2. A composition comprising:
   (1) the compound and/or a salt thereof according to claim 1; and
   (2) optionally a pharmaceutically acceptable carrier.

3. The composition of claim 2, wherein the composition further comprises an excipient, and wherein the excipient is different from said pharmaceutically acceptable carrier.

4. The composition of claim 2, wherein the composition is a buffered solution.

5. The composition of claim 2, wherein the pharmaceutically acceptable carrier is selected from mannitol, lactose, glucose, albumin, or a combination thereof.

6. A compound of the formula:

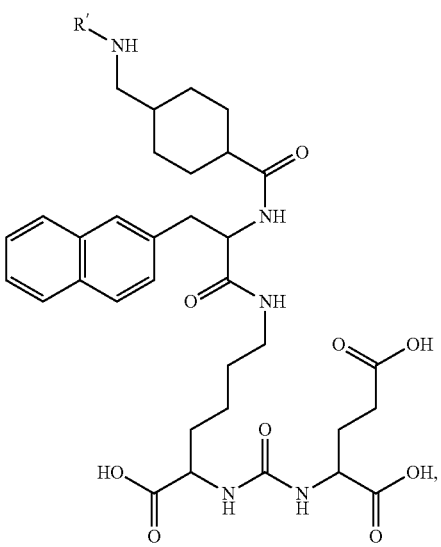

or a salt thereof,
wherein R' is a chelator of the formula:

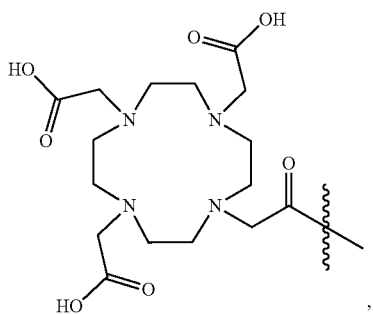 [SMILES: *C(=O)CN1CCN(CC(=O)O)CCN(CC(=O)O)CCN(CC(=O)O)CC1]

and
wherein $^{90}Y$ is complexed to the chelator.

7. A composition comprising:
   (1) the compound and/or a salt thereof according to claim 6; and
   (2) optionally a pharmaceutically acceptable carrier.

8. The composition of claim 7, wherein the composition further comprises an excipient, and wherein the excipient is different from said pharmaceutically acceptable carrier.

9. The composition of claim 7, wherein the composition is a buffered solution.

10. The composition of claim 7, wherein the pharmaceutically acceptable carrier is selected from mannitol, lactose, glucose, and albumin.

11. A compound of the formula:

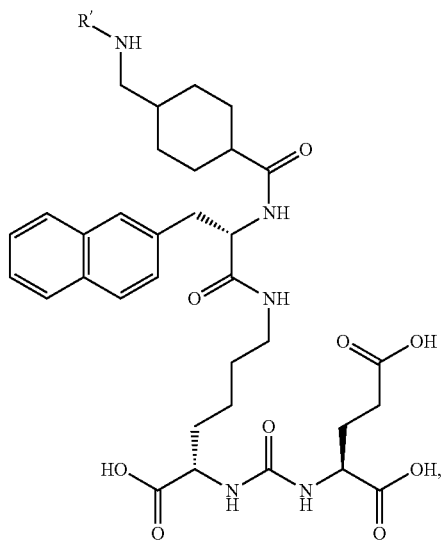

or a salt thereof,
wherein R' is a chelator of the formula:

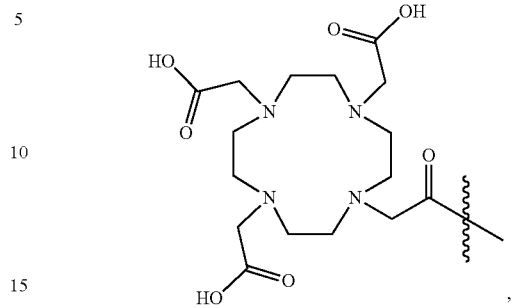

and
wherein $^{90}$Y is complexed to the chelator.

12. A composition comprising:
(1) the compound and/or a salt thereof according to claim 11; and
(2) optionally a pharmaceutically acceptable carrier.

13. The composition of claim 12, wherein the composition further comprises an excipient, and wherein the excipient is different from said pharmaceutically acceptable carrier.

14. The composition of claim 12, wherein the composition is a buffered solution.

15. The composition of claim 12, wherein the pharmaceutically acceptable carrier is selected from mannitol, lactose, glucose, albumin, or a combination thereof.

* * * * *